US008293915B2

(12) United States Patent
Tully et al.

(10) Patent No.: US 8,293,915 B2
(45) Date of Patent: Oct. 23, 2012

(54) COMPOUNDS AND COMPOSITIONS AS CHANNEL ACTIVATING PROTEASE INHIBITORS

(75) Inventors: David C. Tully, San Diego, CA (US); Arnab K. Chatterjee, San Diego, CA (US); Zhiwei Wang, Carlsbad, CA (US)

(73) Assignee: IRM LLC, Hamilton (BM)

( * ) Notice: Subject to any disclaimer, the term of this patent is extended or adjusted under 35 U.S.C. 154(b) by 174 days.

(21) Appl. No.: 12/526,029

(22) PCT Filed: Jan. 7, 2008

(86) PCT No.: PCT/US2008/050403
§ 371 (c)(1),
(2), (4) Date: Oct. 5, 2009

(87) PCT Pub. No.: WO2008/097676
PCT Pub. Date: Aug. 14, 2008

(65) Prior Publication Data
US 2010/0056756 A1     Mar. 4, 2010

Related U.S. Application Data

(60) Provisional application No. 60/889,018, filed on Feb. 9, 2007.

(51) Int. Cl.
C07D 401/06        (2006.01)
A61K 31/435        (2006.01)
(52) U.S. Cl. ........................................ 546/208; 514/326
(58) Field of Classification Search .................. 546/208; 514/326
See application file for complete search history.

(56) References Cited

U.S. PATENT DOCUMENTS

| | | | |
|---|---|---|---|
| 5,523,308 A | 6/1996 | Costanzo et al. | |
| 5,710,130 A | 1/1998 | Schacht et al. | |
| 5,874,585 A | 2/1999 | Gyorkos et al. | |
| 6,022,861 A | 2/2000 | Scarborough et al. | |
| 6,211,154 B1 | 4/2001 | Scarborough et al. | |
| 6,323,219 B1 | 11/2001 | Costanzo | |
| 6,469,036 B1 | 10/2002 | Costanzo et al. | |
| 7,939,547 B2 | 5/2011 | Tully et al. | |
| 7,951,823 B2 | 5/2011 | Tully et al. | |
| 2003/0216325 A1 | 11/2003 | Saksena et al. | |
| 2006/0275366 A1 | 12/2006 | Malcolm et al. | |
| 2007/0032433 A1 | 2/2007 | Saksena et al. | |
| 2007/0275906 A1 | 11/2007 | Tully et al. | |
| 2007/0276002 A1 | 11/2007 | Tully et al. | |
| 2008/0176901 A1 | 7/2008 | Tully et al. | |
| 2010/0239551 A1 | 9/2010 | Tully et al. | |

FOREIGN PATENT DOCUMENTS

| | | |
|---|---|---|
| EP | 0291234 | 3/1994 |
| EP | 1 114 822 A2 | 7/2001 |
| EP | 1 157 998 A1 | 11/2001 |
| JP | 08-020597 | 1/1996 |
| JP | 2002-138048 A | 5/2002 |
| WO | 95/33763 A1 | 12/1995 |
| WO | 96/11697 | 4/1996 |
| WO | 96/16080 A1 | 5/1996 |
| WO | 96/40741 | 12/1996 |
| WO | 96/40742 | 12/1996 |
| WO | 96/40744 | 12/1996 |
| WO | 96/40748 | 12/1996 |
| WO | 97/17363 A1 | 5/1997 |
| WO | 97/31939 | 9/1997 |
| WO | 97/48687 | 12/1997 |
| WO | 98/07308 | 2/1998 |
| WO | 98/24806 | 6/1998 |
| WO | 98/49190 | 11/1998 |
| WO | 98/50420 A1 | 11/1998 |
| WO | 99/07734 | 2/1999 |
| WO | 00/23421 | 4/2000 |
| WO | 00/39124 | 7/2000 |
| WO | 00/44733 | 8/2000 |
| WO | 01/02424 | 1/2001 |
| WO | 01/27096 | 4/2001 |
| WO | 01/40262 A1 | 6/2001 |
| WO | 01/44226 | 6/2001 |
| WO | 02/08244 | 1/2002 |
| WO | 02/18369 | 3/2002 |
| WO | 03/006490 A1 | 1/2003 |
| WO | 03/062265 | 7/2003 |
| WO | 03/072528 A2 | 9/2003 |
| WO | 2005/023804 | 3/2005 |
| WO | 2005/035525 A1 | 4/2005 |
| WO | 2005/037860 | 4/2005 |
| WO | 2005/058821 A1 | 6/2005 |
| WO | 2005/076886 | 8/2005 |
| WO | 2005/087721 | 9/2005 |
| WO | 2005/090329 A1 | 9/2005 |
| WO | 2005/113581 A1 | 12/2005 |
| WO | 2006/108643 A2 | 10/2006 |
| WO | 2007/137080 | 11/2007 |
| WO | 2007/140117 A1 | 12/2007 |
| WO | 2006/006644 | 1/2008 |
| WO | 2008/085608 A1 | 7/2008 |
| WO | 2008/097673 A1 | 8/2008 |
| WO | 2008/097676 A1 | 8/2008 |

OTHER PUBLICATIONS

Perni et al. (Bioorg. Med. Chem. Lett. 14 (2004) 1441-1446).*
Kubinyi (3D QSAR in Drug Design: Ligand-Protein Interactions and Molecular Similarity, vol. 2-3, Springer, 1998, 800 pages). TOC and pp. 243-244 provided.*
The Practice of Medicinal Chemsitry, 2d ed. (2003), 768 pages. Chs. 9-10 provided.*
Babine et al. (CAPLUS Abstract of WO 2002018369).*

(Continued)

Primary Examiner — Robert Havlin
(74) Attorney, Agent, or Firm — Emily Tongco Wu; Genomics Institute of the Novartis Research Foundation

(57) ABSTRACT

The invention provides compounds and pharmaceutical compositions thereof, which are useful for modulating channel activating proteases, and methods for, using such compounds to treat, ameliorate or prevent a condition associated with a channel activating protease, including but not limited to prostasin, PRSS22, TMPRSS11 (e.g., TMPRSS11B, TMPRSS11E), TMPRSS2, TMPRSS3, TMPRSS4 (MTSP-2), matriptase (MTSP-1), CAP2, CAP3, trypsin, cathepsin A, or neutrophil elastase.

12 Claims, No Drawings

OTHER PUBLICATIONS

Edwards et al., "Discovery and Biological Activity of Orally Active Petidyl Trifluoromethyl Ketone Inhibitors of Human Neutrophil Elastase", J. Med. Chem. 1997 vol. 40, pp. 1876-1885.

Costanzo et al., "In-Depth Study of Tripeptide-Based α-Ketoheterocycles as Inhibitors of Thrombin. Effective Utilization of the S1' Subsite and Its Implications to Structure-Based Drug Design1", J. Med. Chem., vol. 48, pp. 1984-2008, 2005.

Planes et al., "Regulation of the Epithelial Na+ Channel by Peptidases", Current Topics in Developmental Biology, 2007, vol. 78:23-46; pp. 1-19, NIH Public Access.

English translation of JP8020597 (JP1996020597A), Meiji Seika Kaisha Ltd., published Jan. 23,1996.

Costanzo et al., "Potent, Small-Molecule Inhibitors of Human Mast Cell Tryptase. Antiasthmatic Action of a Dipeptide-Based Transition-State Analogue Containing a Benzothiazole Ketone", J. Med. Chem., vol. 46, pp. 3865-3876, 2003.

Donnelly et al., "Therapy for Chronic Obstructive Pulmonary Disease in the 21st Century", Drugs 2003, vol. 63, No. 19, pp. 1973-1998.

\* cited by examiner

COMPOUNDS AND COMPOSITIONS AS CHANNEL ACTIVATING PROTEASE INHIBITORS

CROSS-REFERENCE TO RELATED APPLICATIONS

This application is a 371 U.S. national phase application of international application number PCT/US2008/050403 filed 7 Jan. 2008, which application claims priority to U.S. provisional patent application No. 60/889,018, filed 9 Feb. 2007. The full disclosure of these applications is incorporated herein by reference in its entirety and for all purposes.

TECHNICAL FIELD

The invention generally relates to channel activating protease (CAP) inhibitors.

BACKGROUND ART

Prostasin is a trypsin-like serine protease that is present in a variety of mammalian tissues. It is a membrane anchored protease that is expressed on the extra-cellular membrane of cells but that can also be secreted into body fluids such as semen, urine and airway surface liquid. Prostasin (PRSS8), together with proteases such as matriptase, CAP2, CAP3, trypsin, PRSS22, TMPRSS11, cathepsin A, and neutrophil elastase, can stimulate the activity of the amiloride-sensitive epithelial sodium channel (ENaC). Inhibiting these enzymes can induce changes in epithelial ion transport and therefore fluid homeostasis across epithelial membranes. For example, CAP inhibition in the kidney is thought to promote diuresis, whilst CAP inhibition in the airways promotes the clearance of mucus and sputum in lung. CAP inhibition in the kidney may therefore be used therapeutically to treat hypertension. CAP inhibition in the airways prevents the stagnation of respiratory secretions that otherwise tends to make sufferers vulnerable to secondary bacterial infections.

DISCLOSURE OF THE INVENTION

The invention provides compounds, pharmaceutical compositions and methods of using such compounds for modulating channel activating proteases (CAP). For example, the compounds and compositions of the invention may be used for modulating prostasin, PRSS22, TMPRSS11 (e.g., TMPRSS11B, TMPRSS11E), TMPRSS2, TMPRSS3, TMPRSS4 (MTSP-2), matriptase (MTSP-1), CAP2, CAP3, trypsin, cathepsin A, and neutrophil elastase.

In one aspect, the present invention provides compounds of Formula (1):

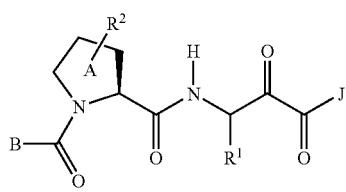

(1)

or pharmaceutically acceptable salts thereof; wherein B is

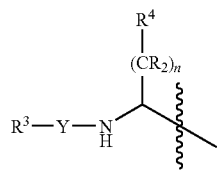

or $(CR_2)_k R^5$;

Y is $-SO_2-$, $-NHCO-$, $-CO-$ or $-O-C(=O)-$;

J is a $NH(CR_2)_l-R^6$, $NH(CR_2)_l-OR^6$, $NH(CR_2)_l-S_2-R^6$, $NH-CR[(CR_2)_l R^6]_2$, $OH$ or $OR^6$;

$R^1$ is $-(CR_2)_m-NR_2$, $-(CR_2)_m-NRC(=NR)-NR_2$ or $-(CR_2)_m-C(=NR)-NR_2$, or an optionally substituted 5-7 membered nitrogen-containing heterocyclic ring; or $R^1$ is $C_{1-6}$ alkyl or $(CR_2)_m-X$ wherein X is $C_{3-7}$ cycloalkyl or aryl, each of which is optionally substituted with $-(CR_2)_m-NR_2$, $-(CR_2)_m-NRC(=NR)-NR_2$ or $-(CR_2)_m-C(=NR)-NR_2$;

$R^2$ is a substituent at any position on ring A and is $-O-(CR_2)_p-R^7$ or $-L-NR^8 R^9$ wherein L is S, S(O), $SO_2$ or OC(O);

$R^3$ is $C_{1-6}$ alkyl, $C_{2-6}$ alkenyl, $C_{2-6}$ alkynyl or $-(CR_2)_l-R^7$;

$R^4$ is H, $C_{1-6}$ alkyl, $C_{2-6}$ alkenyl, $-CR=CR-R^6$, $C_{2-6}$ alkynyl, or an optionally substituted 5-12 membered carbocyclic ring, heterocyclic ring, aryl or heteroaryl; or $R^4$ is

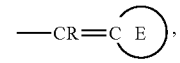

wherein ring E is an optionally substituted 5-12 membered monocyclic or fused carbocyclic or heterocyclic ring;

$R^5$ and $R^7$ are independently an optionally substituted 5-7 membered carbocyclic ring, heterocyclic ring, aryl or heteroaryl;

$R^6$ is $C_{1-6}$ alkyl, $C_{2-6}$ alkenyl, $C_{2-6}$ alkynyl, or an optionally substituted 5-12 membered carbocyclic ring, heterocyclic ring, aryl or heteroaryl;

$R^8$ and $R^9$ are independently H, $C_{1-6}$ alkyl, $C_{2-6}$ alkenyl, $C_{2-6}$ alkynyl or $-(CR_2)_l-R^7$; or $R^8$ and $R^9$ together with N may form an optionally substituted 5-7 membered heterocyclic ring;

each R is H, or $C_{1-6}$ alkyl, $C_{2-6}$ alkenyl, or $C_{2-6}$ alkynyl;

l is 0-6; and k, m, n and p are independently 1-6.

In the above Formula (1), $R^1$ may be $C_{1-6}$ alkyl, $-(CH_2)_m-NH_2$, $-(CH_2)_m-NHC(=NH)-NH_2$, or $(CH_2)_m-X$ wherein X is piperidinyl, $C_{3-7}$ cycloalkyl or phenyl. In other examples, $R^2$ is $-O-(CH_2)-R^7$ and $R^7$ is a halo-substituted phenyl.

In one embodiment, the invention provides compounds having Formula (2):

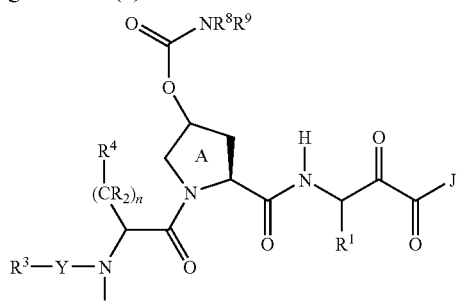

(2)

wherein $R^8$ and $R^9$ together form an optionally substituted 5-7 membered nitrogen-containing heterocyclic ring; and R, $R^1$, $R^3$, $R^4$, Y, J and n are as defined in Formula (1).

In another embodiment, the invention provides compounds having Formula (3):

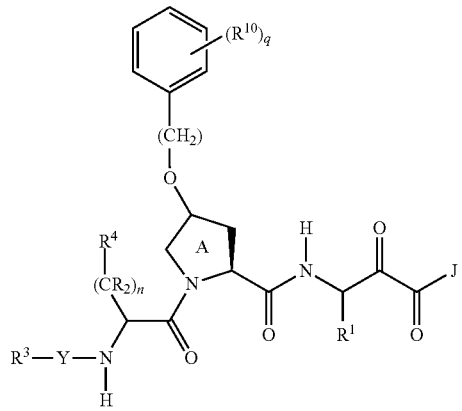

(3)

wherein q is 1-5;
$R^{10}$ is halo, $C_{1-6}$ alkyl, or $O(C_{1-6}$ alkyl); and
R, $R^1$, $R^3$, $R^4$, Y, J and n are as defined in Formula (1).

In the above Formula (2) and (3), Y may be $SO_2$ or —O—C(=O)—. In some examples, q is 1 and $R^{10}$ is p-chloro.

In the above Formula (2) and (3), $R^1$ may be —$(CH_2)_m$—$NH_2$, —$(CH_2)_m$—NHC(=NH)—$NH_2$, or $(CH_2)_m$—X wherein X is piperidinyl. In other examples, $R^3$ is $C_{1-6}$ alkyl, or an optionally substituted cyclohexyl, or benzyl. In yet other examples, $R^4$ is H, $C_{1-6}$ alkyl, $C_{2-6}$ alkenyl or —CR=CR—$R^6$ wherein $R^6$ is $C_{1-6}$ alkyl or an optionally substituted phenyl; or $R^4$ is an optionally substituted phenyl, piperidinyl, cyclohexyl,

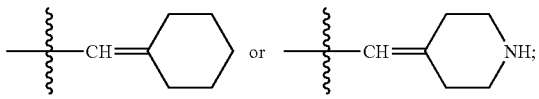

wherein each optionally substituted moiety is optionally substituted with $C_{1-6}$ alkyl, hydroxyl, $OR^6$, or $NR_2$. In particular examples, $R^4$ is piperidinyl.

In some embodiments, the invention provides compounds having Formula (3), wherein $R^1$ is $C_{1-6}$ alkyl or $(CR_2)_m$—X wherein X is $C_{3-7}$ cycloalkyl or phenyl; $R^4$ is an optionally substituted 5-7 membered nitrogen-containing heterocyclic ring; and Y is $SO_2$.

In yet another embodiment, the invention provides compounds having Formula (4):

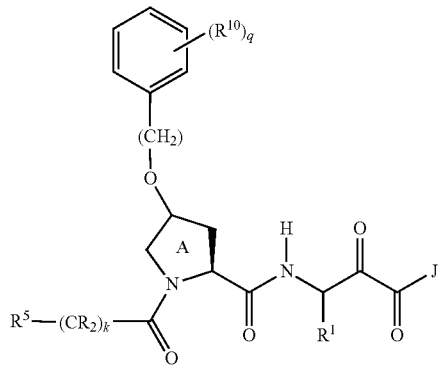

(4)

wherein q is 1-5;
$R^5$ is 5-7 membered heterocyclic ring containing N, O, or S;
$R^{10}$ is halo, $C_{1-6}$ alkyl, or $O(C_{1-6}$ alkyl); and
R, $R^1$, $R^5$, J and k are as defined in Formula (1).

In the above Formula (4), $R^5$ may be thiazolyl, optionally substituted with $NR^8R^9$. In some examples, $R^5$ is a thiazolyl that is optionally substituted with piperidinyl.

In the above Formula (1), (2), (3) and (4), J may be OH, $OCH_3$, NH—CH(phenyl)$_2$, NH(CH$_2$)$_l$—$OR^6$, NH(CH$_2$)$_l$—$SO_2$—$R^6$ or NH(CR$_2$)$_l$—$R^6$, wherein $R^6$ is $C_{1-6}$ alkyl, or phenyl, pyridyl, cyclopropyl, cyclohexyl, benzothiazolyl, 2,3-dihydro-1H-indenyl, morpholinyl, imidazolyl, tetrahydropyranyl, piperidinyl, thiophenyl, 2,3-dihydrobenzo[b][1,4]-dioxinyl or benzothiophenyl, each of which is optionally substituted with $C_{1-6}$ alkyl, halo, hydroxyl, $C_{1-6}$ alkoxy, $O(CR_2)_tR^5$, $SO_2NR_2$, $CONR(CR_2)_tR^6$ or $CONR^8R^9$.

In another aspect, the present invention provides pharmaceutical compositions comprising a compound of Formula (1), (2), (3) or (4), and a pharmaceutically acceptable excipient.

The invention also provides methods for modulating a channel activating protease, comprising administering to a system or a mammal, a therapeutically effective amount of a compound having Formula (1), (2), (3) or (4), or pharmaceutically acceptable salts or pharmaceutical compositions thereof, thereby modulating said channel activating protease.

In one embodiment, the invention provides a method for inhibiting a channel activating protease, comprising administering to a cell or tissue system or to a mammal, a therapeutically effective amount of a compound having Formula (1), (2), (3) or (4) or pharmaceutically acceptable salts or pharmaceutical compositions thereof; wherein said channel activating protease is prostasin, PRSS22, TMPRSS11 (e.g., TMPRSS11B, TMPRSS11E), TMPRSS2, TMPRSS3, TMPRSS4 (MTSP-2), matriptase (MTSP-1), CAP2, CAP3, trypsin, cathepsin A, or neutrophil elastase, thereby inhibiting said channel activating protease. In particular examples, the invention provides a method for inhibiting prostasin.

In another aspect, the invention provides a method for ameliorating or treating a condition mediated by a channel activating protease, comprising administering to a cell or tissue system or to a mammal, an effective amount of a compound having Formula (1), (2), (3) or (4), or pharmaceutically acceptable salts or pharmaceutical compositions thereof, and optionally in combination with a second therapeutic agent; wherein said channel activating protease is prostasin, PRSS22, TMPRSS11 (e.g., TMPRSS11B, TMPRSS11E), TMPRSS2, TMPRSS3, TMPRSS4 (MTSP-2), matriptase (MTSP-1), CAP2, CAP3, trypsin, cathepsin A, or neutrophil elastase, thereby treating said condition.

Furthermore, the present invention provides compounds of Formula (1), (2), (3) or (4), for use in a method for treating a condition mediated by a channel activating protease. The present invention also provides the use of a compound of Formula (1), (2), (3) or (4), and optionally in combination with a second therapeutic agent, in the manufacture of a medicament for treating a condition mediated by a channel activating protease.

In particular examples, the compounds of the invention may be used for treating a prostasin-mediated condition. In one embodiment, the second therapeutic agent may be an anti-inflammatory, bronchodilatory, antihistamine, anti-tussive, antibiotic or DNase, and is administered prior to, simultaneously with, or after the compound of Formula (1), (2), (3) or (4). In some examples, the compounds of the invention are administered to bronchial epithelial cells, particularly human bronchial epithelial cells.

Examples of conditions which may be ameliorated or treated using the compounds of the invention include but are not limited to a condition associated with the movement of fluid across ion transporting epithelia or the accumulation of mucus and sputum in respiratory tissues, or a combination thereof. In some examples, the condition which may be mediated using the compounds of the invention is cystic fibrosis, primary ciliary dyskinesia, lung carcinoma, chronic bronchitis, chronic obstructive pulmonary disease, asthma or a respiratory tract infection.

DEFINITIONS

"Alkyl" refers to a moiety and as a structural element of other groups, for example halo-substituted-alkyl and alkoxy, and may be straight-chained or branched. An optionally substituted alkyl, alkenyl or alkynyl as used herein may be optionally halogenated (e.g., $CF_3$), or may have one or more carbons that is substituted or replaced with a heteroatom, such as NR, O or S (e.g., —$OCH_2CH_2O$—, alkylthiols, thioalkoxy, alkylamines, etc).

"Aryl" refers to a monocyclic or fused bicyclic aromatic ring containing carbon atoms. For example, aryl may be phenyl or naphthyl. "Arylene" means a divalent radical derived from an aryl group.

"Heteroaryl" as used herein is as defined for aryl above, where one or more of the ring members is a heteroatom. Examples of heteroaryls include but are not limited to pyridyl, indolyl, indazolyl, quinoxalinyl, quinolinyl, benzofuranyl, benzopyranyl, benzothiopyranyl, benzo[1,3]dioxole, imidazolyl, benzo-imidazolyl, pyrimidinyl, furanyl, oxazolyl, isoxazolyl, triazolyl, tetrazolyl, pyrazolyl, thienyl, etc.

A "carbocyclic ring" as used herein refers to a saturated or partially unsaturated, monocyclic, fused bicyclic or bridged polycyclic ring containing carbon atoms, which may optionally be substituted, for example, with =O. Examples of carbocyclic rings include but are not limited to cyclopropyl, cyclobutyl, cyclopentyl, cyclohexyl, cyclopropylene, cyclohexanone, etc.

A "heterocyclic ring" as used herein is as defined for a carbocyclic ring above, wherein one or more ring carbons is a heteroatom. For example, a heterocyclic ring may contain N, O, S, —N=, —S—, —S(O), —S(O)$_2$—, or —NR— wherein R may be hydrogen, $C_{1-4}$alkyl or a protecting group. Examples of heterocyclic rings include but are not limited to morpholino, pyrrolidinyl, pyrrolidinyl-2-one, piperazinyl, piperidinyl, piperidinylone, 1,4-dioxa-8-aza-spiro[4.5]dec-8-yl, etc.

Unless otherwise indicated, when a substituent is deemed to be "optionally substituted," it is meant that the substituent is a group that may be substituted with one or more group(s) individually and independently selected from, for example, an optionally halogenated alkyl, alkenyl, alkynyl, alkoxy, alkylamine, alkylthio, alkynyl, amide, amino, including mono- and di-substituted amino groups, aryl, aryloxy, arylthio, carbonyl, carbocyclic, cyano, cycloalkyl, halogen, heteroalkyl, heteroalkenyl, heteroalkynyl, heteroaryl, heterocyclic, hydroxy, isocyanato, isothiocyanato, mercapto, nitro, O-carbamyl, N-carbamyl, O-thiocarbamyl, N-thiocarbamyl, C-amido, N-amido, S-sulfonamido, N-sulfonamido, C-carboxy, O-carboxy, perhaloalkyl, perfluoroalkyl, silyl, sulfonyl, thiocarbonyl, thiocyanato, trihalomethanesulfonyl, and the protected compounds thereof. The protecting groups that may form the protected compounds of the above substituents are known to those of skill in the art and may be found in references such as Greene and Wuts, Protective Groups in Organic Synthesis, 3$^{rd}$ Ed., John Wiley & Sons, New York, N.Y., 1999, and Kocienski, Protective Groups, Thieme Verlag, New York, N.Y., 1994, which are incorporated herein by reference in their entirety.

The terms "co-administration" or "combined administration" or the like as used herein are meant to encompass administration of the selected therapeutic agents to a single patient, and are intended to include treatment regimens in which the agents are not necessarily administered by the same route of administration or at the same time.

The term "pharmaceutical combination" as used herein refers to a product obtained from mixing or combining active ingredients, and includes both fixed and non-fixed combinations of the active ingredients. The term "fixed combination" means that the active ingredients, e.g. a compound of Formula (1) and a co-agent, are both administered to a patient simultaneously in the form of a single entity or dosage. The term "non-fixed combination" means that the active ingredients, e.g. a compound of Formula (I) and a co-agent, are both administered to a patient as separate entities either simultaneously, concurrently or sequentially with no specific time limits, wherein such administration provides therapeutically effective levels of the active ingredients in the body of the patient. The latter also applies to cocktail therapy, e.g. the administration of three or more active ingredients.

The term "therapeutically effective amount" means the amount of the subject compound that will elicit a biological or medical response in a cell, tissue, organ, system, animal or human that is being sought by the researcher, veterinarian, medical doctor or other clinician.

The term "administration" and or "administering" of the subject compound should be understood to mean as providing a compound of the invention including a prodrug of a compound of the invention to the individual in need of treatment.

As used herein, the terms "treat", "treating" and "treatment" refer to a method of alleviating or abating a disease and/or its attendant symptoms.

The term "prostasin" may also be referred to as: human channel-activating protease (hCAP); channel-activating protease-1; and PRSS8, MERPOPS ID S01.159.

MODES OF CARRYING OUT THE INVENTION

The invention provides compounds, pharmaceutical compositions and methods of using such compounds for modulating channel activating proteases (CAP).

In one aspect, the present invention provides compounds of Formula (1):

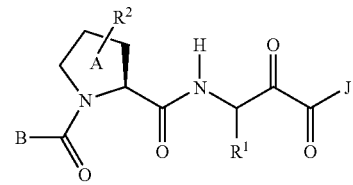

(1)

or pharmaceutically acceptable salts thereof; wherein B is

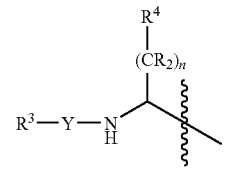

or $(CR_2)_k R^5$;

Y is a bond, —SO$_2$—, —NHCO—, —CO— or —O—C(=O)—;

J is a NH(CR$_2$)$_l$—R$^6$, NH(CR$_2$)$_l$—OR$^6$, NH(CR$_2$)$_l$—SO$_2$—R$^6$, NH—CR[(CR$_2$)$_l$R$^6$]$_2$, OH or OR$^6$;

R$^1$ is —(CR$_2$)$_m$—NR$_2$, —(CR$_2$)$_m$—NRC(=NR)—NR$_2$ or —(CR$_2$)$_m$—C(=NR)—NR$_2$, or an optionally substituted 5-7 membered nitrogen-containing heterocyclic ring; or R$^1$ is C$_{1-6}$ alkyl or (CR$_2$)$_m$—X wherein X is C$_{3-7}$ cycloalkyl or aryl, each of which is optionally substituted with —(CR$_2$)$_m$—NR$_2$, —(CR$_2$)$_m$—NRC(=NR)—NR$_2$ or —(CR$_2$)$_m$—C(=NR)—NR$_2$;

R$^2$ is a substituent at any position on ring A and is —O—(CR$_2$)$_p$—R$^7$ or -L-NR$^8$R$^9$ wherein L is S, S(O), SO$_2$ or OC(O); or R$^2$ is C$_{1-6}$ alkyl, C$_{2-6}$ alkenyl or C$_{2-6}$ alkynyl.

R$^3$ is C$_{1-6}$ alkyl, C$_{2-6}$ alkenyl, C$_{2-6}$ alkynyl or —(CR$_2$)$_l$—R$^7$;

R$^4$ is H, C$_{1-6}$ alkyl, C$_{2-6}$ alkenyl, —CR=CR—R$^6$, C$_{2-6}$ alkynyl, or an optionally substituted 5-12 membered carbocyclic ring, heterocyclic ring, aryl or heteroaryl; or R$^4$ is

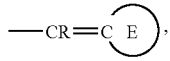

wherein ring E is an optionally substituted 5-12 membered monocyclic or fused carbocyclic or heterocyclic ring;

R$^5$ and R$^7$ are independently an optionally substituted 5-7 membered carbocyclic ring, heterocyclic ring, aryl or heteroaryl;

R$^6$ is C$_{1-6}$ alkyl, C$_{2-6}$ alkenyl, C$_{2-6}$ alkynyl, or an optionally substituted 5-12 membered carbocyclic ring, heterocyclic ring, aryl or heteroaryl;

R$^8$ and R$^9$ are independently H, C$_{1-6}$ alkyl, C$_{2-6}$ alkenyl, C$_{2-6}$ alkynyl or —(CR$_2$)$_l$—R$^7$; or R$^8$ and R$^9$ together with N may form an optionally substituted 5-7 membered heterocyclic ring;

each R is H, or C$_{1-6}$ alkyl, C$_{2-6}$ alkenyl, or C$_{2-6}$ alkynyl; and k, l, m, n and p are independently 0-6.

In particular examples, Y is —SO$_2$—, —NHCO—, —CO— or —O—C(=O)—; R$^2$ is —O—(CR$_2$)$_p$—R or -L-NR$^8$R$^9$ wherein L is S, S(O), SO$_2$ or OC(O); l is 0-6; and k, m, n and p are independently 1-6. In other examples, the substituent corresponding to R$^2$ may be in the 3-position of Ring A.

In one embodiment, the invention provides compounds having Formula (2):

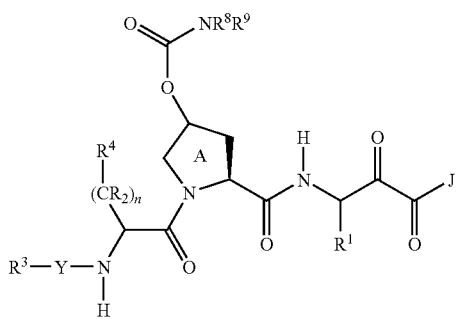

wherein R$^8$ and R$^9$ together form an optionally substituted 5-7 membered nitrogen-containing heterocyclic ring; and R, R$^1$, R$^3$, R$^4$, Y, J and n are as defined in Formula (1).

In another embodiment, the invention provides compounds having Formula (3):

wherein q is 1-5;

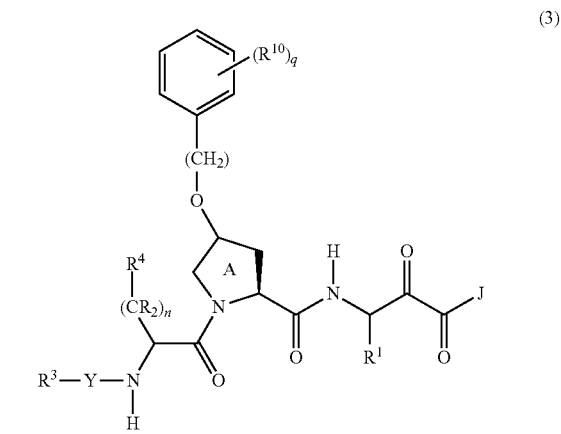

R$^{10}$ is halo, C$_{1-6}$ alkyl, or O(C$_{1-6}$ alkyl); and

R, R$^1$, R$^3$, R$^4$, Y, J and n are as defined in Formula (1).

In yet another embodiment, the invention provides compounds having Formula (4):

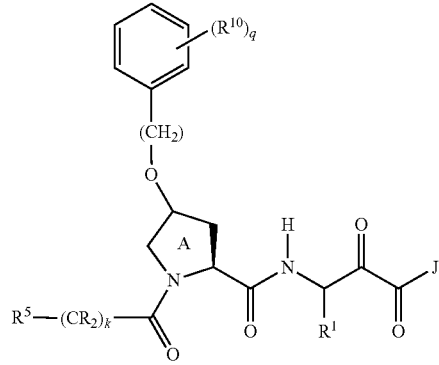

wherein q is 1-5;

R$^5$ is 5-7 membered heterocyclic ring containing N, O, or S;

R$^{10}$ is halo, C$_{1-6}$ alkyl, or O(C$_{1-6}$ alkyl); and

R, R$^1$, R$^5$, J and k are as defined in Formula (1).

In the above Formula (1), (2), (3) and (4), each optionally substituted moiety may be substituted with halo, =O, C$_{1-6}$ alkoxy, amino, C$_{1-6}$ alkyl, C$_{2-6}$ alkenyl or C$_{2-6}$ alkynyl, each of which may optionally be halogenated or may optionally have a carbon that may be replaced or substituted with N, O or S; CO$_2$R$^{11}$, O—(CR$_2$)$_l$—C(O)—R$^{11}$, —(CR$_2$)$_l$—R$^{11}$, —(CR$_2$)$_l$—C(O)—R$^{11}$, or —(CR$_2$)$_l$—SO$_2$—R$^{11}$; or a combination thereof, wherein each R$^{11}$ is H, amino, C$_{1-6}$ alkyl, or an optionally substituted carbocyclic ring, heterocyclic ring, aryl or heteroaryl. For example, J may be a phenyl substituted with one or more halo, C$_{1-6}$ alkoxy, SO$_2$NH$_2$, or —(CR$_2$)$_l$—C(O)—R$^{11}$ wherein R$^{11}$ is a 5-7 membered heterocyclic ring such as morpholinyl. In another example, R$^3$ may be thiazolyl substituted with one or more C$_{1-6}$ alkyl, or a 5-7 membered heterocyclic ring such as piperidinyl. In yet other examples, R$^4$ may be a phenyl substituted with C$_{1-6}$ alkoxy, or a methylenecyclohexane substituted with amino.

The present invention also includes all suitable isotopic variations of the compounds of the invention, or pharmaceutically acceptable salts thereof. An isotopic variation of a compound of the invention or a pharmaceutically acceptable salt thereof is defined as one in which at least one atom is replaced by an atom having the same atomic number but an atomic mass different from the atomic mass usually found in nature. Examples of isotopes that may be incorporated into the compounds of the invention and pharmaceutically acceptable salts thereof include but are not limited to isotopes of hydrogen, carbon, nitrogen and oxygen such as $^2$H, $^3$H, $^{11}$C, $^{13}$C, $^{14}$C, $^{15}$N, $^{17}$O, $^{18}$O, $^{35}$S, $^{18}$F, $^{36}$Cl and $^{123}$I. Certain isotopic variations of the compounds of the invention and pharmaceutically acceptable salts thereof, for example, those in which a radioactive isotope such as $^3$H or $^{14}$C is incorporated, are useful in drug and/or substrate tissue distribution studies. In particular examples, $^3$H and $^{14}$C isotopes may be used for their ease of preparation and detectability. In other examples, substitution with isotopes such as $^2$H may afford certain therapeutic advantages resulting from greater metabolic stability, such as increased in vivo half-life or reduced dosage requirements. Isotopic variations of the compounds of the invention or pharmaceutically acceptable salts thereof can generally be prepared by conventional procedures using appropriate isotopic variations of suitable reagents.

The compounds and compositions of the invention may be useful for modulating a channel activating protease. Examples of channel activating proteases which may be modulated using the compounds and compositions of the invention include but are not limited to prostasin, PRSS22, TMPRSS11 (e.g., TMPRSS11B, TMPRSS11E), TMPRSS2, TMPRSS3, TMPRSS4 (MTSP-2), matriptase (MTSP-1), CAP2, CAP3, trypsin, cathepsin A, or neutrophil elastase. The compounds of this invention may also inhibit the activity of proteases that stimulate the activity of ion channels, such as the epithelial sodium channel, and may be useful in the treatment of CAP-associated diseases.

Pharmacology and Utility

Compounds of the invention modulate the activity of channel activating protease, particularly trypsin-like serine proteases such as prostasin, and as such, are useful for treating diseases or disorders in which prostasin, for example, contribute to the pathology and/or symptomology of the disease.

Diseases mediated by inhibition of a channel activating protease, particularly by a trypsin-like serine protease such as prostasin, include diseases associated with the regulation of fluid volumes across epithelial membranes. For example, the volume of airway surface liquid is a key regulator of mucociliary clearance and the maintenance of lung health. The inhibition of a channel activating protease will promote fluid accumulation on the mucosal side of the airway epithelium thereby promoting mucus clearance and preventing the accumulation of mucus and sputum in respiratory tissues (including lung airways). Such diseases include respiratory diseases such as cystic fibrosis, primary ciliary dyskinesia, chronic bronchitis, chronic obstructive pulmonary disease (COPD), asthma, respiratory tract infections (acute and chronic; viral and bacterial) and lung carcinoma. Diseases mediated by inhibition of channel activating proteases also include diseases other than respiratory diseases that are associated with abnormal fluid regulation across an epithelium, perhaps involving abnormal physiology of the protective surface liquids on their surface, for example xerostomia (dry mouth) or keratoconjunctivitis sire (dry eye). Furthermore, CAP regulation of ENaC in the kidney could be used to promote diuresis and thereby induce a hypotensive effect.

Chronic obstructive pulmonary disease includes chronic bronchitis or dyspnoea associated therewith, emphysema, as well as exacerbation of airways hyper reactivity consequent to other drug therapy, in particular other inhaled drug therapy. The invention is also applicable to the treatment of bronchitis of whatever type or genesis including, for example, acute, arachidic, catarrhal, croupus, chronic or phthinoid bronchitis.

Asthma includes intrinsic (non-allergic) asthma and extrinsic (allergic) asthma, mild asthma, moderate asthma, severe asthma, bronchitic asthma, exercise-induced asthma, occupational asthma and asthma induced following bacterial infection. Asthma also encompasses a condition referred to as "wheezy-infant syndrome," which involves subjects less than 4 or 5 years of age who exhibit wheezing symptoms and diagnosed or diagnosable as "wheezy infants," an established patient category of major medical concern and often identified as incipient or early-phase asthmatics.

The suitability of a channel activating protease inhibitor such as a prostasin inhibitor for the treatment of a disease mediated by inhibition of a channel activating protease, may be tested by determining the inhibitory effect of the channel activating protease inhibitor according to the assays described below and following methods known in the art.

In accordance with the foregoing, the present invention further provides a method for preventing or treating any of the diseases or disorders described above in a subject in need of such treatment, which method comprises administering to said subject a therapeutically effective amount of a compound of Formula (1), (2), (3) or (4), or a pharmaceutically acceptable salt thereof. For any of the above uses, the required dosage will vary depending on the mode of administration, the particular condition to be treated and the effect desired. (See, "Administration and Pharmaceutical Compositions", infra).

Administration and Pharmaceutical Compositions

In general, compounds of the invention will be administered in therapeutically effective amounts via any of the usual and acceptable modes known in the art, either singly or in combination with one or more therapeutic agents.

Channel activating protease inhibitors of the invention are also useful as co-therapeutic agents for use in combination with another therapeutic agent. For example, a channel activating protease inhibitor may be used in combination with an anti-inflammatory, bronchodilatory, antihistamine or antitussive, antibiotic or DNase therapeutic agent. The channel activating protease inhibitor and other therapeutic agent may be in the same or different pharmaceutical composition. The channel activating protease inhibitor may be mixed with the other therapeutic agent in a fixed pharmaceutical composition, or it may be administered separately, before, simultaneously with or after the other therapeutic agent. The combination may be useful particularly in the treatment of cystic fibrosis or obstructive or inflammatory airways diseases such as those mentioned hereinbefore, for example as potentiators of therapeutic activity of such drugs or as a means of reducing required dosaging or potential side effects of such drugs.

Suitable anti-inflammatory therapeutic agents include steroids, in particular glucocorticosteroids such as budesonide, beclamethasone dipropionate, fluticasone propionate, ciclesonide or mometasone furoate, or steroids described in international patent application WO 02/88167, WO 02/12266, WO 02/100879, WO 02/00679 (for example, Examples 3, 11, 14, 17, 19, 26, 34, 37, 39, 51, 60, 67, 72, 73, 90, 99 and 101), WO 03/35668, WO 03/48181, WO 03/62259, WO 03/64445, WO 03/72592, WO 04/39827 and WO 04/66920; non-steroidal glucocorticoid receptor agonists, such as those described in DE 10261874, WO 00/00531, WO 02/10143, WO 03/82280, WO 03/82787, WO 03/86294, WO 03/104195, WO 03/101932, WO 04/05229, WO 04/18429, WO 04/19935 and WO 04/26248; LTD4 antagonists such as montelukast and zafirlukast; PDE4 inhibitors such cilomilast (ARIFLO® GlaxoSmithKline), ROFLUMILAST® (Byk Gulden), V-11294A (Napp), BAY 19-8004 (Bayer), SCH-351591 (Schering-Plough), AROFYLLINE® (Almirall Prodesfarma), PD189659/PD 168787 (Parke-Davis), AWD-12-281 (Asta Medica), CDC-801 (Celgene), SelCID™, CC-10004 (Celgene), VM554/ UM565 (Vernalis), T-440 (Tanabe), KW-4490 (Kyowa Hakko Kogyo), and those disclosed in WO 92/19594, WO 93/19749, WO 93/19750, WO 93/19751, WO 98/18796, WO 99/16766, WO 01/13953, WO 03/104204, WO 03/104205, WO 03/39544, WO 04/000814, WO 04/000839, WO 04/005258, WO 04/018450, WO 04/018451, WO 04/018457, WO 04/018465, WO 04/018431, WO 04/018449, WO 04/018450, WO 04/018451, WO 04/018457, WO 04/018465, WO 04/019944, WO 04/019945, WO 04/045607 and WO 04/037805; and adenosine $A_{2B}$ receptor antagonists such as those described in WO 02/42298, each of which is incorporated herein in its entirety.

Suitable bronchodilatory therapeutic agents include beta-2 adrenoceptor agonists such as albuterol (salbutamol), metaproterenol, terbutaline, salmeterol fenoterol, procaterol, formoterol, carmoterol, or pharmaceutically acceptable salts thereof, and compounds (in free or salt or solvate form) of Formula (1) as described in WO 00/75114, which is incorporated herein by reference in its entirety, such as a compound of formula:

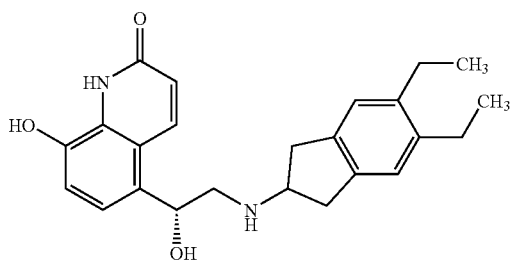

or pharmaceutically acceptable salts thereof, as well as compounds (in free or salt or solvate form) of Formula (1) of WO 04/16601, and also compounds of EP 1440966, JP 05025045, WO 93/18007, WO 99/64035, US 2002/0055651, WO 01/42193, WO 01/83462, WO 02/66422, WO 02/70490, WO 02/76933, WO 03/24439, WO 03/42160, WO 03/42164, WO 03/72539, WO 03/91204, WO 03/99764, WO 04/16578, WO 04/22547, WO 04/32921, WO 04/33412, WO 04/37768, WO 04/37773, WO 04/37807, WO 04/39762, WO 04/39766, WO 04/45618 WO 04/46083 and WO 04/80964, each of which is incorporated herein in its entirety.

Suitable bronchodilatory therapeutic agents also include anticholinergic or antimuscarinic agents, in particular ipratropium bromide, oxitropium bromide, tiotropium salts and CHF 4226 (Chiesi), and glycopyrrolate, but also those described in EP 424021, U.S. Pat. No. 3,714,357, U.S. Pat. No. 5,171,744, WO 01/04118, WO 02/00652, WO 02/51841, WO 02/53564, WO 03/00840, WO 03/33495, WO 03/53966, WO 03/87094, WO 04/018422 and WO 04/05285, each of which is incorporated herein in its entirety.

Suitable dual anti-inflammatory and bronchodilatory therapeutic agents include dual beta-2 adrenoceptor agonist/ muscarinic antagonists such as those disclosed in US 2004/ 0167167, WO 04/74246 and WO 04/74812.

Suitable antihistamine therapeutic agents include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine as well as those disclosed in JP 2004107299, WO 03/099807 and WO 04/026841, each of which is incorporated herein in its entirety.

Suitable antibiotics include macrolide antibiotics, for example tobramycin (TOBI™).

Suitable DNase therapeutic agents include dornase alfa (PULMOZYME™), a highly purified solution of recombinant human deoxyribonuclease I (rhDNase), which selectively cleaves DNA. Dornase alfa is used to treat cystic fibrosis.

Other useful combinations of channel activating protease inhibitors with anti-inflammatory therapeutic agents are those with antagonists of chemokine receptors, e.g. CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists such as Schering-Plough antagonists SC-351125, SCH-55700 and SCH-D, Takeda antagonists such as N-[[4-[[[6,7-dihydro-2-(4-methyl-phenyl)-5H-benzo-cyclohepten-8-yl]carbonyl]amino] phenyl]-methyl]tetrahydro-N,N-dimethyl-2H-pyran-4-amin-ium chloride (TAK-770), and CCR-5 antagonists described in U.S. Pat. No. 6,166,037, WO 00/66558, WO 00/66559, WO 04/018425 and WO 04/026873, each of which is incorporated herein in its entirety.

In the treatment of a disease mediated by inhibition of prostasin in accordance with the invention, a channel activating protease inhibitor of the invention, in free form or in pharmaceutically acceptable salt form, may be administered by any appropriate route, for example orally, e.g. in tablet, capsule or liquid form, parenterally, for example in the form of an injectable solution or suspension, or intranasally, for example in the form of an aerosol or other atomisable formulation using an appropriate intranasal delivery device, e.g. a nasal spray such as those known in the art, or by inhalation, particularly for use with a nebulizer.

The channel activating protease inhibitor may be administered in a pharmaceutical composition together with a pharmaceutically acceptable diluent or carrier. Such compositions may be, for example dry powders, tablets, capsules and liquids, but also injection solutions, infusion solutions or inhalation suspensions, which may be prepared using other formulating ingredients and techniques known in the art.

The dosage of the channel activating protease inhibitor in free form or in pharmaceutically acceptable salt form can depend on various factors, such as the activity and duration of action of the active ingredient, the severity of the condition to be treated, the mode of administration, the species, sex, ethnic origin, age and weight of the subject and/or its individual condition. A typical daily dose for administration, for example oral administration to a warm-blooded animal, particularly a human being weighing about 75 kg, is estimated to be from approximately 0.7 mg to approximately 1400 mg, more particularly from approximately 5 mg to approximately 200 mg. That dose may be administered, for example, in a single dose or in several part doses of, for example, from 5 to 200 mg.

When the composition comprises an aerosol formulation, it may contain, for example, a hydro-fluoro-alkane (HFA) propellant such as HFA134a or HFA227 or a mixture of these, and may contain one or more co-solvents known in the art such as ethanol (up to 20% by weight), and/or one or more surfactants such as oleic acid or sorbitan trioleate, and/or one or more bulking agents such as lactose. When the composition comprises a dry powder formulation, it may contain, for example, the channel activating protease inhibitor having a particle diameter up to 10 microns, optionally together with a diluent or carrier, such as lactose, of the desired particle size distribution and a compound that helps to protect against product performance deterioration due to moisture e.g. magnesium stearate. When the composition comprises a nebulised formulation, it may contain, for example, the channel activating protease inhibitor either dissolved, or suspended, in a vehicle containing water, a co-solvent such as ethanol or propylene glycol and a stabilizer, which may be a surfactant.

In particular embodiments, the invention provides compounds of Formula (1), (2), (3) and (4) in inhalable form, e.g. in an aerosol or other atomisable composition or in inhalable particulate, e.g. micronised, form. The invention also provides an inhalable medicament comprising compounds of the invention in inhalable form; a pharmaceutical product comprising compounds of the invention in inhalable form in association with an inhalation device; and an inhalation device comprising compounds of the invention in inhalable form.

Processes for Making Compounds of the Invention

The compounds of the invention may be prepared, following procedures exemplified in the Examples.

In the reactions described, reactive functional groups, where desired in the final product (e.g., hydroxy, amino, imino, thio or carboxy groups), may be protected using protecting groups known in the art, to avoid their unwanted participation in the reactions. Conventional protecting groups may be used in accordance with standard practice, for example, see T. W. Greene and P. G. M. Wuts in "Protective Groups in Organic Chemistry", John Wiley and Sons, 1991.

Compounds of the invention may also be prepared as a pharmaceutically acceptable acid addition salt by reacting the free base form of the compound with a pharmaceutically acceptable inorganic or organic acid. Alternatively, a pharmaceutically acceptable base addition salt of a compound of the invention may be prepared by reacting the free acid form of the compound with a pharmaceutically acceptable inorganic or organic base. Alternatively, salt forms of the compounds of the invention may be prepared using salts of the starting materials or intermediates.

The free acid or free base forms of the compounds of the invention may be prepared from the corresponding base addition salt or acid addition salt from, respectively. For example, a compound of the invention in an acid addition salt form may be converted to the corresponding free base by treating with a suitable base (e.g., ammonium hydroxide solution, sodium hydroxide, and the like). A compound of the invention in a base addition salt form may be converted to the corresponding free acid by treating with a suitable acid (e.g., hydrochloric acid, etc.).

Compounds of the invention in unoxidized form may be prepared from N-oxides of compounds of the invention by treating with a reducing agent (e.g., sulfur, sulfur dioxide, triphenyl phosphine, lithium borohydride, sodium borohydride, phosphorus trichloride, tribromide, or the like) in a suitable inert organic solvent (e.g. acetonitrile, ethanol, aqueous dioxane, or the like) at 0 to 80° C.

Prodrug derivatives of the compounds of the invention may be prepared by methods known to those of ordinary skill in the art (e.g., for further details see Saulnier et al., (1994), Bioorganic and Medicinal Chemistry Letters, Vol. 4, p. 1985). For example, appropriate prodrugs may be prepared by reacting a non-derivatized compound of the invention with a suitable carbamylating agent (e.g., 1,1-acyloxyalkylcarbanochloridate, para-nitrophenyl carbonate, or the like).

Protected derivatives of the compounds of the invention may be made by means known to those of ordinary skill in the art. A detailed description of techniques applicable to the creation of protecting groups and their removal may be found in T. W. Greene, "Protecting Groups in Organic Chemistry", 3rd edition, John Wiley and Sons, Inc., 1999.

Compounds of the present invention may be conveniently prepared, or formed during the process of the invention, as solvates (e.g., hydrates). Hydrates of compounds of the present invention may be conveniently prepared by recrystallization from an aqueous/organic solvent mixture, using organic solvents such as dioxin, tetrahydrofuran or methanol.

Compounds of the invention may be prepared as their individual stereoisomers by reacting a racemic mixture of the compound with an optically active resolving agent to form a pair of diastereoisomeric compounds, separating the diastereomers and recovering the optically pure enantiomers. While resolution of enantiomers may be carried out using covalent diastereomeric derivatives of the compounds of the invention, dissociable complexes are preferred (e.g., crystalline diastereomeric salts). Diastereomers have distinct physical properties (e.g., melting points, boiling points, solubilities, reactivity, etc.) and may be readily separated by taking advantage of these dissimilarities. The diastereomers may be separated by chromatography, or by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture may be found in Jean Jacques, Andre Collet, Samuel H. Wilen, "Enantiomers, Racemates and Resolutions", John Wiley And Sons, Inc., 1981.

In summary, the compounds of the invention may be prepared as exemplified in the Examples, and Formula (1), (2), (3) and (4) may be made by a process, which involves:

(a) optionally converting a compound of the invention into a pharmaceutically acceptable salt;

(b) optionally converting a salt form of a compound of the invention to a non-salt form;

(c) optionally converting an unoxidized form of a compound of the invention into a pharmaceutically acceptable N-oxide;

(d) optionally converting an N-oxide form of a compound of the invention to its unoxidized form;

(e) optionally resolving an individual isomer of a compound of the invention from a mixture of isomers;

(f) optionally converting a non-derivatized compound of the invention into a pharmaceutically acceptable prodrug derivative; and (g) optionally converting a prodrug derivative of a compound of the invention to its non-derivatized form.

Insofar as the production of the starting materials is not particularly described, the compounds are known or may be prepared analogously to methods known in the art or as disclosed in the Examples hereinafter. One of skill in the art will appreciate that the above transformations are only representative of methods for preparation of the compounds of the present invention, and that other well-known methods may similarly be used. The present invention is further exemplified, but not limited, by the following intermediates (Reference compounds) and Examples that illustrate the preparation of the compounds of the invention.

In one embodiment, the compounds of the invention have Formula (1), wherein $R^1$ is —$(CR_2)_m$—$NR_2$, —$(CR_2)_m$—

NRC(=NR)—NR$_2$ or —(CR$_2$)$_m$—C(=NR)—NR$_2$, or an optionally substituted 5-7 membered nitrogen-containing heterocyclic ring; or R$^1$ is (CR$_2$)$_m$—X wherein X is C$_{3-7}$ cycloalkyl or aryl that is substituted with —(CR$_2$)$_m$—NR$_2$, —(CR$_2$)$_m$—NRC(=NR)—NR$_2$ or —(CR$_2$)$_m$—C(=NR)—NR$_2$. Representative compounds may be prepared using the following reference compounds and examples.

Reference Compound 1

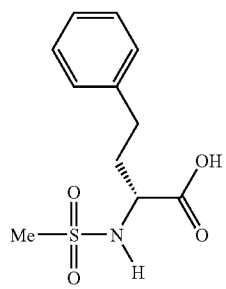

D-Homophenylalanine ethyl ester hydrochloride (5.00 g, 20.5 mmol) and DIPEA (8.7 mL, 51.25 mmol) are dissolved in THF (100 mL) and stirred at room temperature. Mesyl chloride (1.67 mL, 21.52 mmol) is added dropwise, and the reaction stirred 6 h at room temperature. The THF is evaporated; and the crude dissolved in EtOAc (100 mL) and washed with water (100 mL), 1N HCl (2×100 mL) and brine (100 mL), and dried (MgSO$_4$). The solvent is removed in vacuo and the crude material purified with flash chromatography (Hexanes:EtOAc) to afford the ethyl ester. The ethyl ester is dissolved in dioxane (50 mL) and stirred at room temperature. LiOH.H$_2$O (1.00 mg, 24 mmol) dissolved in water (20 mL) is added and the reaction stirred until the ethyl ester had disappeared (by TLC and LCMS). The solvent is removed in vacuo and the crude material is partitioned with EtOAc (50 mL) and 1N HCl (50 mL). The aqueous layer is extracted with EtOAc (2×50 mL) and the combined organic phases are washed with 1M NaHSO$_4$ (2×50 mL) and brine (50 mL), and dried with MgSO$_4$. The solvent is evaporated and the crude material purified by flash chromatography (EtOAc:Hexanes gradient) to afford Reference compound 1 as a white powder.

Reference Compound 2

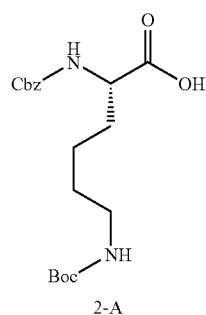

2-A

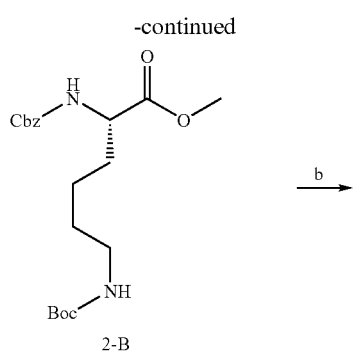

2-B

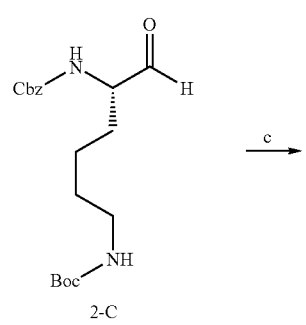

2-C

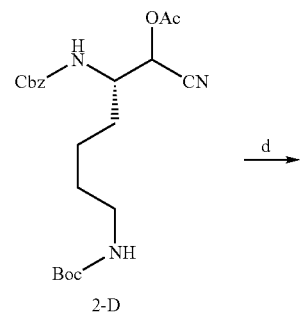

2-D

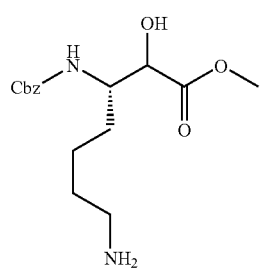

2-E

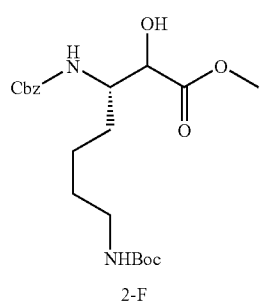

2-F

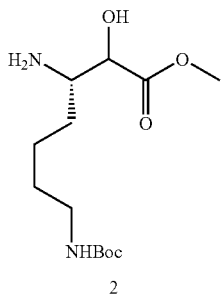

2

In the reaction scheme for Reference compound 2, the reagents and conditions are: (a) TBTU/CH$_2$Cl$_2$/CH$_3$OH, Et$_3$N, 23° C.; (b) DIBAL-H, CH$_2$Cl$_2$, −78° C.; (c) NaCN, TEBAC (cat.), Ac$_2$O, CH$_2$Cl$_2$/H$_2$O −20° C.; (d) 3M HCl (gas) in Et$_2$O, CH$_3$OH, 4° C. then H$_2$O, pH 11, 0° C.; (e) Boc$_2$O, DMF, Et$_3$N, 23° C.; (f) H$_2$, MeOH, Pd/C 10%, 23° C., 12 h.

2-B: A solution of Cbz-Lys(Boc)-OH (28 g, 73.60 mmol) and TBTU (23.5 g, 73.60 mmol) in 500 mL of CH$_2$Cl$_2$:MeOH (9:1) is adjusted to pH 8.0 by addition of Et$_3$N. The reaction is stirred at room temperature for 2 hours. The mixture is washed successively with cold 1N HCl solution, water, 5% NaHCO$_3$ solution, and water, and dried over Na$_2$SO$_4$. The filtrate is evaporated, and the residue is chromatographed on silica gel (heptane:EtOAc, 4:1) to provide 2-B. TLC (EtOAc: heptane, 3:1) R$_f$=0.85.

2-C: To a solution of 2-B (10.5 g, 26.6 mmol) in CH$_2$Cl$_2$ (350 mL) is added DIBAL-H (80 mL, 1M in hexanes solution) at −78° C., and the solution is allowed to stir at that temperature for 1 h. Citric acid (5% aqueous solution) is added to quench the reaction, and allowed to stir at room temperature for 10 minutes. The CH$_2$Cl$_2$ layer is separated, and the aqueous layer is washed with CH$_2$Cl$_2$ (2×200 mL). The combined organic layers are washed with water, dried over Na$_2$SO$_4$ and filtered The filtrate is evaporated, and the residue of 2-C is used immediately in the next step.

2-D: The crude solution of 2-C (9.6 g, 26.6 mmol) in CH$_2$Cl$_2$ (350 mL) is cooled to −20° C., and a solution of NaCN (15 g, 306 mmol), triethylbenzylammonium chloride (1.75 g, 7.67 mmol) in 245 mL of water is added. Acetic anhydride (7.7 mL, 81.6 mmol) is added dropwise over a 10 minute period with vigorous stirring. The reaction mixture is stirred for another 10 minutes and then the CH$_2$Cl$_2$ layer is separated. The aqueous layer is extracted with CH$_2$Cl$_2$. The combined organic layers are washed with water, dried over Na$_2$SO$_4$ and filtered. The filtrate is evaporated, and the residue of 2-D is purified by automated silica gel chromatography (30-40% ethyl acetate in hexanes). Collecting fractions containing the desired material provides 2-D. TLC (CH$_2$Cl$_2$: EtOAc, 7:3) R$_f$=0.6.

2-E: Intermediate 2-D is dissolved in anhydrous MeOH (80 mL) and diethyl ether (200 mL), and cooled to −20° C. HCl gas is bubbled through the solution until the weight increased to 36 g. The temperature is kept below 0° C. overnight then water is added, maintaining the reaction temperature at 0° C. Reaction is allowed to stir at room temperature for 16 hours, monitoring the reaction by LC/MS. Ether is removed in vacuo and the pH is adjusted to 11.0 maintaining the reaction at 0° C. by addition of aqueous NaOH. The reaction mixture is extracted with ethyl acetate, and dried over Na$_2$SO$_4$ and filtered. The crude material of 2-E is used directly in the next step. LC/MS (expected 325.2 (M+1), found 325.1).

2-F: Intermediate 2-E (4.94 g, 15.2 mmol) is dissolved in DMF (250 mL). Triethylamine (6.5 mL, 45 mmol) is added to adjust the pH to 8.0. Di-tert-butyl dicarbonate (5.0 g, 23 mmol) is added in one portion and the reaction is allowed to stir overnight at room temperature. The solvent is removed in vacuo and the residue is dissolved in ethyl acetate, washed with water and brine, dried over Na$_2$SO$_4$, filtered, and evaporated. The residue of 2-F is purified by automated silica gel chromatography (40% ethyl acetate in hexanes). Collecting fractions containing the desired material provides 2-F.

Reference compound 2: A solution of Compound 2-F (3.7 g, 8.73 mmol) is dissolved in ethanol (50 mL). Pd/C (10%, wet, Degussa type) is added, and the flask is placed on a Parr shaker overnight and subjected to 40 psi Hydrogen. The catalyst is filtered through Celite, and solvent is removed in vacuo. The solvent is removed in vacuo to afford the desired Reference compound 2 as a clear oil. LC/MS (expected 291.2 (M+H), found 291.4).

Reference Compound 3

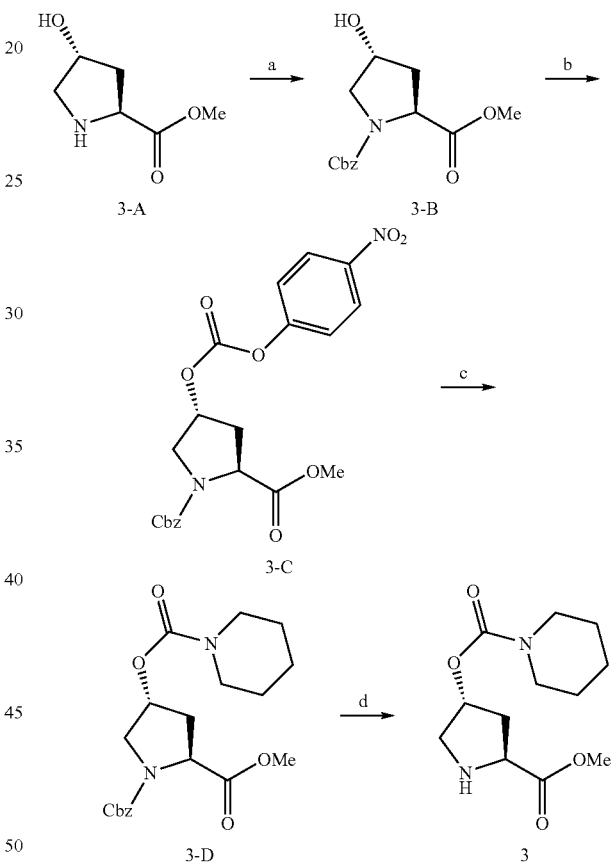

In the reaction scheme for Reference compound 3, the reagents and conditions are: (a) Cbz-OSu, Et$_3$N, THF, water, 23° C.; (b) p-nitrophenylchloroformate, pyridine, CH$_2$Cl$_2$, 23° C.; (c) Piperidine, CH$_2$Cl$_2$, 23° C., 72%; (d) H$_2$ Pd/C (40 psi), t-BuOH, H$_2$O, 23° C.

3-B: Compound 3-A (H-Hyp-OMe.HCl) (3.19 g, 17.55 mmol) and N-(benzyloxycarbonyloxy)-succinimide (Cbz-OSu) (4.37 g, 17.55 mmol) are added to a round bottomed flask containing THF (60 mL) and water (20 mL). The mixture is stirred at room temperature and Et$_3$N (11.6 mL, 70.2 mmol) is added, and the reaction is stirred overnight at room temperature. The clear solution is diluted with EtOAc (200 mL) and washed with 1N HCl (3×100 mL) and brine (1×100 mL), and dried with MgSO$_4$. Solvent is evaporated in vacuo to afford the desired product as a clear oil, which is used without further purification. MS m/z 280.1 (M+1).

3-C: 4-Nitrophenylchloroformate (1.514 g, 7.51 mmol) is added to a solution of 3-B (1.92 g, 6.83 mmol) and pyridine (663 µl, 8.19 mmol) in CH$_2$Cl$_2$ (100 ml). The reaction mixture is stirred overnight. The mixture is washed with three portions of NaHSO$_4$ 1M and two portions of brine; dried (MgSO$_4$) and concentrated in vacuo to give the compound 3-C as yellow oil; MS m/z 445.1 (M+1).

3-D: Piperidine (320 mg, 3.76 mmol) is added to a solution of 3-C (1.4 g, 3.14 mmol) in DCM (100 ml), and the solution mixture is stirred at room temperature for 3 hours. The mixture is then washed with three portions of aqueous 1M NaHSO$_4$, three portions of saturated aqueous NaHCO$_3$ and two portions of brine. The organic layer is dried (MgSO$_4$), and concentrated in vacuo. The residue is purified by automated silica gel (EtOAc/hexanes, 0 to 100%) to give the compound 3-D as oil. MS m/z 391.3 (M+1).

Reference compound 3: A solution of Compound 3-D (883 mg, 2.26 mmol) is dissolved in a 4:1 mixture of t-BuOH and water (50 mL). Pd/C (10%, wet, Degussa type) is added, and the flask is placed on a Parr shaker overnight and subjected to 40 psi hydrogen. The catalyst is filtered through Celite, and solvent is removed in vacuo. Reference compound 3 as isolated as clear oil. LC/MS (Expected 257.2 (M+H), found 257.4).

Reference Compound 4

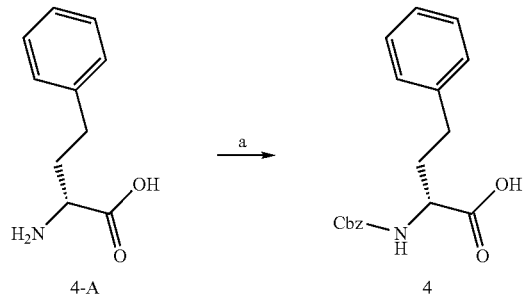

The reagents and conditions for the above reaction are: (a) Cbz-OSu, Et$_3$N, THF, water, 99%.

D-Homophenylalanine 4-A (3.22 g, 18.0 mmol) and N-(Benzyloxycarbonyloxy)-succinimide (Cbz-OSu) (4.49 g, 18.0 mmol) are added to a round bottomed flask containing THF (60 mL) and water (20 mL). The mixture is stirred at room temperature and Et$_3$N (10.1 mL, 72.0 mmol) is added, and the reaction is stirred overnight at room temperature. The clear solution is diluted with EtOAc (200 mL) and washed with 1N HCl (3×100 mL) and brine (1×100 mL), and dried with MgSO$_4$. Solvent is evaporated in vacuo to afford the desired product as a white solid, which is used without further purification.

Reference Compound 5

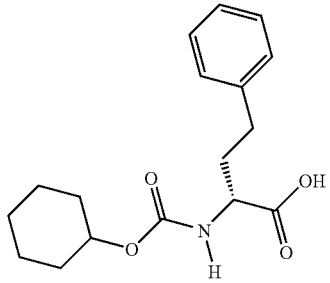

Reference compound 5 is prepared following conditions analogous to those described for Reference compound 4, using cyclohexylcarbonyl-OSu rather than Cbz-OSu.

Reference Compound 6

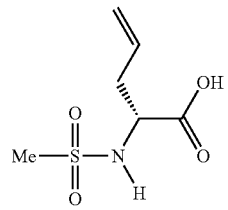

Reference compound 6 is prepared following conditions analogous to those described for Reference compound 1, using D-allylglycine methyl ester hydrochloride.

Reference Compound 7

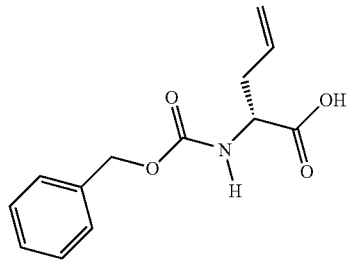

Reference compound 7 is prepared following conditions analogous to those described for Reference compound 4, using D-Allylglycine as a reagent.

Reference Compound 8

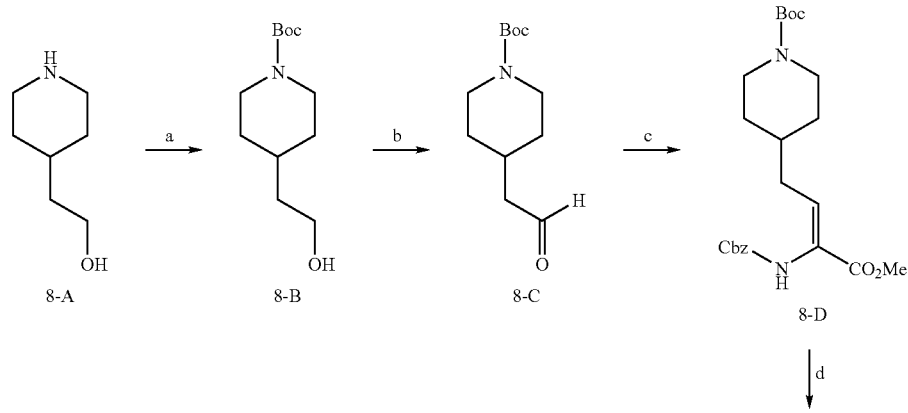

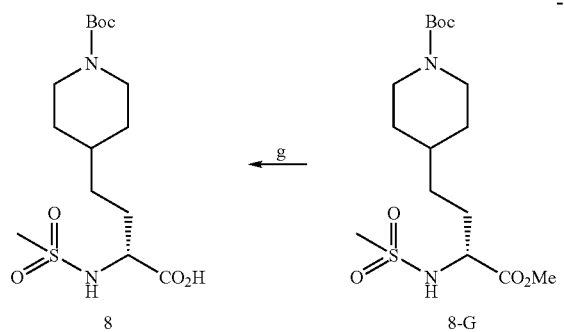
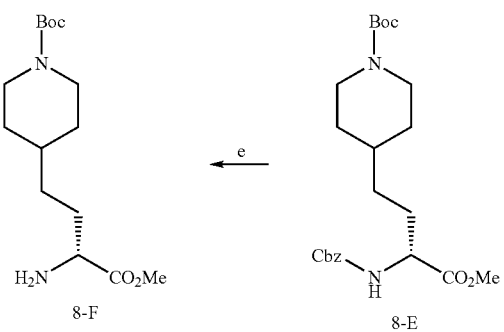

8-B: 4-piperidine ethanol (8-A) (5 g, 39.7 mmol) is dissolved in THF (120 mL). Triethylamine (5.6 mL, 40 mmol) is added and the solution is cooled to 0° C. Boc₂O (9.59 g, 44 mmol) is added and the reaction is stirred overnight at room temperature. Solvent is removed in vacuo, and the crude residue is dissolved in ethyl acetate (120 mL). The solution is washed with 0.1 N HCl (3×100 mL) and brine (1×100 mL); dried with MgSO₄; filtered and solvent evaporated in vacuo to give compound 8-B as a clear oil.

8-C: Trichloroisocyanuric acid (2.66 g, 11.46 mmol) is added to a solution of the alcohol (2.39 g, 10.42 mmol) in CH₂Cl₂, and the solution is stirred and maintained at 0° C., followed by addition of a catalytic amount of TEMPO. After the addition, the mixture is warmed to room temperature and stirred for an hour and then filtered on Celite. The organic phase is washed with saturated aqueous Na₂CO₃, followed by 1N HCl and brine. The organic layer is dried (MgSO₄) and the solvent is evaporated to give compound 8-C. ¹H NMR (CDCl₃, 400 MHz) δ 9.72 (1H, s), 4.07-4.01 (2H, m), 2.70-2.57 (2H, m), 2.35-2.31 (2H, m), 2.05-1.94 (1H, m), 1.64-1.46 (2H, m), 1.39 (9H, s), 1.30-1.02 (2H, m).

8-D: To a solution of Cbz-α-phosphonoglycine trimethyl ester, (2.8 g, 8.45 mmol) in THF at −78° C. is added 1,1,3,3-tetramethyl-guanidine (1.022 ml, 8.14 mmol). After 10 minutes, the aldehyde 8-C (1.76 g, 7.76 mmol) is added. The solution is then placed in an ice bath at 0° C. for 1 hour, and then allowed to warm to room temperature and stirred one more hour. The solution is diluted with EtOAc, washed with 1M NaHSO₄, dried (MgSO₄) and concentrated in vacuo. The residue is purified by automated silica gel chromatography with EtOAc/hexanes (0-100%) to afford 8-D as a clear oil. MS m/z 333.2 (M+1), ¹H NMR (CDCl3, 400 MHz) δ. 7.35-7.33 (5H, m), 6.63 (1H, t, J=8 Hz), 6.30 (1H, bs), 5.12 (2H, s), 4.10-4.04 (2H, m), 3.73 (3H, s), 2.67-2.62 (2H, m), 2.14 (2H, t, J=6.8 Hz), 1.63-1.46 (3H, m), 1.43 (9H, s), 1.14-1.06 (2H, m).

8-E: A Parr vessel is charged with 8-D (1 g, 2.31 mmol) and MeOH (100 ml) under nitrogen. The solution is subjected to three cycles of vacuum and nitrogen bubbling and the catalyst (R,R)-Ethyl-DuPHOS-Rh(COD) triflate is added (30 mg, 0.04 mmol). The mixture is placed under 60 psi of hydrogen gas at room temperature for 24 h. The conversion to 8-E is complete after 24 h with >99% e.e., the solvent is removed in vacuo, and the crude product is purified by silica gel chromatography (hexanes/EtOAc).

8-F: Intermediate 8-E is dissolved in MeOH, the solution is flushed with nitrogen, and Pd/Carbon (5% wt, Degussa) is added. The mixture is placed under 50 psi of hydrogen gas at room temperature and shaken for 24 h. The mixture is flushed with nitrogen and filtered through Celite. The cake is washed with MeOH, and the combined organic solution is concentrated under vacuum. Hexanes is added and then evaporated to azeotrope the remaining methanol to afford 8-F as an oil, which is then used in the next step without further purification.

8-G: Crude intermediate 8-F (0.6 g, 1.99 mmol) is dissolved in THF (10 mL), and 2,4,6-collidine (315 mg, 2.38 mmol) and methanesulfonyl chloride (0.170 ml, 2.19 mmol) are added to the solution and stirred for 2 hours. The reaction is diluted with EtOAc (50 mL), and the solution is washed with 1M NaHSO₄ (2×25 mL) and brine (25 mL), and dried (MgSO₄). The solvent is removed in vacuo and the crude residue purified by flash chromatography using a gradient of hexanes and EtOAc to afford the desired product 8-G.

Reference compound 8: Compound 8-G (0.70 g, 1.84 mmol) is dissolved in dioxane (7 mL), and LiOH.H₂O (232 mg, 5.55 mmol) dissolved in water (4 mL) is added. The reaction mixture is stirred for 1 h at 23° C. The solvent is evaporated; and the residue is diluted with EtOAc (25 mL) and washed with 1N NaHSO₄ (25 mL) and brine (25 mL), dried over MgSO₄ and filtered. The solvent is removed in vacuo and the crude purified by silica gel chromatography (Hexanes/EtOAc gradient) to afford the desired product Reference compound 8 as a white solid.

Reference Compound 9

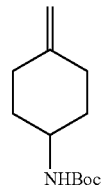

Reference compound 9 is prepared by olefination of corresponding cyclohexanone. A solution of methyltriphenylphosphonium bromide (156 mg, 0.44 mmol) and KHMDS (880 µL of 0.5M solution in toluene, 0.44 mmol) in THF (10 mL) at 23° C. is allowed to stir for 1 hour. A THF solution of 4-N-Boc-amino-1-cyclohexanone (75 mg, 0.35 mmol) in 5 mL of THF is added and the reaction is stirred at 23° C. until complete as indicated by LC/MS. The reaction is quenched with water; THF is evaporated and redissolved in EtOAc and the layers are separated. The aqueous phase is washed with 2×10 mL EtOAc and the combined organic layers are washed with water, saturated NaCl, dried over MgSO₄ and filtered. The solvent is removed in vacuo and the crude purified by silica gel chromatography (Hexanes/EtOAc gradient) to afford the desired product Reference compound 9 as a clear oil. LC/MS found 212.3 [M+H].

Reference Compound 10

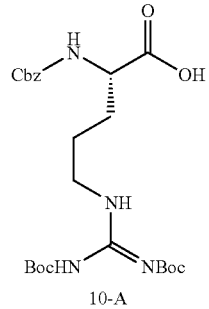
10-A a ⟶

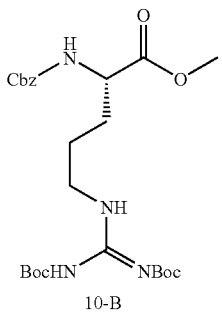
10-B b ⟶

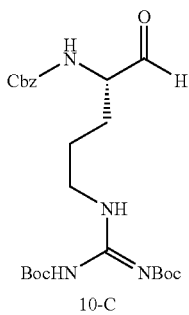
10-C c ⟶

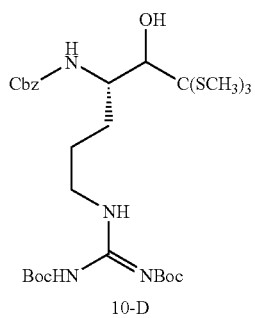
10-D d ⟶

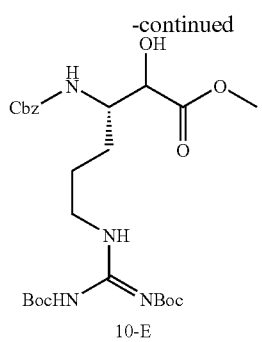
10-E e ⟶

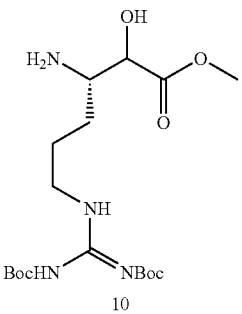
10

In the reaction scheme above, the reagents and conditions are: (a) TBTU/CH$_2$Cl$_2$/CH$_3$OH, Et$_3$N, 23° C.; (b) DIBAL-H, CH$_2$Cl$_2$, −78° C.; (c) n-BuLi, HC(SCH$_3$)$_3$, THF, −65° C.; (d) HgCl$_2$, HgO, MeOH, H$_2$O, 23° C.; (e) H$_2$, MeOH, Pd/C 10%, 23° C., 12 h.

Intermediates 10-B and 10-C are prepared following procedures analogous to those described for Reference compound 2, using N-bis-Boc arginine (10-A) and intermediate 10-B are reagents respectively.

10-D: n-BuLi (6.4 mL of 2.5M in hexanes solution, 15.94 mmol) is added over a period of 10 minutes to a stirring solution of tris(methylthio)methane (2.24 mL, 16.74 mmol) in THF (45 mL) at −65° C. After 20 minutes, a −65° C. solution of aldehyde 10-C (1.83 g, 3.71 mmol) in THF (20 mL) is added over a 30 minute period. The solution is allowed to stir at −65° C. over 5 hours. The reaction mixture is quenched by addition to a 400 mL solution of saturated NH$_4$Cl and CH$_2$Cl$_2$ (1:12). The layers are separated and the aqueous layer is washed with CH$_2$Cl$_2$ (3×100 mL). The combined organic layers are washed with H$_2$O, brine, dried over MgSO4, filtered, and evaporated to dryness. Automated silica gel chromatography 0-10% EtOAc in CH$_2$Cl$_2$ provides 10-D as a clear oil. LC/MS found 647.3 [M+H].

10-E: To a solution of 10-D (1.0 g, 1.55 mmol) dissolved in MeOH (30 mL) and H$_2$O (2.2 mL) is added mercury(II) chloride (1.42 g, 5.23 mmol) and mercury(II) oxide (422 mg, 1.95 mmol) under vigorous stirring at 23° C. for 72 hours. The reaction mixture is filtered over Celite, and the residue is washed with CH$_2$Cl$_2$ (75 mL), MeOH (10 mL), and water (10 mL). The filtrate is separated, and the aqueous layer is extracted with CH$_2$Cl$_2$ (50 mL). The combined organic layers are washed with saturated aqueous NH$_4$OAc (3×50 mL) and saturated aqueous NH$_4$Cl (2×75 mL), dried over Na$_2$SO$_4$, filtered and evaporated to provide crude 10-E. Automated silica gel chromatography 0-100% EtOAc in hexanes provides 10-E as a clear oil. LC/MS found 553.3 [M+H].

Reference compound 10 is prepared following conditions analogous to those described for Reference compound 2, using intermediate 10-E as a reagent.

EXAMPLE 1
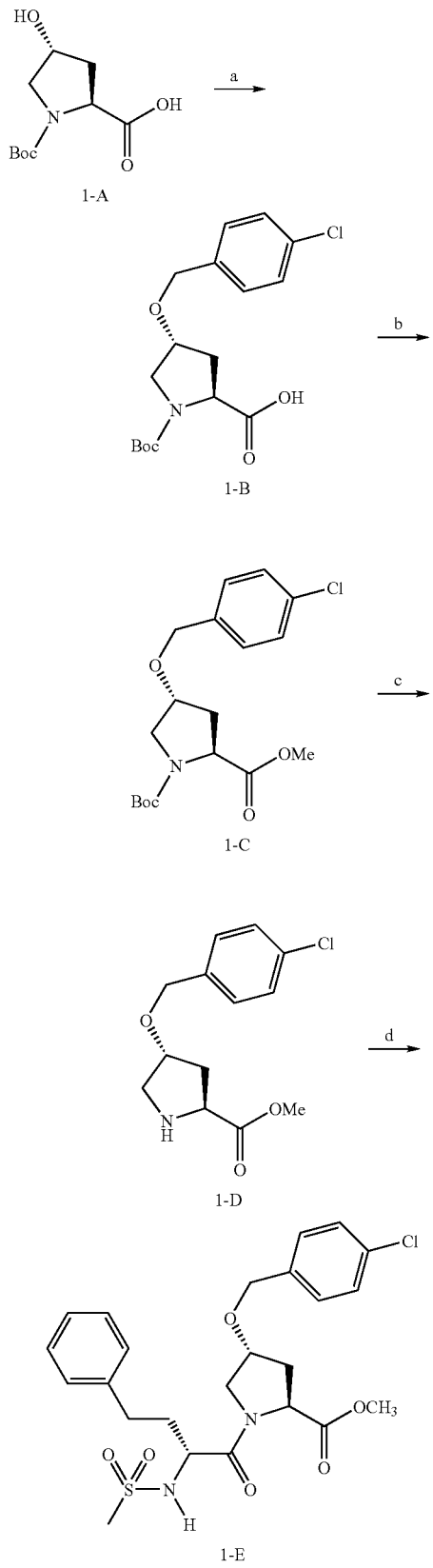
1-A
1-B
1-C
1-D
1-E
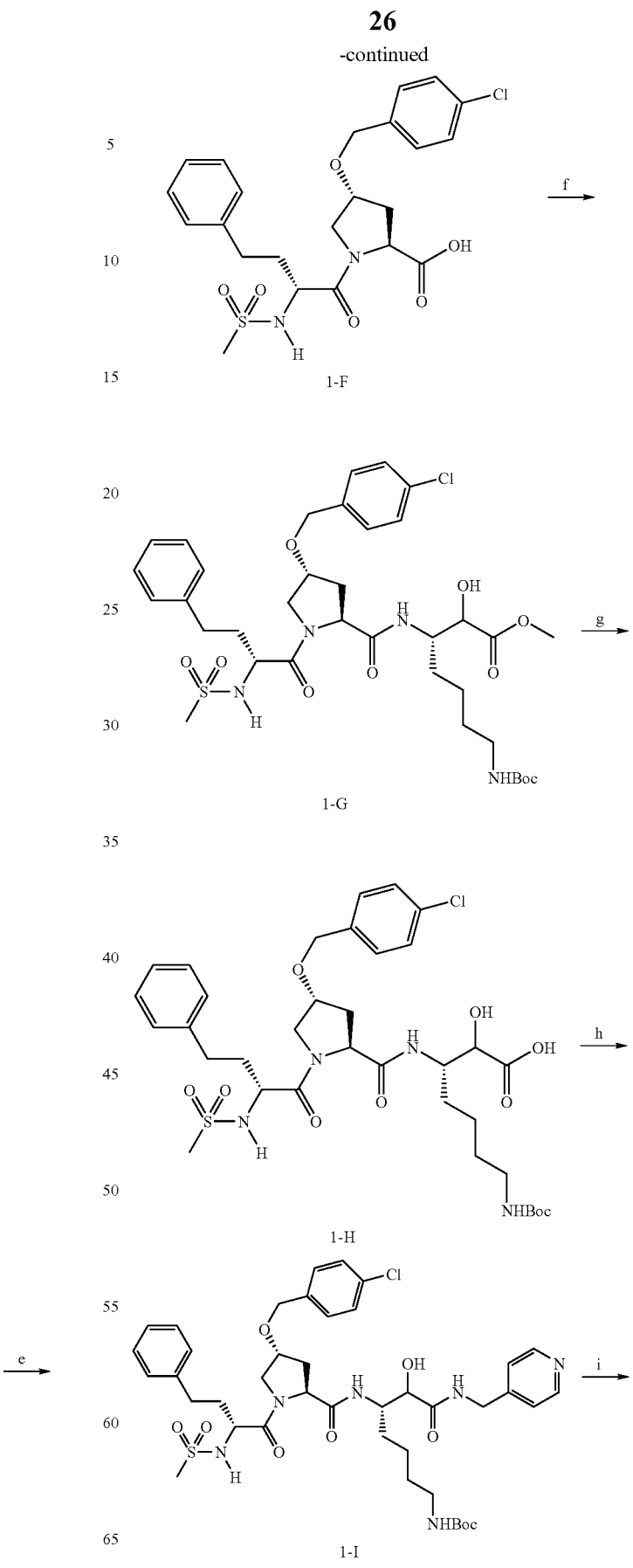
1-F
1-G
1-H
1-I

-continued

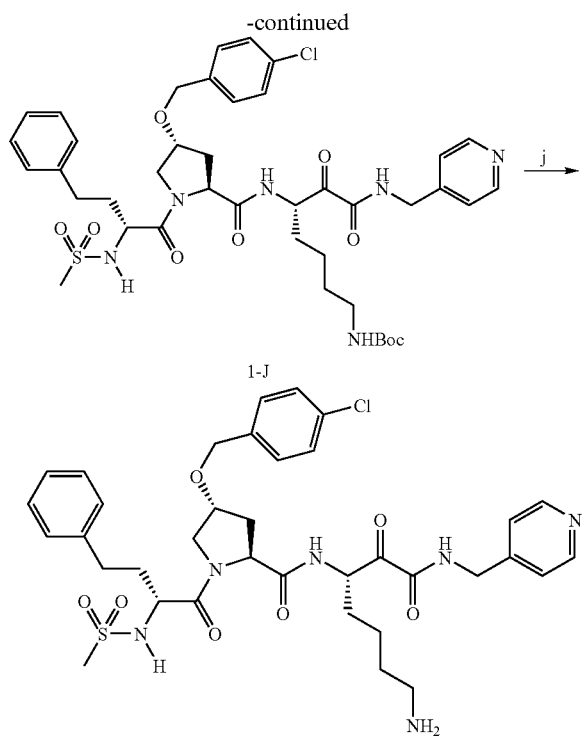

Example 1

In Example 1, the reagents and conditions are: (a) KOH, 4-Chlorobenzyl chloride, DMSO, 0° C. to 23° C.; (b) TMS-CHN$_2$, CH$_2$Cl$_2$/MeOH, 23° C.; (c) TFA/CH$_2$Cl$_2$ (50:50), 23° C. (d) HATU/DIPEA/CH$_2$Cl$_2$, Reference compound 1, 23° C. (e) LiOH, dioxanes/water (4:1), 23° C. (f) HATU/DIPEA/CH$_2$Cl$_2$, Reference compound 2, 23° C. (g) LiOH, dioxanes/water (4:1), 23° C. (h) HATU/DIPEA/CH$_2$Cl$_2$, 4-Aminomethyl pyridine, 23° C. (h) Dess-Martin Periodinane, CH$_2$Cl$_2$, 23° C. (j) TFA/CH$_2$Cl$_2$ (20:80), 23° C. followed by mass-directed HPLC purification, 23° C.

1-B: Finely powdered KOH (19.4 g, 0.346 mol) is dissolved in DMSO and stirred at room temperature for 20 min and then cooled to 0° C. N-Boc-trans-4-hydroxy-L-proline (Boc-Hyp-OH, 1-A) (10 g, 43.3 mmol) is dissolved in DMSO (10 mL) and added, and the reaction mixture is stirred for an additional 10 min at 0° C. Next, 4-chlorobenzyl chloride (33 g, 0.204 mol) is added, and the reaction mixture is stirred at 0° C. for an additional 15 min, after which point the ice bath is removed and the reaction mixture is allowed to warm to room temperature and stirred for 4 h. The reaction mixture is poured into water (300 mL), and the reaction vessel is rinsed with an additional aliquot of water (300 mL). The combined aqueous layer is extracted with ether (2×300 mL) and discarded. The aqueous layer is acidified with 87% H$_3$PO$_4$ to pH 2.3 and then extracted with ether (3×300 mL). The combined ether extracts are washed with water (2×400 mL) and brine (2×400 mL), and then dried over MgSO$_4$, filtered and concentrated in-vacuo. The residue is purified by chromatography on silica gel with EtOAc/Hexanes (gradient 0 to 100%) to yield the compound 1-B as clear oil. MS m/z 256.1 (M+1-Boc); $^1$H NMR (DMSO-D$_6$, 400 MHz) δ 7.39-7.31 (4H, m), 4.52-4.40 (2H, m), 4.16-4.10 (2H, m), 3.48-3.41 (2H, m), 2.40-2.30 (1H, m), 2.03-1.94 (1H, m), 1.39-1.34 (9H, m).

1-C: A solution of (trimethylsilyl)diazomethane (2M in diethylether) (4.7 ml, 9.45 mmol) is added to carboxylic acid 1-B (2.4 g, 8.6 mmol) dissolved in CH$_2$Cl$_2$/MeOH 5:1 (25 mL) at room temperature. When the starting material had been consumed as determined by LC/MS, the reaction mixture is quenched with acetic acid, concentrated in-vacuo, and the crude residue is purified by flash chromatography (gradient EtOAc:Hexanes) to afford the methyl ester 1-C as a clear oil.

1-D: A round bottomed flask is charged with a stirbar and 1-C (1.03 g, 2.80 mmol). TFA (50%) in CH$_2$Cl$_2$ (6 mL) is added, and the solution is stirred for 1 h at room temperature. The solvent is removed in-vacuo, hexanes is added and then evaporated again in vacuo to dryness, and repeated if necessary to azeotrope remaining TFA. The crude material is used directly in the next step without further purification.

1-E: The crude material 1-D is dissolved in CH$_2$Cl$_2$ (30 mL), Reference compound 1 (1.02 g, 2.80 mmol) and HATU (1.12 g, 2.94 mmol) are added and the solution is stirred at room temperature for 10 min. DIPEA (1.5 mL, 8.4 mmol) is added via syringe and the reaction mixture is allowed to stir overnight at room temperature. The solvent is removed in-vacuo, and the crude material is directly purified by flash chromatography (40 g silica, hexanes/EtOAc gradient). The solvent is removed in-vacuo to afford 1-E as an oily semisolid.

1-F: Methyl ester 1-E (1.15 g, 1.86 mmol) is dissolved in dioxane (15 mL). Lithium hydroxide monohydrate (120 mg, 2.00 mmol) is dissolved in water (15 mL) and added dropwise to the solution of methyl ester 1-E, and allowed to stir for 3 h at room temperature. The reaction mixture is concentrated in vacuo to remove dioxane and then acidified with 1M NaHSO$_4$. This is extracted with EtOAc, and the combined organic layer is washed with brine and dried with MgSO$_4$. The solvent is removed in-vacuo to afford carboxylic acid 1-F as a waxy solid.

1-G: Carboxylic acid 1-F (385 mg, 0.78 mmol) is dissolved in CH$_2$Cl$_2$ (10 mL). Reference compound 2 (151 mg, 0.52 mmol) and HATU (356 mg, 0.94 mmol) are added, and the mixture is stirred for 10 min at room temperature. DIPEA (0.27 mL, 1.56 mmol) is added via syringe, and the reaction mixture is left to stir for 3 hours at room temperature. The solvent is removed in-vacuo, the crude is redissolved in EtOAc (50 mL) and washed with 1M HCl (2×25 mL), followed by saturated aqueous NaHCO$_3$ (2×25 mL), and brine (25 mL), and dried with anhydrous Na$_2$SO$_4$. The solvent is removed in-vacuo, and the crude material is directly purified by flash chromatography (40 g silica, CH$_2$Cl$_2$/MeOH gradient). The solvent is removed in-vacuo to afford 1-G as an oily semisolid.

1-H: Methyl ester 1-G (300 mg, 0.39 mmol) is dissolved in dioxane (18 mL). Lithium hydroxide (12 mg, 0.47 mmol) is dissolved in water (7.5 mL) and added dropwise to the solution of methyl ester 1-G, and allowed to stir for 3 h at room temperature. The reaction mixture is concentrated in vacuo to remove dioxane and then acidified with 1M NaHSO$_4$. This is extracted with EtOAc, and the combined organic layer is washed with brine and dried with MgSO$_4$. The solvent is removed in-vacuo to afford carboxylic acid 1-H as a waxy solid.

1-I: Carboxylic acid 1-H (72 mg, 0.10 mmol) is dissolved in CH$_2$Cl$_2$ (2 mL). 4-Aminomethyl pyridine (13 mg, 0.11 mmol) and HATU (54 mg, 0.14 mmol) are added, and the mixture is stirred for 10 min at room temperature. DIPEA (50 μL, 0.29 mmol) is added via syringe, and the reaction mixture is left to stir for 3 hours at room temperature. The solvent is removed in-vacuo, the crude material is redissolved in EtOAc (50 mL) and washed with 1M HCl (2×25 mL), followed by saturated aqueous NaHCO$_3$ (2×25 mL), and brine (25 mL), and dried with anhydrous Na$_2$SO$_4$. The solvent is removed in-vacuo, and the crude material 1-I is used directly in the next reaction.

1-J: Crude alcohol 1-I (80 mg, 0.10 mmol) is dissolved in CH$_2$Cl$_2$ (2 mL) and Dess-Martin periodinane (65 mg, 0.15 mmol) is added. The reaction mixture is stirred for 2 hours at room temperature. The solvent is removed in-vacuo, the crude is redissolved in EtOAc (50 mL) and washed with saturated Na$_2$S$_2$O$_3$ (2×25 mL), followed by saturated aqueous NaHCO$_3$ (2×25 mL) and brine (25 mL), and dried with anhydrous Na$_2$SO$_4$. The crude material is purified by flash chromatography (40 g silica column) using a gradient of CH$_2$Cl$_2$:MeOH to afford the ketone 1-J as a white foam.

Example 1: Intermediate 1-J (42 mg, 0.05 mmol) is dissolved in 20% TFA in CH$_2$Cl$_2$ (3 mL). The reaction is stirred at room temperature for 2 h and the solvent is removed in vacuo. The crude material is purified by reverse-phase HPLC and the solvent is lyophilized to afford 1 as a white powder as its mono-TFA salt.

EXAMPLES 2-9

Examples 2-7 are synthesized using methods analogous to those described for the synthesis of Example 1, using appropriate reagents in step h:

Example 2, using methylamine;
Example 3, using benzylamine;
Example 4, using phenethylamine;
Example 5, using aniline;
Example 6, using cyclopropylmethyl amine; and
Example 7, using cyclohexylmethyl amine.

Examples 8 and 9 are prepared following methods analogous to those described for Example 1, using Reference compound 1 and Reference Compound 3 as reagents. For step (h), phenethylamine and 3-phenylpropylamine were used in Examples 8 and 9, respectively.

EXAMPLE 10

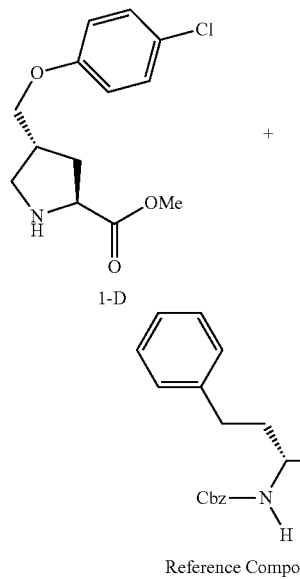
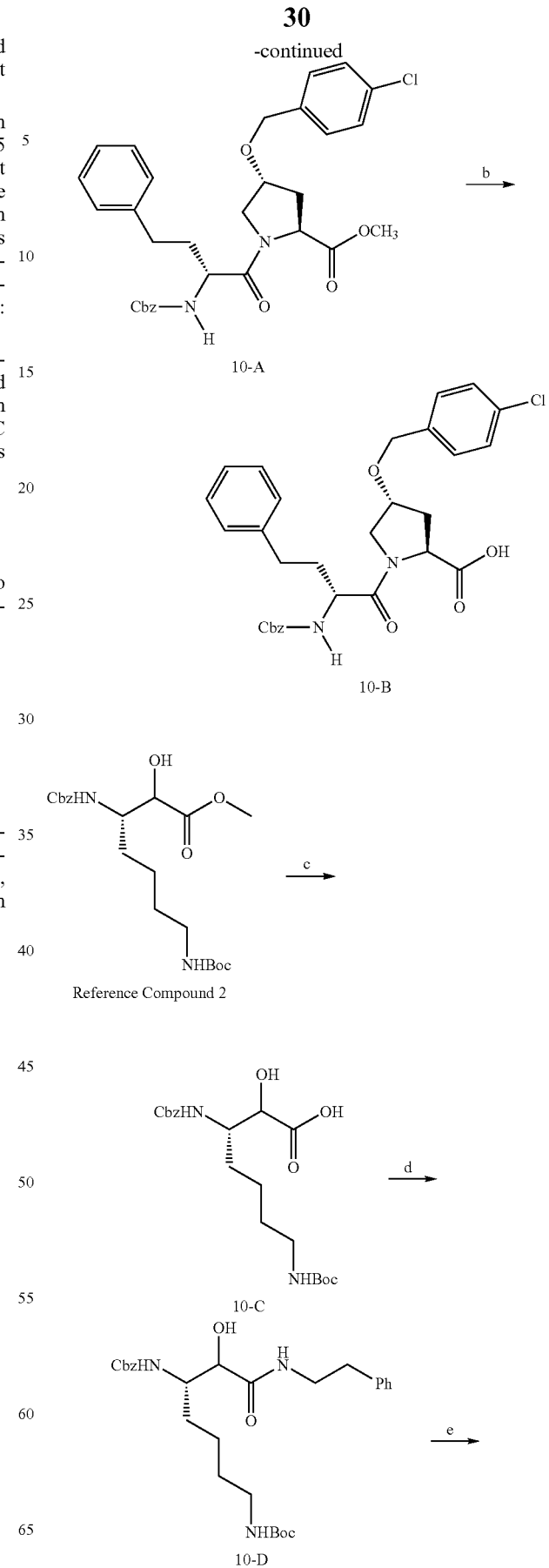

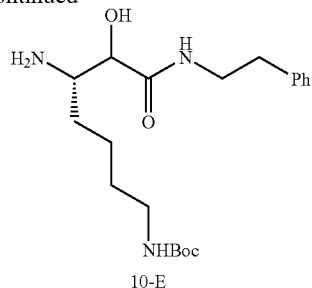

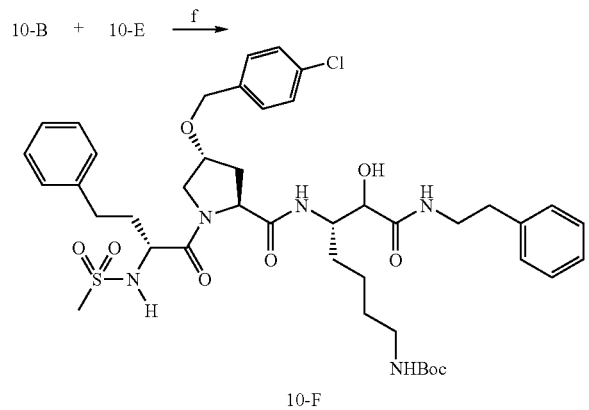

In Example 10, the reagents and conditions are: (a) HATUJ/DIPEA/CH$_2$Cl$_2$, Reference compound 2, 23° C.; (b) LiOH, dioxanes/water (4:1), 23° C.; (c) LiOH, dioxanes/water (4:1), 23° C.; (d) HATU/DIPEA/CH$_2$Cl$_2$, phenethylamine, 23° C.; (e) H$_2$, Pd/C, EtOH, 23° C.; (f) HATU/DIPEA/CH$_2$Cl$_2$, 23° C.

Intermediates 10-A to 10-D are prepared following methods analogous to those for Example 1 steps (d), (e), (g) and (h), using Reference compound 4, 10-A and 10-B as reagents for steps (d), (e) and (g), respectively. In step (h), intermediate 10-C is used as the acid component and phenethylamine as the amine component.

Intermediate 10-E is prepared following methods analogous to those for Example 2, step f, using 10-D as the deprotection substrate. Intermediate 10-F is prepared following methods analogous to those for Example 1 step h, using 10-B as the acid component and intermediate 10-E as the amine component. Dess-Martin oxidation and Boc-deprotection are identical to Example 1 steps (i) and (j).

EXAMPLES 11-12

Examples 11 and 12 are prepared following methods analogous to those described for Example 10, using Reference compound 5 and Reference compound 6 as the acid component, respectively.

EXAMPLE 13

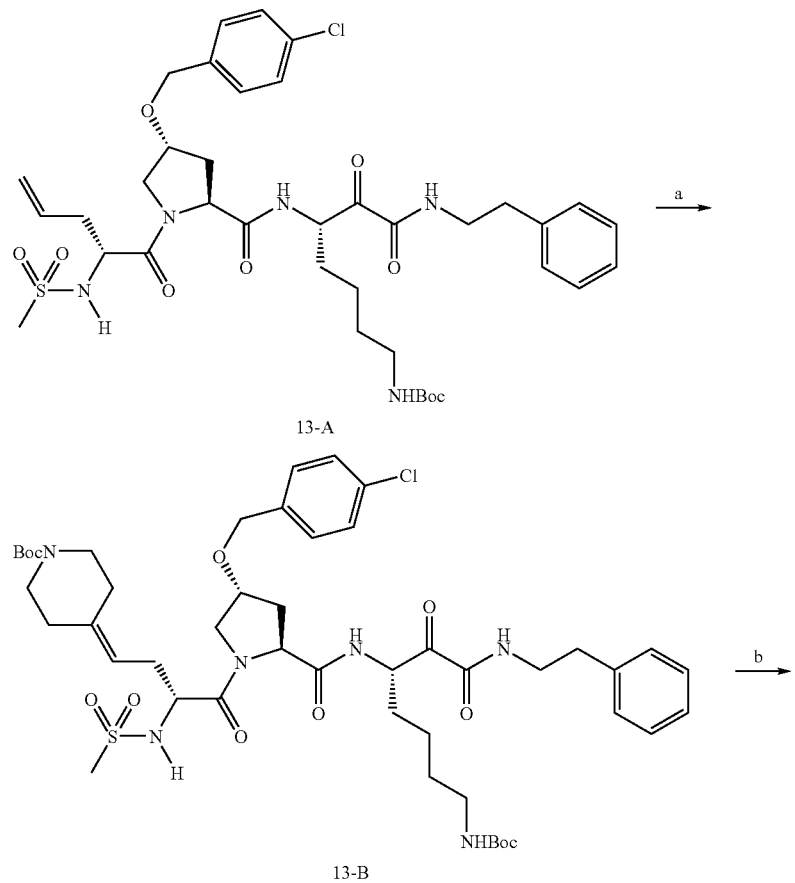

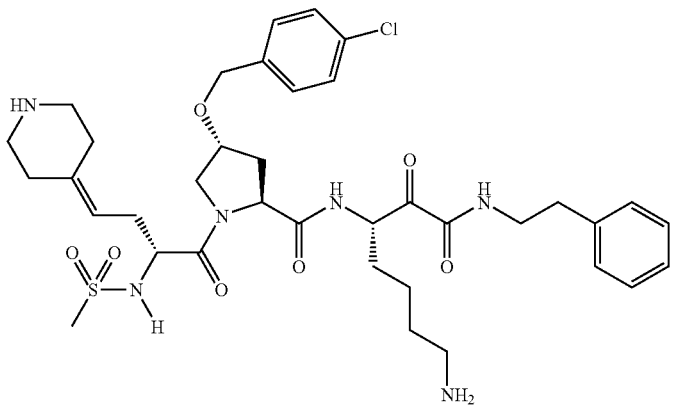

Example 13

In Example 13, the reagents and conditions are: (a) Hoveyda-Grubbs metathesis catalyst, 4-Methylene-N-Boc-piperidine, 13-A, CH$_2$Cl$_2$, 40° C.; 65%; (b) TFA:CH$_2$Cl$_2$ (1:1), 23° C., HPLC purification, 30%.

13-A: This compound is made as an intermediate in the synthetic route for Example 12. The synthesis of 13-A is analogous to Example 1 step (i).

13-B: Anhydrous dichloromethane (5 mL) is added via syringe to 13-A (108 mg, 0.137 mmol, 1.0 eq.), Hoveyda-Grubbs second generation metathesis catalyst [1,3-Bis-(2,4,6-trimethylphenyl)-2-imidazolidinylidene) dichloro (o-isopropoxyphenylmethylene) ruthenium II dichloride] (10 mg, 0.013 mmol, 10 mol %) under a nitrogen atmosphere. N-Boc-4-methylenepiperidine (100 μL, 0.507 mmol, 3.5 eq.) is added via syringe and the reaction is fitted with a reflux condenser and heated to 40° C. for 12 hours. After the reaction is judged as complete by LC/MS, the reaction mixture is directly purified by automated silica-gel purification (80-100% ethyl acetate in hexanes) to provide 13-B as a dark green oil. MS m/z 859.5 (M-Boc+1).

Example 13: This compound is prepared following methods analogous to those for Example 1 step (j), using intermediate 13-B as a reagent.

EXAMPLE 14-57

Examples 14-19, 22-25, 29-30 are prepared following methods analogous to those described for Example 1, using appropriate amine components in step (h), for example, using (R)-methylbenzylamine, (S)-methylbenzylamine and 2-aminomethyl benzothiazole in Examples 14-16, respectively.

Example 20-21, 27-28, 45 and 52 are prepared using methods analogous to those described for preparing Example 13, using appropriate olefin cross-metathesis partners in step (a), for example:

Example 20, using tert-butylethylene;

Example 21, using 4-vinylanisole;

Example 27, using the corresponding intermediate from Example 26;

Example 28, using the corresponding intermediate from Example 26, where phenethylamine is replaced with p-methoxy phenethylamine;

Example 45, using Reference compound 9; and

Example 52, using 4-methylene cyclohexene.

Example 26 is prepared following methods analogous to those for preparing Example 10, using Reference compound 7 as the acid component in step (b).

Examples 31-44 and 46-are prepared following methods analogous to those for preparing Example 1, using appropriate acid components in step (d) and appropriate amine components in steps (f) and (h).

Example 47 is prepared using methods analogous to those described for the preparation of Example 26, except for the amine component in step (d).

Examples 48-51 and 53-54 are prepared following methods analogous to those described for Example 1, using Reference compound 10 and the appropriate amine component in steps (f) and (h), respectively.

Examples 55 and 56 are prepared following methods analogous to those described for Example 1, except for performing steps (i) and (j) directly on intermediates 1-H and 1-G, respectively.

Example 57 is prepared using methods analogous to those described for Example 1, using Reference compound 3 as a reagent.

Examples 58-60 are prepared using methods analogous to those described for Example 1, using the appropriate acid component in step (d) and appropriate amine components in steps (f) and (h).

Table 1 shows compounds of Formula (1), as described in Examples 1-60.

TABLE 1

| Compound | Structure | Physical Data MS (m/z), Elemental Analysis, and ¹H NMR 400 MHz (DMSO-d$_6$) |
|---|---|---|
| 1 | 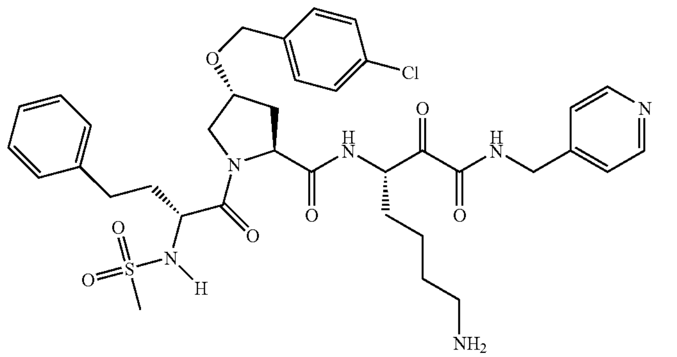 | MS m/z 741.3 (M + 1) |
| 2 | 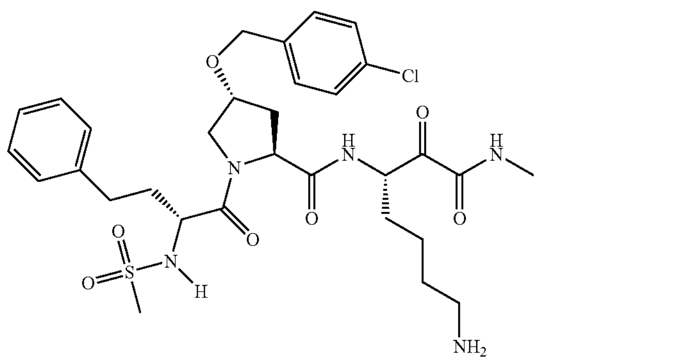 | MS m/z 664.3 (M + 1) |
| 3 | 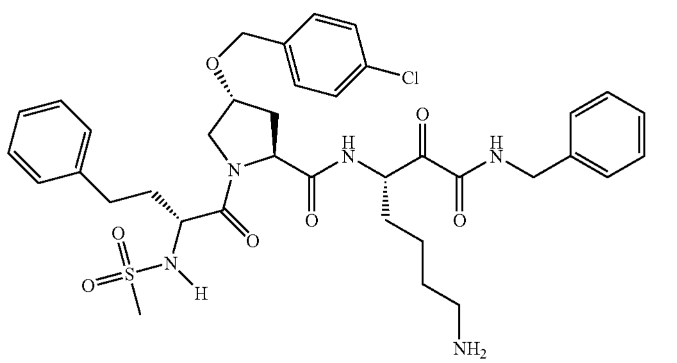 | MS m/z 740.4 (M + 1) |
| 4 | 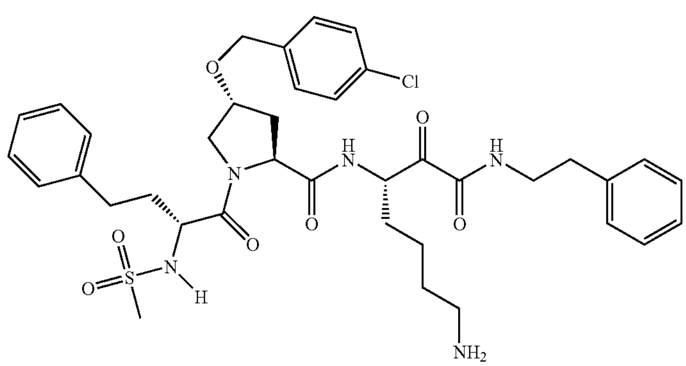 | MS m/z 754.5 (M + 1) |

TABLE 1-continued

| Compound | Structure | Physical Data MS (m/z), Elemental Analysis, and ¹H NMR 400 MHz (DMSO-$d_6$) |
|---|---|---|
| 5 | 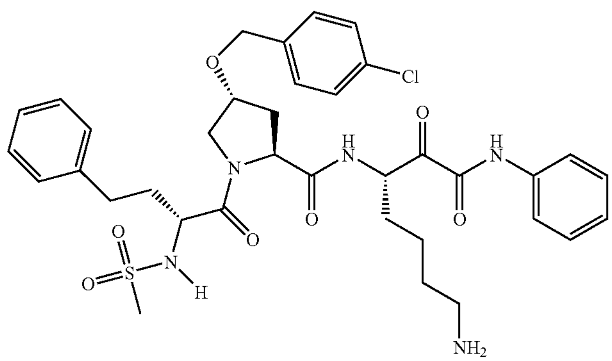 | MS m/z 726.4 (M + 1) |
| 6 | 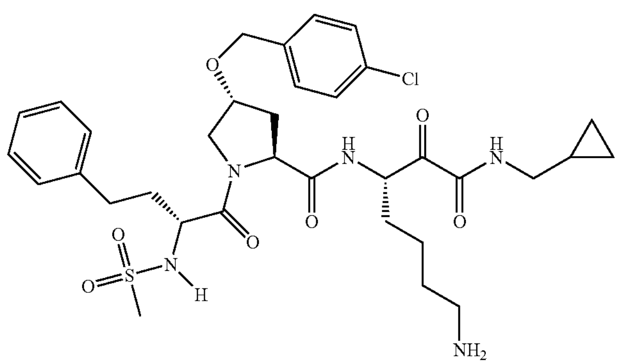 | MS m/z 704.4 (M + 1) |
| 7 | 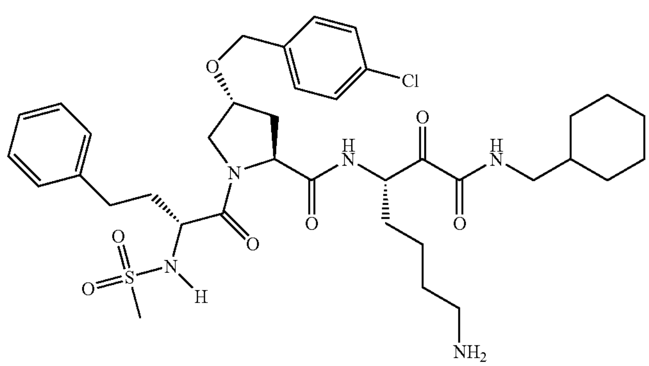 | MS m/z 746.4 (M + 1) |
| 8 | 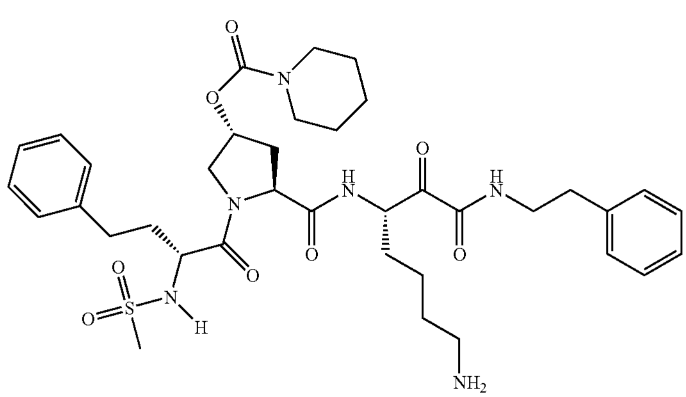 | MS m/z 741.5 (M + 1) |

TABLE 1-continued

| Compound | Structure | Physical Data MS (m/z), Elemental Analysis, and $^1$H NMR 400 MHz (DMSO-d$_6$) |
|---|---|---|
| 9 | 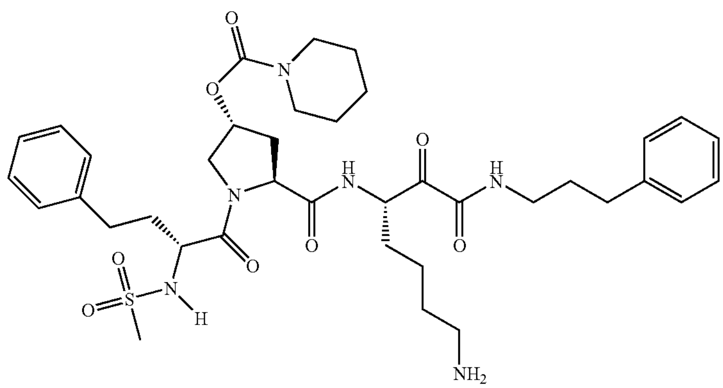 | MS m/z 755.4 (M + 1) |
| 10 | 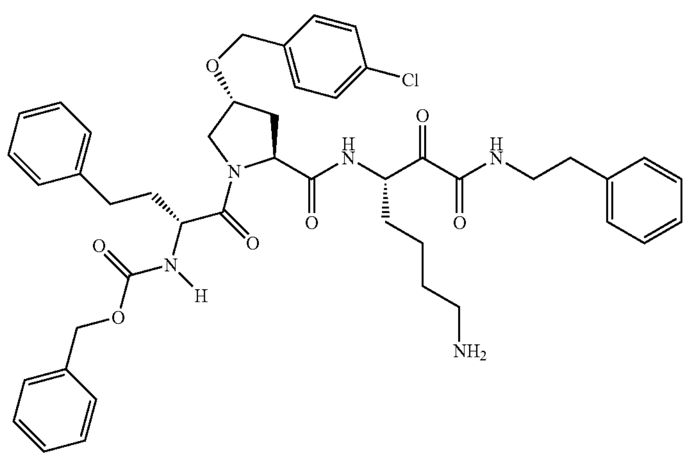 | MS m/z 810.4 (M + 1) |
| 11 | 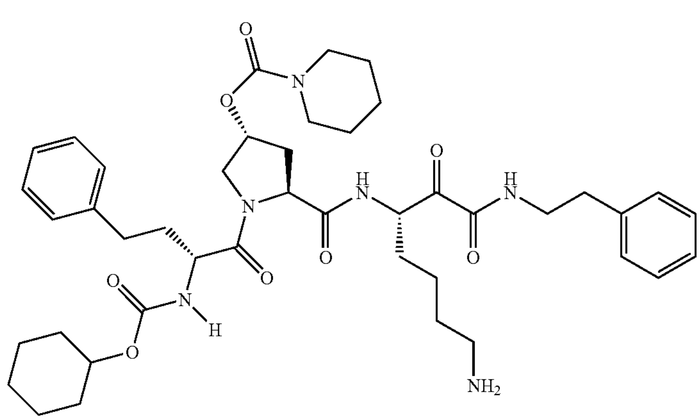 | MS m/z 789.5 (M + 1) |

TABLE 1-continued

| Compound | Structure | Physical Data MS (m/z), Elemental Analysis, and ¹H NMR 400 MHz (DMSO-d₆) |
|---|---|---|
| 12 | 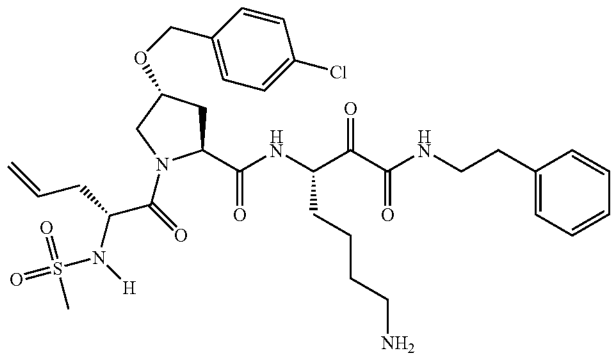 | MS m/z 690.3 (M + 1) |
| 13 | 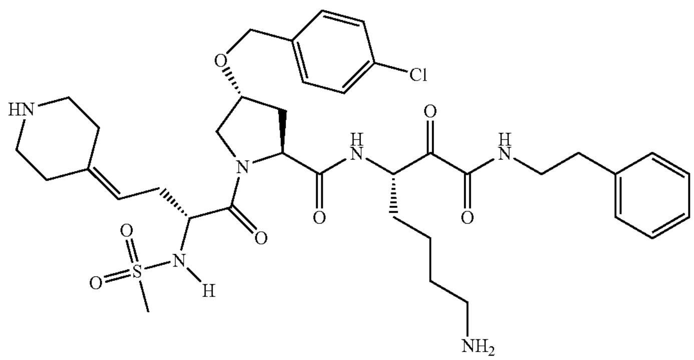 | MS m/z 759.5 (M + 1) |
| 14 | 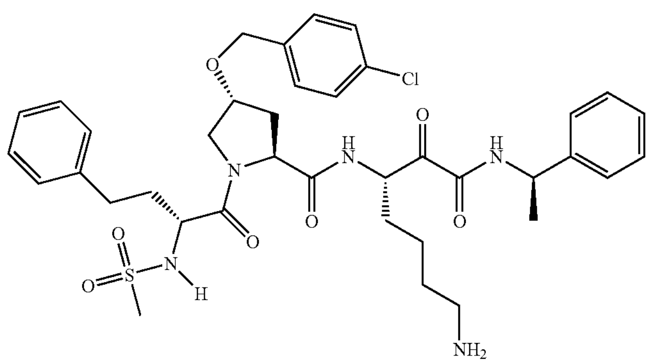 | MS m/z 754.4 (M + 1) |
| 15 | 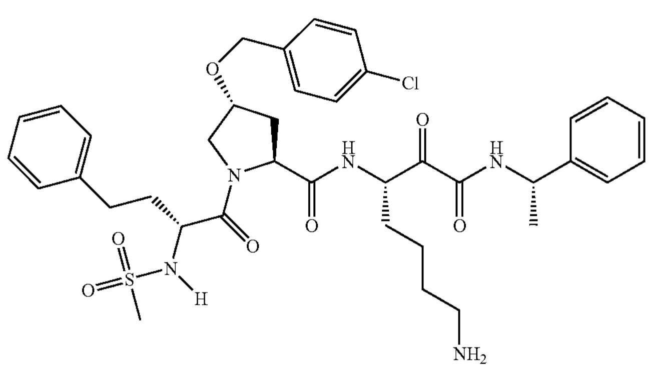 | MS m/z 754.4 (M + 1) |

TABLE 1-continued

| Compound | Structure | Physical Data MS (m/z), Elemental Analysis, and $^1$H NMR 400 MHz (DMSO-$d_6$) |
|---|---|---|
| 16 | 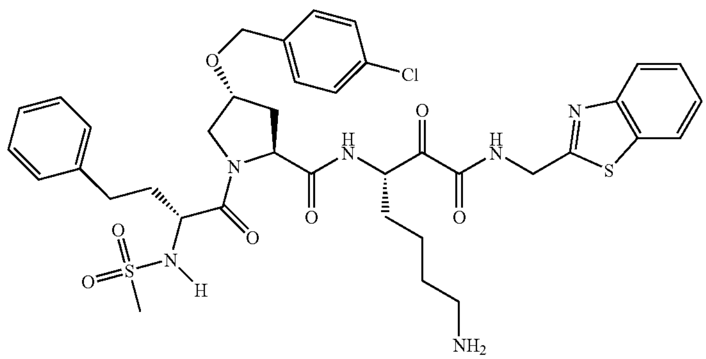 | MS m/z 797.3 (M + 1) |
| 17 | 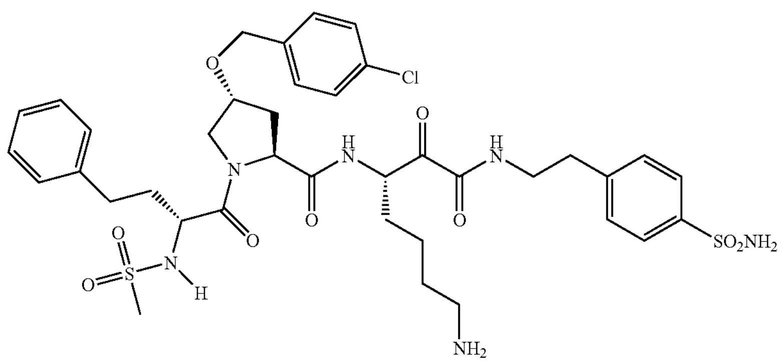 | MS m/z 833.3 (M + 1) |
| 18 | 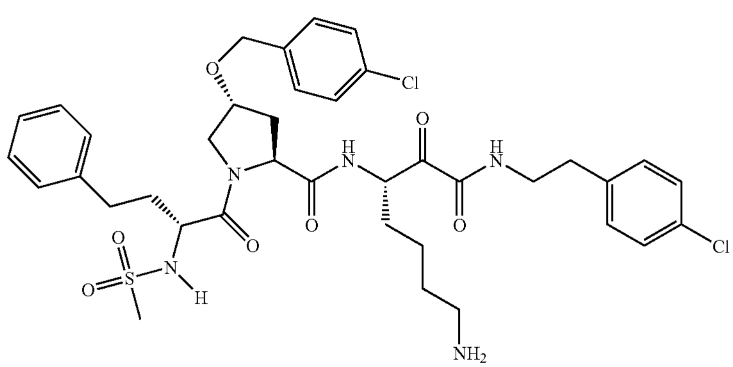 | MS m/z 788.4 (M + 1) |
| 19 | 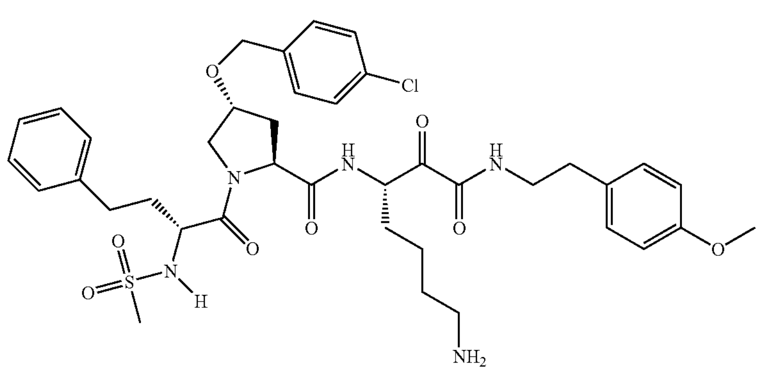 | MS m/z 784.4 (M + 1) |

TABLE 1-continued

| Compound | Structure | Physical Data MS (m/z), Elemental Analysis, and $^1$H NMR 400 MHz (DMSO-$d_6$) |
|---|---|---|
| 20 | 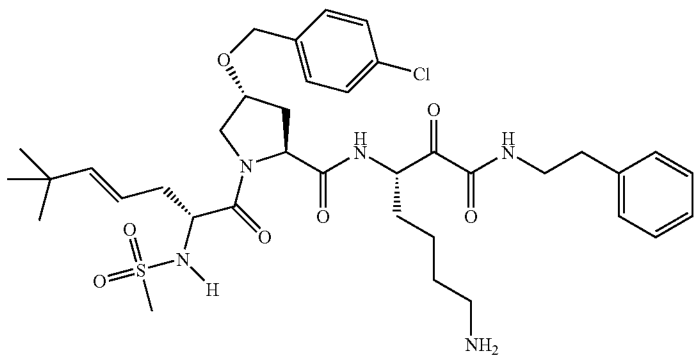 | MS m/z 746.5 (M + 1) |
| 21 | 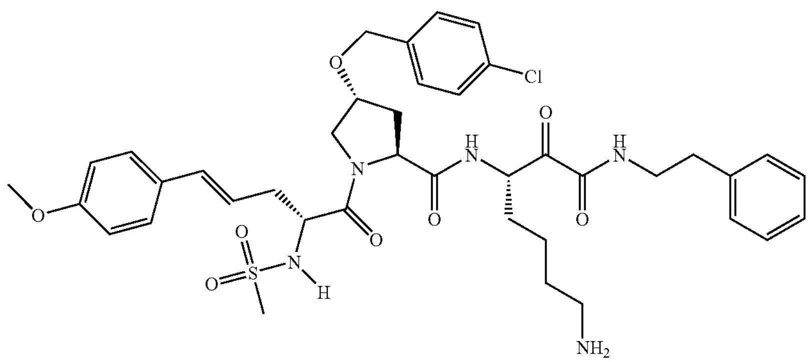 | MS m/z 796.3 (M + 1) |
| 22 | 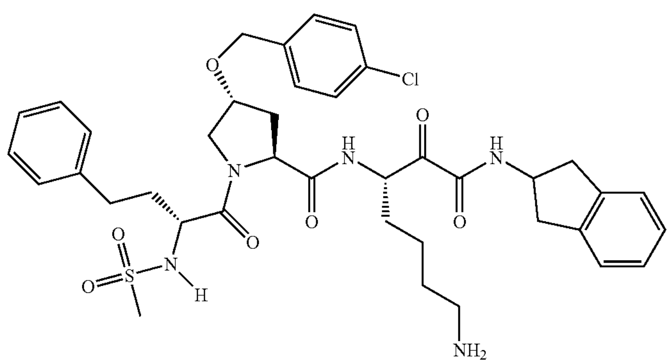 | MS m/z 766.3 (M + 1) |
| 23 | 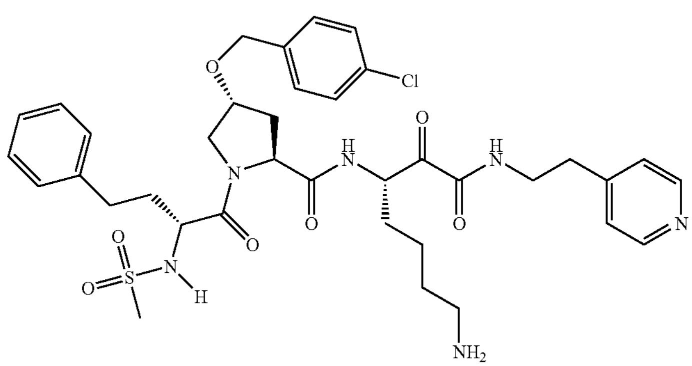 | MS m/z 755.6 (M + 1) |

TABLE 1-continued

| Compound | Structure | Physical Data MS (m/z), Elemental Analysis, and ¹H NMR 400 MHz (DMSO-$d_6$) |
|---|---|---|
| 24 | 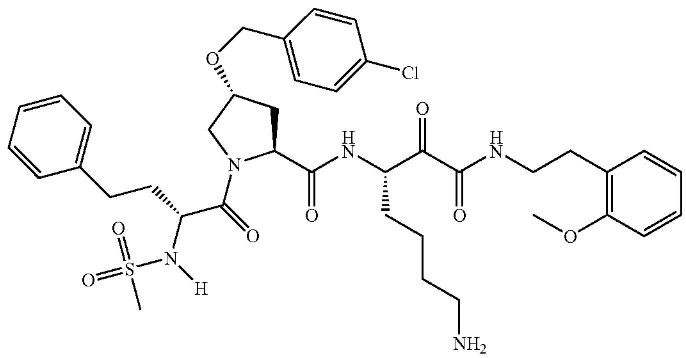 | MS m/z 784.6 (M + 1) |
| 25 | 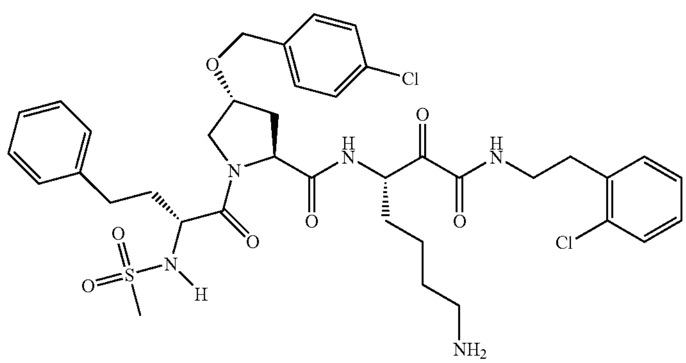 | MS m/z 788.6 (M + 1) |
| 26 | 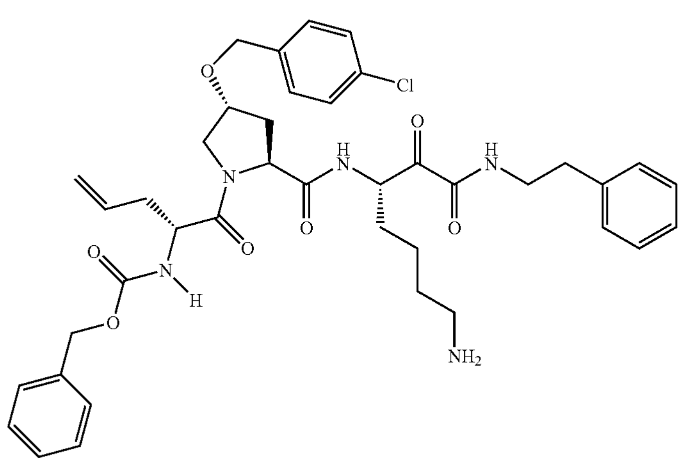 | MS m/z 746.3 (M + 1) |

TABLE 1-continued

| Compound | Structure | Physical Data MS (m/z), Elemental Analysis, and ¹H NMR 400 MHz (DMSO-d$_6$) |
|---|---|---|
| 27 | 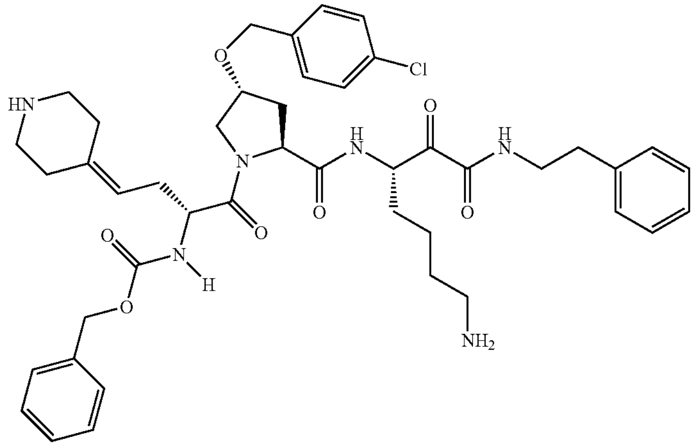 | MS m/z 815.6 (M + 1) |
| 28 | 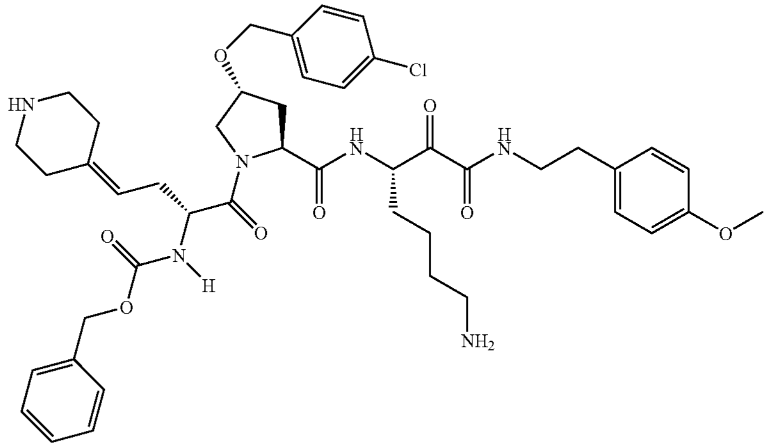 | MS m/z 845.5 (M + 1) |
| 29 | 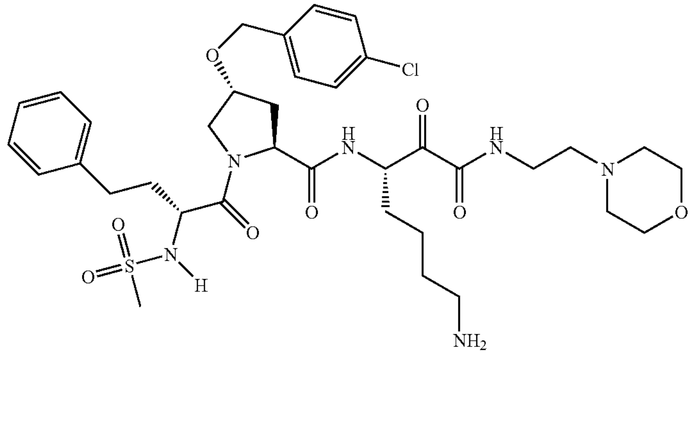 | MS m/z 781.3 (M + H$_2$O + 1) |

TABLE 1-continued

| Compound | Structure | Physical Data MS (m/z), Elemental Analysis, and ¹H NMR 400 MHz (DMSO-d₆) |
|---|---|---|
| 30 | 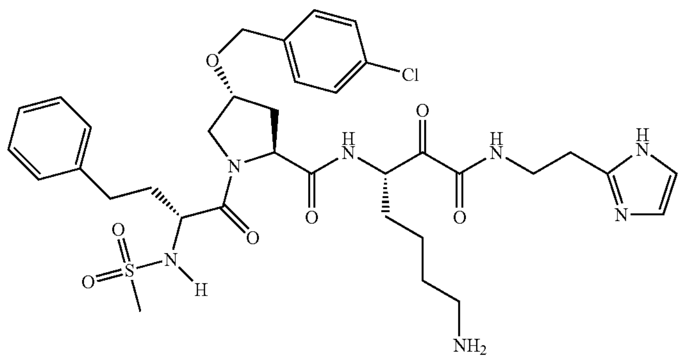 | MS m/z 762.3 (M + H₂O + 1) |
| 31 | 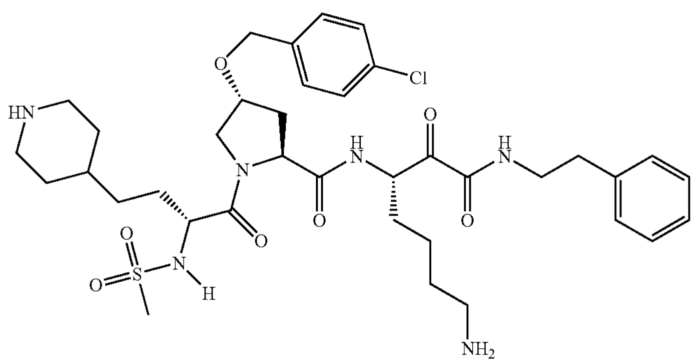 | MS m/z 761.4 (M + 1) |
| 32 | 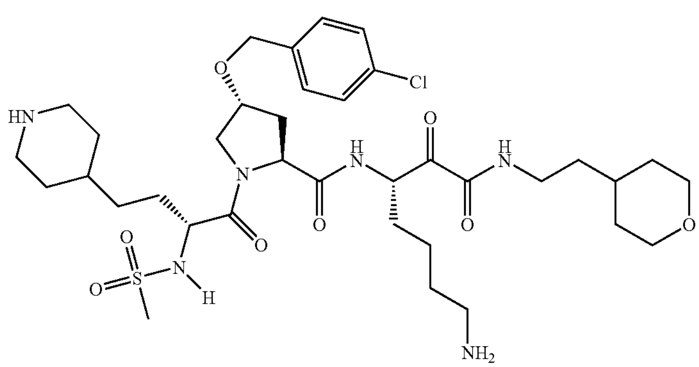 | MS m/z 769.4 (M + 1) |
| 33 | 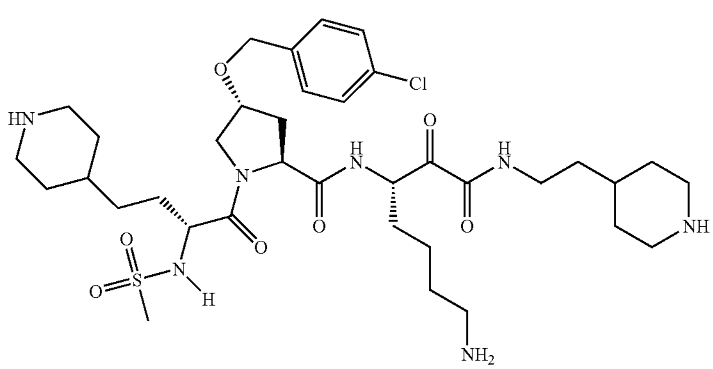 | MS m/z 768.4 (M + 1) |

TABLE 1-continued

| Compound | Structure | Physical Data MS (m/z), Elemental Analysis, and ¹H NMR 400 MHz (DMSO-d$_6$) |
|---|---|---|
| 34 | 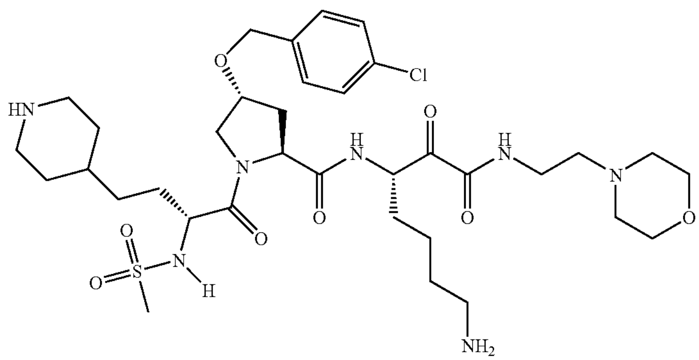 | MS m/z 770.4 (M + 1) |
| 35 | 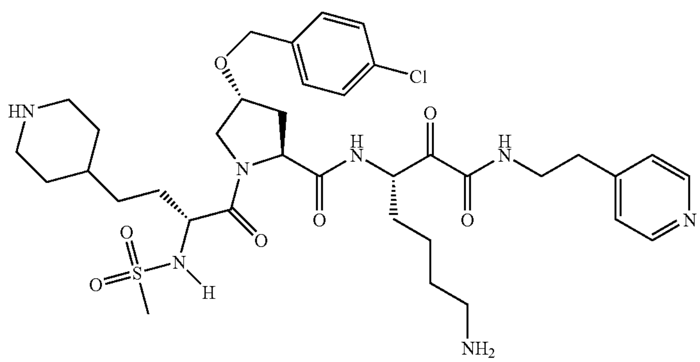 | MS m/z 762.3 (M + 1) |
| 36 | 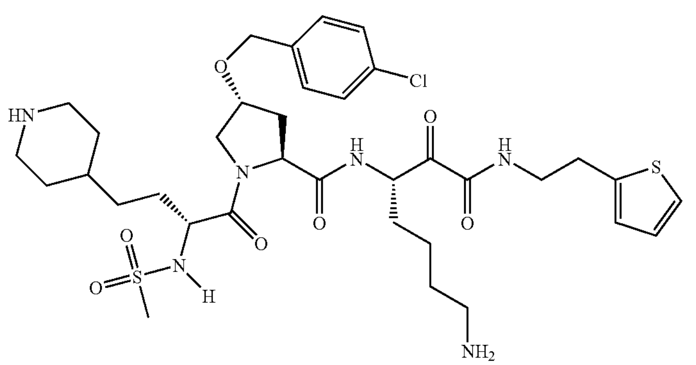 | MS m/z 767.4 (M + 1) |
| 37 | 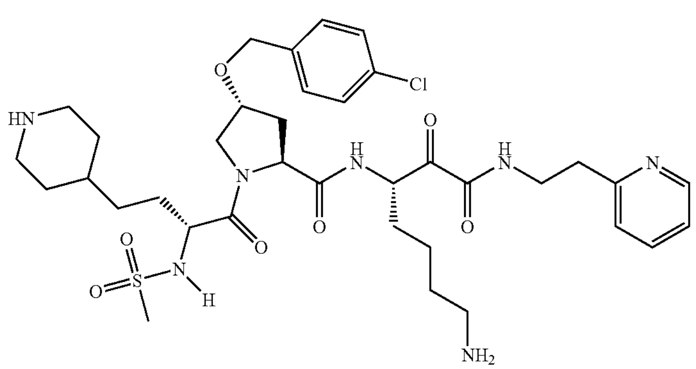 | MS m/z 762.3 (M + 1) |

TABLE 1-continued

| Compound | Structure | Physical Data MS (m/z), Elemental Analysis, and ¹H NMR 400 MHz (DMSO-d$_6$) |
|---|---|---|
| 38 | 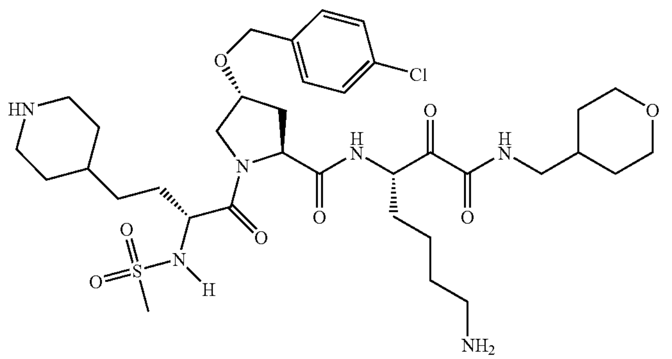 | MS m/z 755.4 (M + 1) |
| 39 | 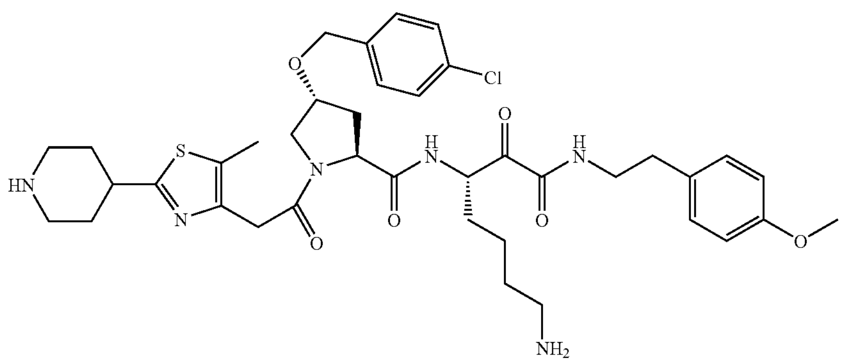 | MS m/z 767.4 (M + 1) |
| 40 | 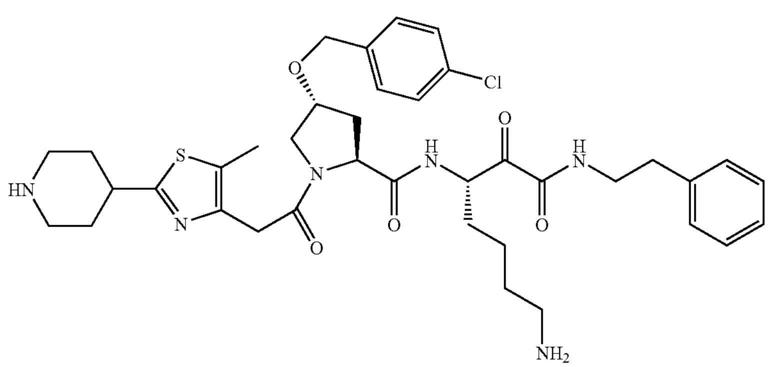 | MS m/z 737.4 (M + 1) |
| 41 | 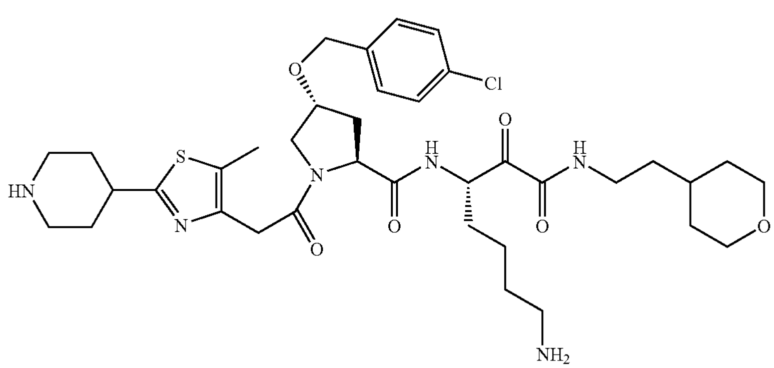 | MS m/z 745.4 (M + 1) |

TABLE 1-continued

| Compound | Structure | Physical Data MS (m/z), Elemental Analysis, and ¹H NMR 400 MHz (DMSO-d₆) |
|---|---|---|
| 42 | 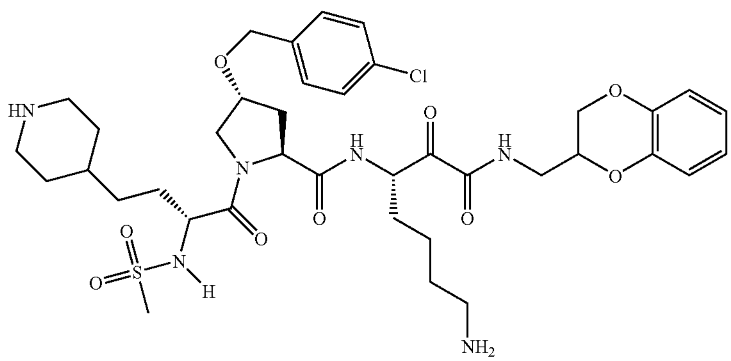 | MS m/z 805.4 (M + 1) |
| 43 | 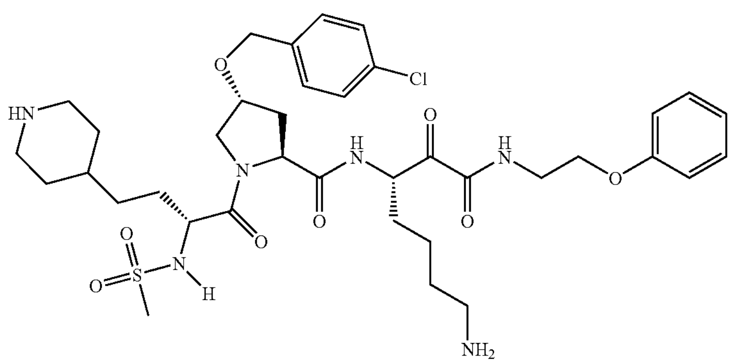 | MS m/z 777.4 (M + 1) |
| 44 | 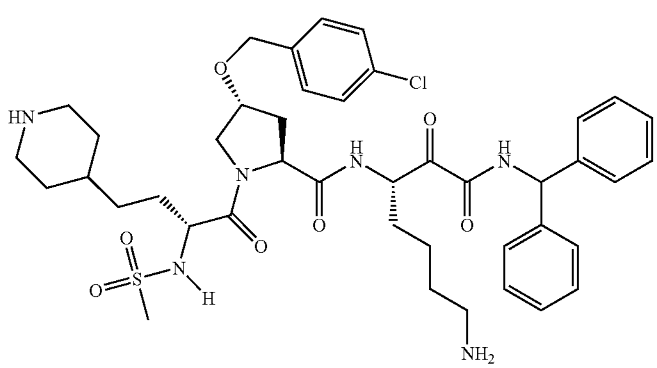 | MS m/z 823.5 (M + 1) |
| 45 | 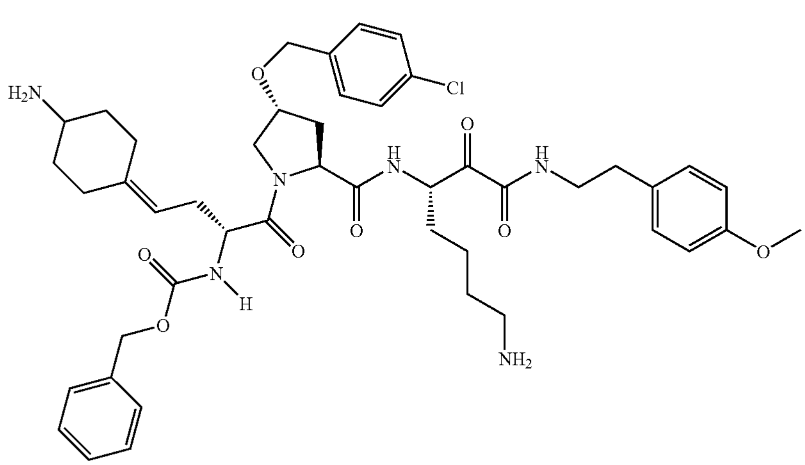 | MS m/z 430.5 (M/2 + 1) |

TABLE 1-continued

| Compound | Structure | Physical Data MS (m/z), Elemental Analysis, and $^1$H NMR 400 MHz (DMSO-d$_6$) |
|---|---|---|
| 46 | 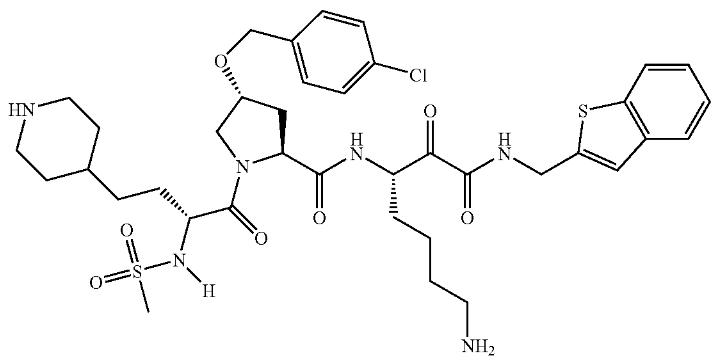 | MS m/z 803.4 (M + 1) |
| 47 | 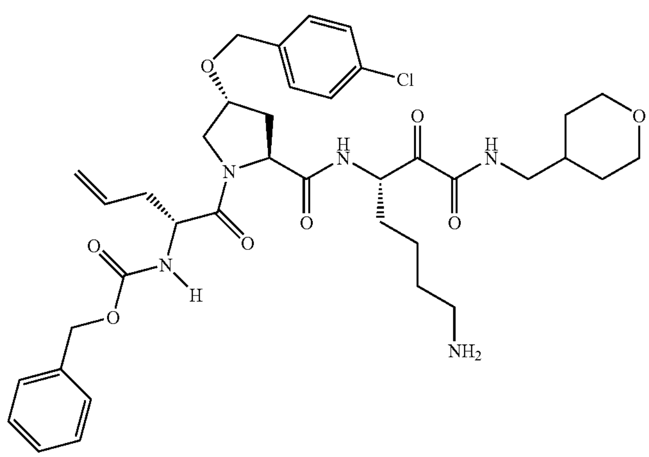 | MS m/z 740.4 (M + 1) |
| 48 | 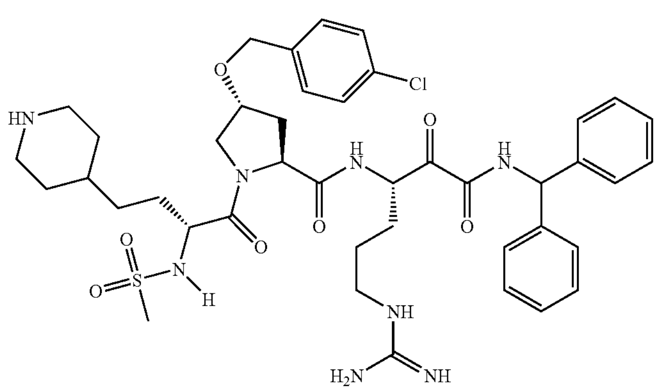 | MS m/z 851.4 (M + 1) |

TABLE 1-continued
| Compound | Structure | Physical Data MS (m/z), Elemental Analysis, and $^1$H NMR 400 MHz (DMSO-$d_6$) |
|---|---|---|
| 49 | 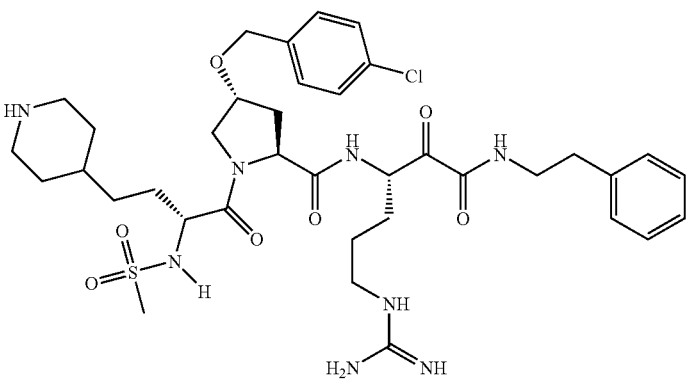 | MS m/z 789.5 (M + 1) |
| 50 | 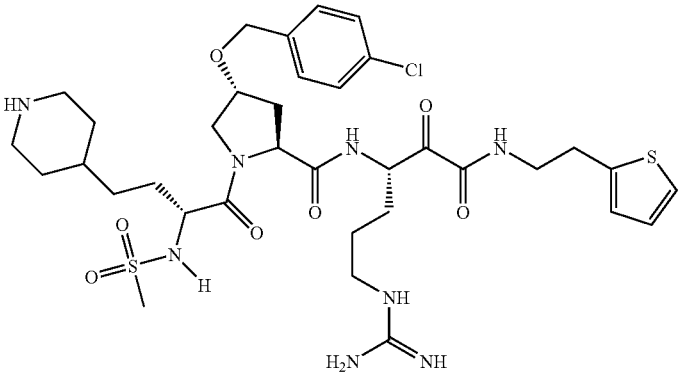 | MS m/z 795.3 (M + 1) |
| 51 | 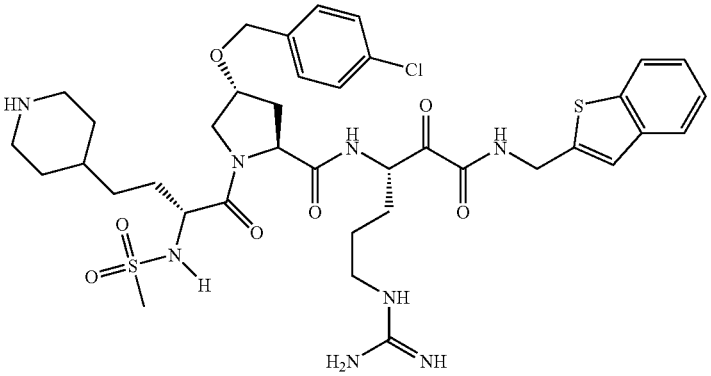 | MS m/z 416.5 (M/2 + 1) |

TABLE 1-continued

| Compound | Structure | Physical Data MS (m/z), Elemental Analysis, and $^1$H NMR 400 MHz (DMSO-$d_6$) |
|---|---|---|
| 52 | 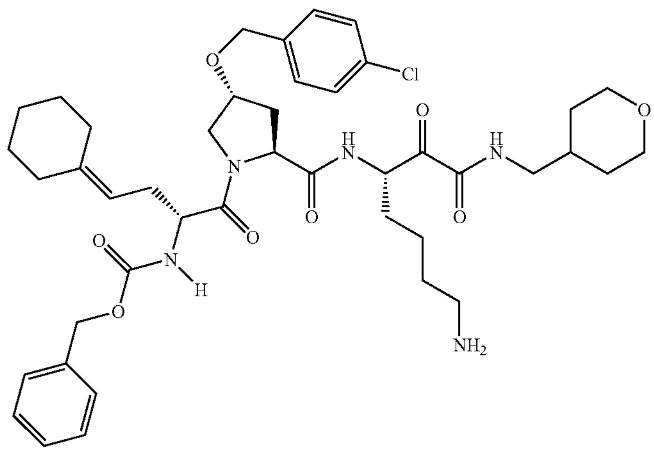 | MS m/z 808.6 (M + 1) |
| 53 | 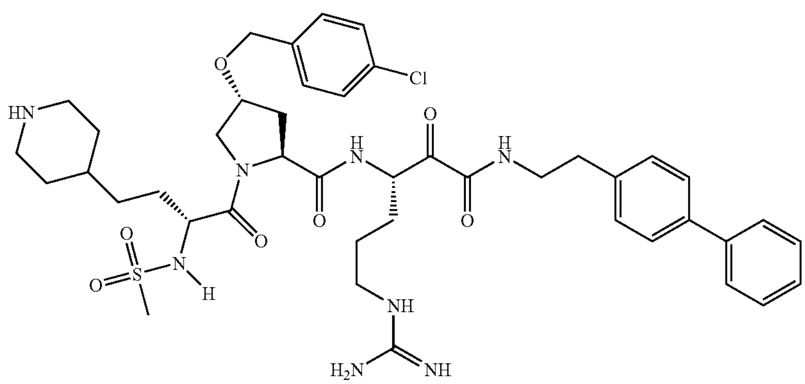 | MS m/z 433.7 (M/2 + 1) |
| 54 | 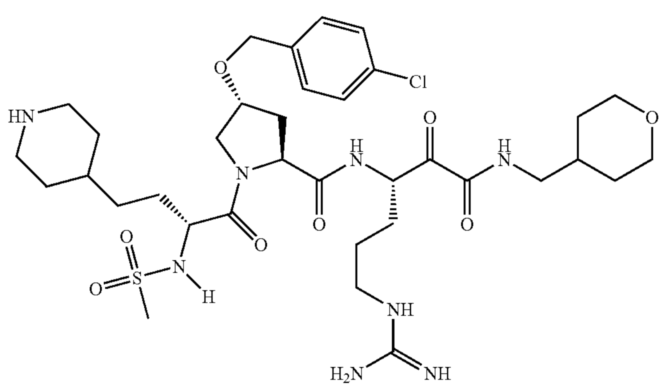 | MS m/z 392.4 (M/2 + 1) |

TABLE 1-continued

| Compound | Structure | Physical Data MS (m/z), Elemental Analysis, and $^1$H NMR 400 MHz (DMSO-$d_6$) |
|---|---|---|
| 55 | 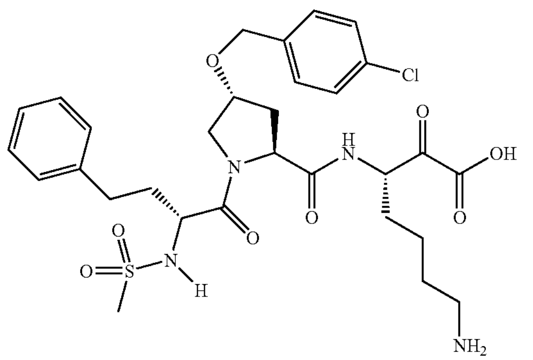 | MS m/z 669.4 (M + H$_2$O + 1) |
| 56 | 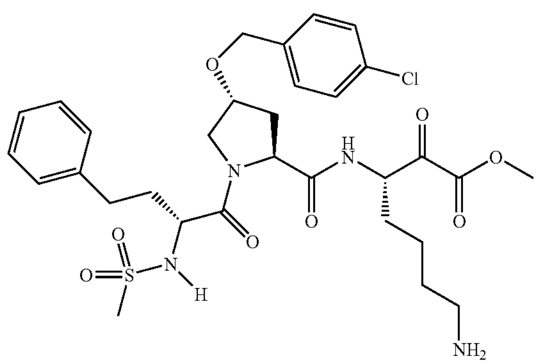 | MS m/z 683.2 (M + H$_2$O + 1) |
| 57 | 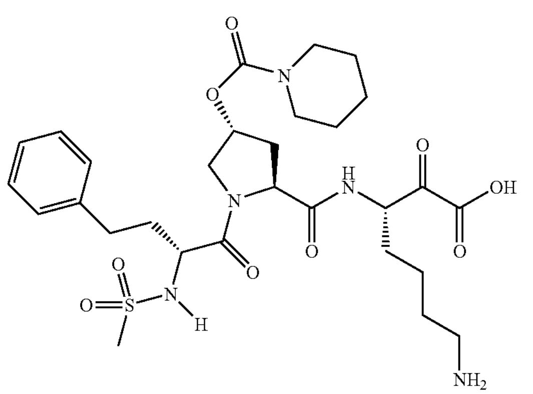 | MS m/z 638.4 (M + 1) |
| 58 | 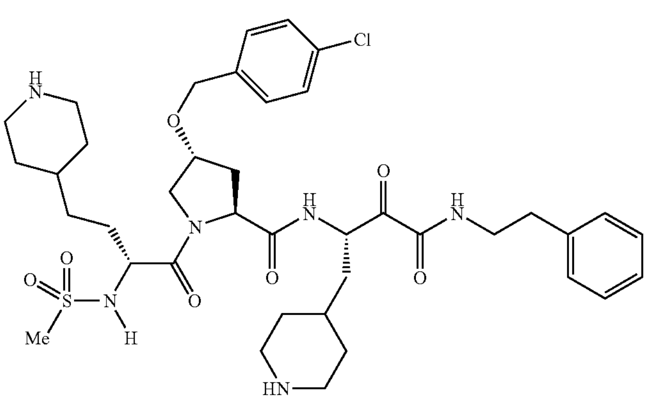 | MS m/z 787.5 (M + 1) |

TABLE 1-continued

| Compound | Structure | Physical Data MS (m/z), Elemental Analysis, and $^1$H NMR 400 MHz (DMSO-$d_6$) |
|---|---|---|
| 59 | 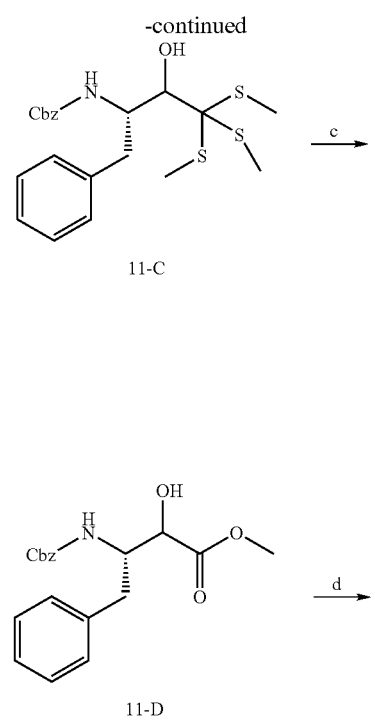 | MS m/z 719.4 (M + 1) |
| 60 | 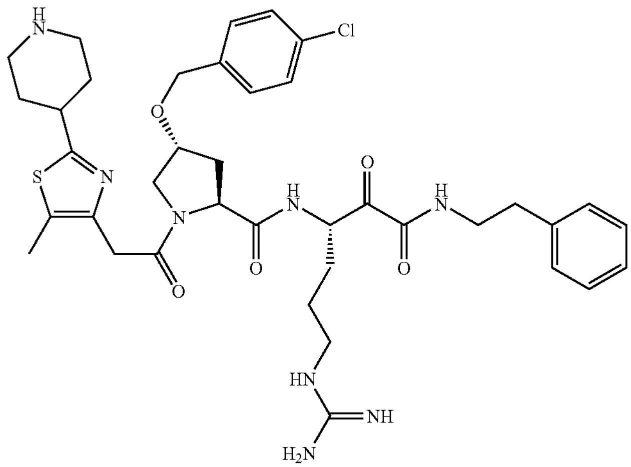 | MS m/z 765.4 (M + 1) |

In another embodiment, the compounds of the invention have Formula (1), wherein $R^1$ is $C_{1-6}$ alkyl or $(CR_2)_m$—X wherein X is $C_{3-7}$ cycloalkyl or aryl, which may be optionally substituted with a non-amino substituent. Representative compounds may be prepared using the following reference compounds and Examples.

Reference Compound 11

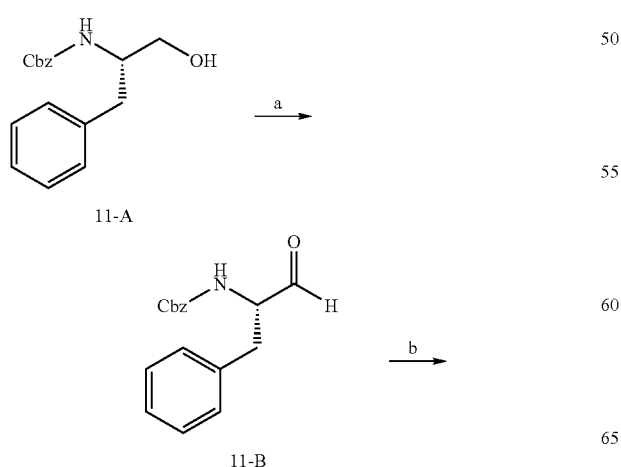

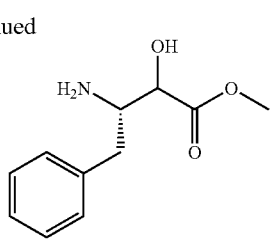

11

In the above reaction scheme for Reference 11, the reagents and conditions are: (a) Trichloroisocyanuric acid, TEMPO, $CH_2Cl_2$, 0° C.; (b) n-BuLi, $HC(SCH_3)_3$, THF, −65° C.; (c) $HgCl_2$, HgO, MeOH, $H_2O$, 23° C.; (d) $H_2$, MeOH, Pd/C 10%, 23° C., 12 h.

11-B: Alcohol 11-A (2.0 g, 7.0 mmol) is dissolved in $CH_2Cl_2$ (15 mL) and the solution is cooled to 0° C. Trichloroisocyanuric acid (1.71 g, 7.36 mmol) is added, followed by TEMPO (11 mg, 0.07 mol). The reaction is then warmed to room temperature and stirred for 15 min at room temperature. A precipitate formed and the reaction mixture is filtered through Celite and washed with $CH_2Cl_2$. The combined $CH_2Cl_2$ solution (~100 mL) is washed with saturated aqueous $NaHCO_3$ (2×50 mL), 1M HCl (2×50 mL), and brine (50 mL), then dried ($MgSO_4$) and solvent evaporated, and used directly in the next step without further purification.

11-C: n-BuLi (7.84 mL of 2.5M in hexanes solution, 19.6 mmol) is added over a period of 10 minutes to a stirring solution of tris(methylthio)methane (2.8 mL, 21.0 mmol) in THF (50 mL) at −65° C. After 20 minutes, a −65° C. solution of aldehyde 11-B (2.0 g, 7.0 mmol) in THF (20 mL) is added over a 30 minute period. The solution is allowed to stir at −65° C. over 5 hours. The reaction mixture is quenched by addition to a 400 mL solution of saturated $NH_4Cl$ and $CH_2Cl_2$ (1:12). The layers are separated and the aqueous layer is washed with $CH_2Cl_2$ (3×100 mL). The combined organic layers are washed with $H_2O$, brine, dried over $MgSO_4$, filtered, and evaporated to dryness. Automated silica gel chromatography 0-10% EtOAc in $CH_2Cl_2$ provides 11-C as a clear oil. LC/MS found 438.1 [M+H].

11-D: To a solution of 11-C (1.23 g, 2.83 mmol) dissolved in MeOH (55 mL) and $H_2O$ (4.0 mL) is added mercury(II) chloride (2.69 g, 9.9 mmol) and mercury(II) oxide (795 mg, 3.67 mmol) under vigorous stirring at 23° C. for 72 hours. The reaction mixture is filtered over Celite, and the residue is washed with $CH_2Cl_2$ (75 mL), MeOH (10 mL), and water (10 mL). The filtrate is separated, and the aqueous layer is extracted with $CH_2Cl_2$ (50 mL). The combined organic layers are washed with saturated aqueous $NH_4OAc$ (3×50 mL) and saturated aqueous $NH_4Cl$ (2×75 mL), dried over $Na_2SO_4$, filtered and evaporated to provide crude 11-D. Automated silica gel chromatography 0-100% EtOAc in hexanes provides 11-D as a clear oil. LC/MS found 344.1 [M+H].

Reference Compound 11: A solution of Compound 11-D (150 mg, 0.44 mmol) is dissolved in methanol (8 mL). 50 mg of Pd/C (10%, wet, Degussa type) is added, and the flask is placed under atmospheric hydrogen pressure. The catalyst is filtered through Celite, and solvent is removed in vacuo. The solvent is removed in vacuo to give Reference compound 11 as clear oil. LC/MS Found 210.2 (M+H).

Reference Compound 12

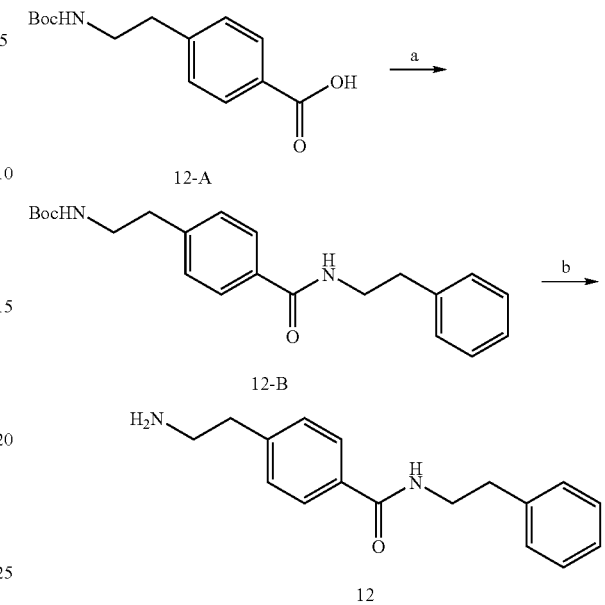

In the above reaction scheme for Reference compound 12, the reagents and conditions are: (a) $HATU/DIPEA/CH_2Cl_2$, Phenethylamine, 23° C.; (b) $TFA/CH_2Cl_2$ (50:50), 23° C.

Carboxylic acid 12-A (250 mg, 0.94 mmol) is dissolved in $CH_2Cl_2$ (5 mL). Phenethylamine (140 mg, 1.13 mmol) and HATU (540 mg, 1.42 mmol) are added, and the mixture is stirred for 10 min at room temperature. DIPEA (0.5 mL, 2.84 mmol) is added via syringe, and the reaction mixture is left to stir for 3 hours at room temperature. The solvent is removed in-vacuo, the crude is redissolved in EtOAc (50 mL) and washed with 1M HCl (2×25 mL), followed by saturated aqueous $NaHCO_3$ (2×25 mL), and brine (25 mL), and dried with anhydrous $Na_2SO_4$. The solvent is removed in-vacuo, and the crude material is directly purified by flash chromatography (40 g silica, 0-30% EtOAc in $CH_2Cl_2$ gradient). The solvent is removed in-vacuo to afford 12-B as an oil. LC/MS Found 369.2.

Intermediate 12-B (37 mg, 0.01 mmol) is dissolved in 3 mL of a 25% TFA solution in $CH_2Cl_2$. The reaction is stirred at 23° C. for 1 hour and the solvent is removed in vacuo to provide Reference compound 12 as its mono-trifluoroacetate salt. LC/MS Found 269.2 [M+H].

Reference Compound 13

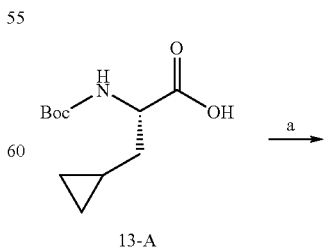

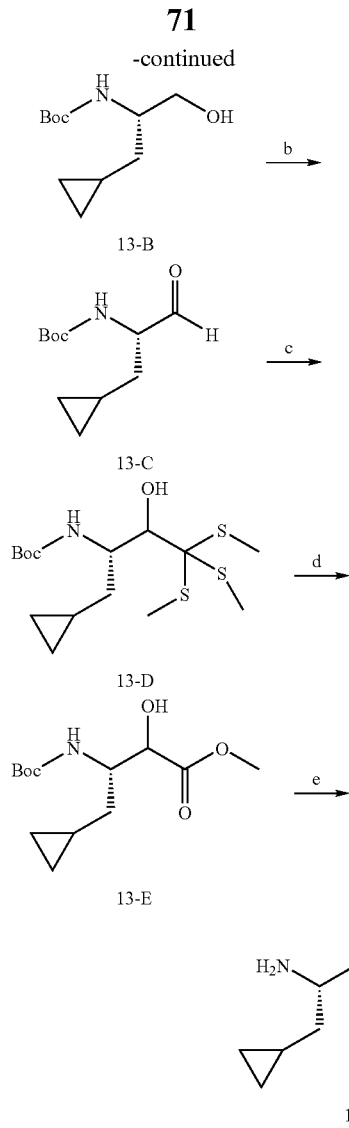

added via syringe followed by dropwise addition of isobutyl-chloroformate (2.26 mL, 17.58 mmol) via syringe over a 10 minute period. A white precipitate formed and the reaction is allowed to stir for another 20 minutes at 0° C. The mixture is filtered and washed with THF; the filtrate is cooled to 0° C. in an ice bath, and a solution of sodium borohydride (1.5 g, 39.3 mmol) dissolved in 30 mL water is added slowly dropwise. The effervescent solution is allowed to warm to room temperature and the THF is removed in vacuo. The residue is redissolved in EtOAc, washed with water, brine, dried over $MgSO_4$, filtered and concentrated in vacuo. Automated silica gel chromatography (0-40% EtOAc in hexanes) provides 13-B as a clear oil. LC/MS Found 216.2 [M+H].

Intermediates 13-C to 13-E are prepared following methods analogous to preparing Reference compound 11, steps a-c, respectively. Intermediate 13-E (268 mg, 0.98 mmol) is dissolved in 5 mL of a 25% TFA solution in $CH_2Cl_2$. The reaction is stirred at 23° C. for 1 hour and the solvent is removed in vacuo to provide Reference Compound 13 as its mono-trifluoroacetate salt. LC/MS Found 174.1 [M+H].

Reference Compound 14

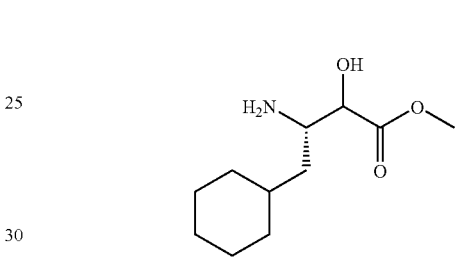

Reference compound 14 is prepared following methods analogous to those for preparing Reference compound 13, using (S)—N-Boc-Cha-OH as the corresponding amino acid starting material in step a.

Reference Compound 15

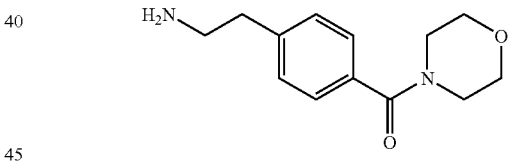

Reference compound 15 is prepared following methods analogous to those preparing Reference compound 3, using morpholine as the corresponding amine starting material in step a.

In the above reaction scheme for Reference compound 14, the reagents and conditions are: (a) (i) i-Butyl chloroformate, $Et_3N$, THF, −10° C.; (ii) $NaBH_4$, $H_2O$, 0° C., 77%; (b) Trichloroisocyanuric acid, TEMPO, $CH_2Cl_2$, 0° C.; (c) n-BuLi, $HC(SCH_3)_3$, THF, −65° C.; (d) $HgCl_2$, HgO, MeOH, $H_2O$, 23° C.; (e) TFA/$CH_2Cl_2$ (1:1), 23° C., 12 h.

Commercially available compound 13-A (3.6 g, 15.72 mmol) is dissolved in THF (50 mL) and cooled to −10° C. in an ice-salt bath. Triethylamine (2.62 mL, 18.86 mmol) is

EXAMPLE 61

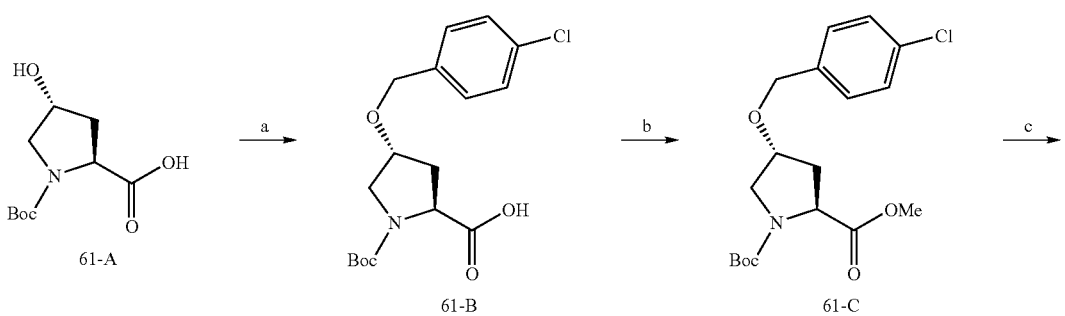

-continued
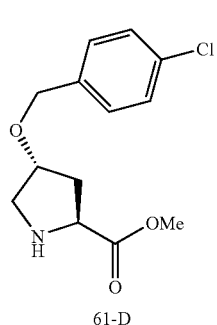
61-D
d →
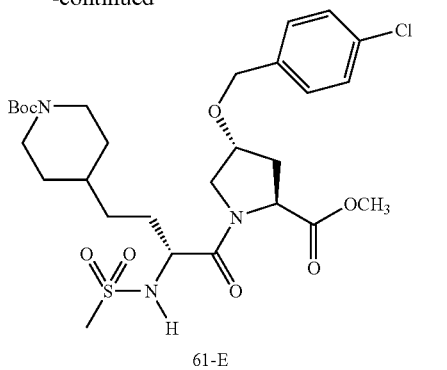
61-E
e →
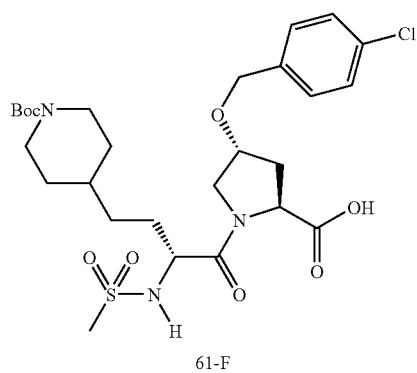
61-F
f →
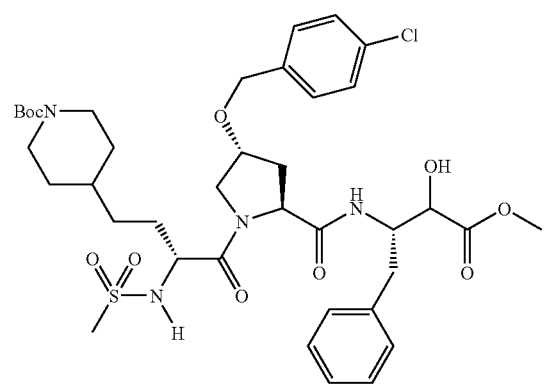
61-G
g →
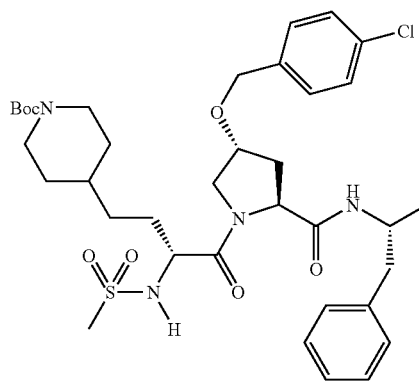
61-H
h →
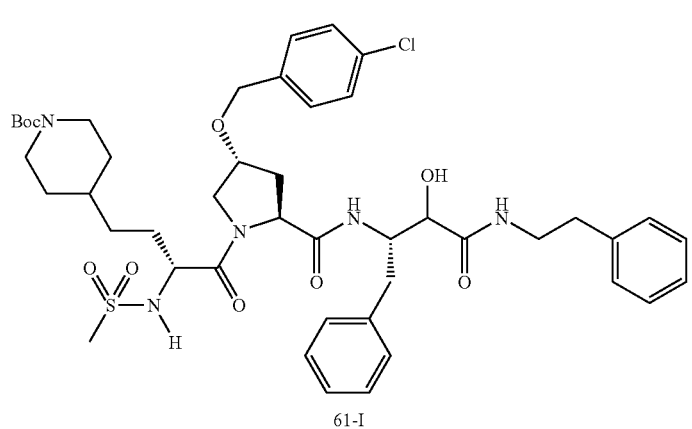
61-I
i →

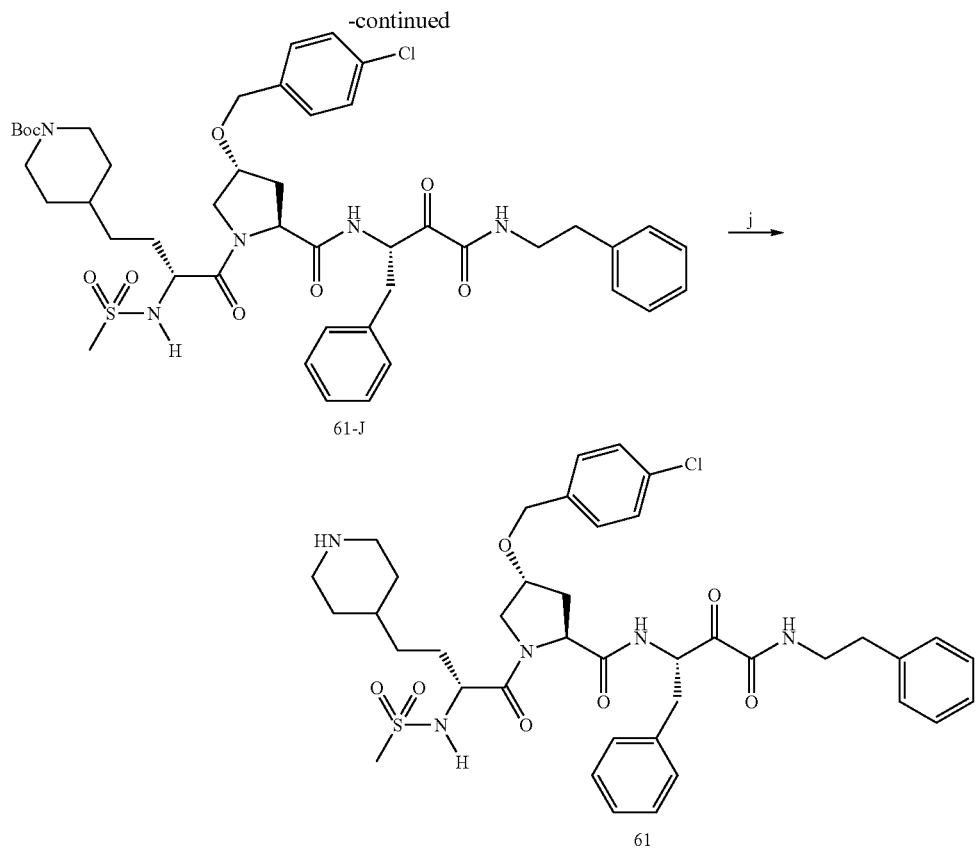

In the above reaction scheme, the reagents and conditions are: (a) KOH, 4-Chlorobenzyl chloride, DMSO, 0° C. to 23° C.; (b) TMS-CHN₂, CH₂Cl₂/MeOH, 23° C.; (c) TFA/CH₂Cl₂ (50:50), 23° C.; (d) HATU/DIPEA/CH₂Cl₂, Reference Compound 8, 23° C.; (e) LiOH, dioxanes/water (4:1), 23° C.; (f) HATU/DIPEA/CH₂Cl₂, Reference Compound 11, 23° C.; (g) LiOH, dioxanes/water (4:1), 23° C.; (h) HATU/DIPEA/CH₂Cl₂, phenethylamine, 23° C.; (h) Dess-Martin Periodinane, CH₂Cl₂, 23° C.; (j) TFA/CH₂Cl₂ (20:80), 23° C., followed by mass-directed HPLC purification.

61-B: Finely powdered KOH (19.4 g, 0.346 mol) is dissolved in DMSO and stirred at room temperature for 20 min and then cooled to 0° C. N-Boc-trans-4-hydroxy-L-proline (Boc-Hyp-OH, 61-A) (10 g, 43.3 mmol) is dissolved in DMSO (10 mL) and added, and the reaction mixture is stirred for an additional 10 min at 0° C. Next, 4-chlorobenzyl chloride (33 g, 0.204 mol) is added, and the reaction mixture is stirred at 0° C. for an additional 15 min, after which point the ice bath is removed and the reaction mixture is allowed to warm to room temperature and stirred for 4 h. The reaction mixture is poured into water (300 mL), and the reaction vessel is rinsed with an additional aliquot of water (300 mL). The combined aqueous layer is extracted with ether (2×300 mL) and discarded. The aqueous layer is acidified with 87% H₃PO₄ to pH 2.3 and then extracted with ether (3×300 mL). The combined ether extracts are washed with water (2×400 mL) and brine (2×400 mL), and then dried over MgSO₄, filtered and concentrated in vacuo. The residue is purified by chromatography on silica gel with EtOAc/Hexanes (gradient 0 to 100%) to yield the compound 61-B as clear oil. MS m/z 256.1 (M+1-Boc); ¹H NMR (DMSO-D₆, 400 MHz) δ 7.39-7.31 (4H, m), 4.52-4.40 (2H, m), 4.16-4.10 (2H, m), 3.48-3.41 (2H, m), 2.40-2.30 (1H, m), 2.03-1.94 (1H, m), 1.39-1.34 (9H, m).

61-C: A solution of (trimethylsilyl)diazomethane (2M in diethylether) (4.7 ml, 9.45 mmol) is added to carboxylic acid 61-B (2.4 g, 8.6 mmol) dissolved in CH₂Cl₂/MeOH 5:1 (25 mL) at room temperature. When the starting material had been consumed as determined by LCMS, the reaction mixture is quenched with acetic acid, concentrated in vacuo, and the crude residue is purified by flash chromatography (gradient EtOAc:Hexanes) to afford the methyl ester 61-C as a clear oil.

61-D: A round bottomed flask is charged with a stirbar and 61-C (1.03 g, 2.80 mmol). TFA (50%) in CH₂Cl₂ (6 mL) is added and the solution is stirred for 1 h at room temperature. The solvent is removed in vacuo, hexanes is added and then evaporated again in vacuo to dryness, and repeated if necessary to azeotrope remaining TFA. The crude material 61-D is used directly in the next step without further purification.

61-E: The crude material 61-D (3.06 g, 8.0 mmol) is dissolved in CH₂Cl₂ (50 mL), to which Reference Compound 8 (1.5 g, 4.12 mmol) and HATU (3.2 g, 8.0 mmol) are added, and the solution is stirred at room temperature for 10 min. DIPEA (2.5 mL, 12.4 mmol) is added via syringe and the reaction mixture is allowed to stir overnight at room temperature. The solvent is removed in vacuo, and the crude material is directly purified by flash chromatography (120 g silica, hexanes/EtOAc gradient). The solvent is removed in vacuo to afford 61-E as an oily semisolid. LC/MS Found 616.3 [M+H].

61-F: Methyl ester 61-E (3.0 g, 4.9 mmol) is dissolved in dioxane (50 mL). Lithium hydroxide (234 mg, 9.8 mmol) is dissolved in water (50 mL) and added dropwise to the solution of methyl ester 61-E, and allowed to stir for 3 h at room temperature. The reaction mixture is concentrated in vacuo to remove dioxane and then acidified with 1M NaHSO₄. This is extracted with EtOAc, and the combined organic layer is washed with brine and dried with MgSO$_4$. The solvent is removed in vacuo to afford carboxylic acid 61-F as a waxy solid. LC/MS Found 602.2 [M+H].

61-G: Carboxylic acid 61-F (170 mg, 0.28 mmol) is dissolved in CH$_2$Cl$_2$ (5 mL). Reference Compound 11 (89 mg, 0.43 mmol) and HATU (162 mg, 0.43 mmol) are added, and the mixture is stirred for 10 min at room temperature. DIPEA (250 µL, 1.28 mmol) is added via syringe, and the reaction mixture is left to stir for 3 hours at room temperature. The solvent is removed in vacuo. The crude is redissolved in EtOAc (50 mL) and washed with 1M HCl (2×25 mL), followed by saturated aqueous NaHCO$_3$ (2×25 mL) and brine (25 mL), and dried with anhydrous Na$_2$SO$_4$. The solvent is removed in vacuo, and the crude material is directly purified by flash chromatography (40 g silica, 0-5% MeOH/CH$_2$Cl$_2$ gradient). The solvent is removed in vacuo to afford 61-G as an oily semisolid. LC/MS Found 793.3 [M+H].

61-H: Methyl ester 61-G (155 mg, 0.20 mmol) is dissolved in dioxane (5 mL). Lithium hydroxide (7.1 mg, 0.29 mmol) is dissolved in water (5 mL) and added dropwise to the solution of methyl ester 61-G, and allowed to stir for 3 h at room temperature. The reaction mixture is concentrated in vacuo to remove dioxane, and then acidified with 1M NaHSO$_4$. This is extracted with EtOAc, and the combined organic layer is washed with brine and dried with MgSO$_4$. The solvent is removed in vacuo to afford carboxylic acid 61-H as a waxy solid. LC/MS Found 779.3 [M+H].

61-I: Carboxylic acid 61-H (50 mg, 0.07 mmol) is dissolved in CH$_2$Cl$_2$ (5 mL). Phenethylamine (19 µL, 0.13 mmol) and HATU (50 mg, 0.13 mmol) are added, and the mixture is stirred for 10 min at room temperature. DIPEA (35 µL, 0.20 mmol) is added via syringe, and the reaction mixture is left to stir for 3 hours at room temperature. The solvent is removed in vacuo; the crude material is redissolved in EtOAc (50 mL) and washed with 1M HCl (2×25 mL), followed by saturated aqueous NaHCO$_3$ (2×25 mL) and brine (25 mL), and dried with anhydrous Na$_2$SO$_4$. The solvent is removed in vacuo, and the crude material 61-I is used directly in the next reaction. LC/MS Found 882.4 [M+H].

61-J: Crude alcohol 61-I (62 mg, 0.07 mmol) is dissolved in CH$_2$Cl$_2$ (5 mL), and Dess-Martin periodinane (55 mg, 0.13 mmol) is added. The reaction mixture is stirred for 2 hours at room temperature. The solvent is removed in vacuo, The crude is redissolved in EtOAc (50 mL) and washed with saturated Na$_2$S$_2$O$_3$ (2×25 mL), followed by saturated aqueous NaHCO$_3$ (2×25 mL) and brine (25 mL), and dried with anhydrous Na$_2$SO$_4$. The crude material is purified by automated flash chromatography (40 g silica column) using a gradient of 0-5% MeOH in CH$_2$Cl$_2$ to afford the ketone 61-J as a white foam. LC/MS Found 902.4 [M+Na].

Example 61: Intermediate 61 (42 mg, 0.05 mmol) is dissolved in 20% TFA in CH$_2$Cl$_2$ (2 mL). The reaction is stirred at room temperature for 30 minutes and the solvent is removed in vacuo. The crude material is purified by reverse-phase HPLC and the solvent is lyophilized to afford Example 61 as a white powder as its mono-TFA salt.

EXAMPLES 62-66

Examples 62-66 are prepared following methods analogous to those described in Example 61, using appropriate amine components in the amide formation step in step h. For example, in Example 62, 4-aminomethyl tetrahydropyran is used in place of 4-aminomethyl pyridine as the amine component.

EXAMPLES 67-74

Examples 67-74 are prepared following methods analogous to those described in Example 61, using appropriate amine components in steps (h) and (i), for example:

Example 67, using Reference compounds 13 and 12 in steps f and h, respectively;

Example 68, using Reference compound 14 and 4-aminoethyl tetrahydropyran in steps f and h, respectively;

Examples 69-73, using Reference compound 13 as the amine component in step f and the appropriate amine component in step h. Example 74 is prepared following analogous methods, using appropriate amine components in steps f and h, respectively.

Table 2 shows compounds of Formula (1), as described in Examples 61-74.

TABLE 2

| Compound | Structure | Physical Data MS (m/z), Elemental Analysis, and $^1$H NMR 400 MHz (DMSO-d$_6$) |
|---|---|---|
| 61 | 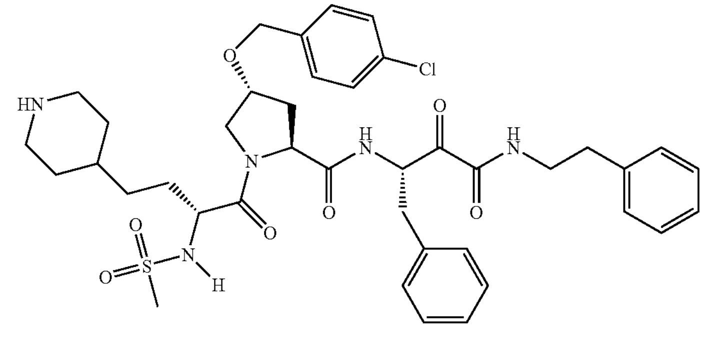 | MS m/z 780.4 (M + 1) |

TABLE 2-continued
| Compound | Structure | Physical Data MS (m/z), Elemental Analysis, and ¹H NMR 400 MHz (DMSO-$d_6$) |
|---|---|---|
| 62 | 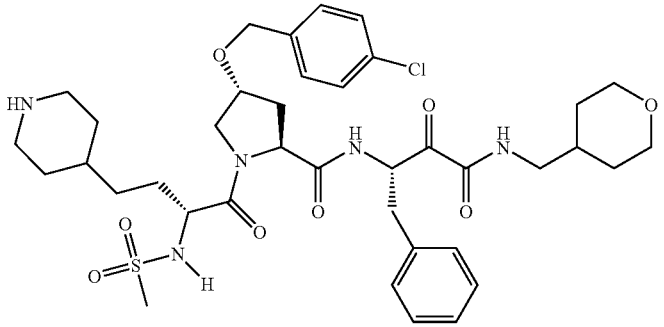 | MS m/z 774.5 (M + 1) |
| 63 | 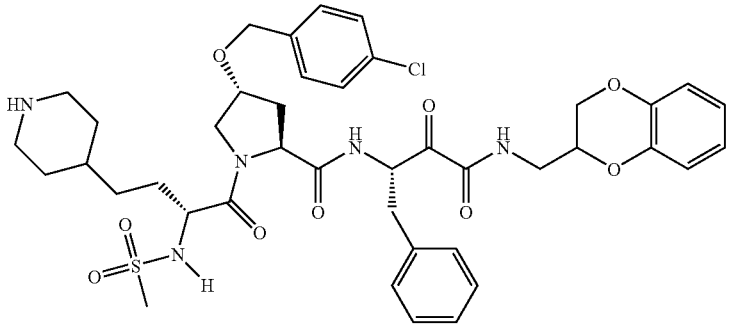 | MS m/z 824.7 (M + 1) |
| 64 | 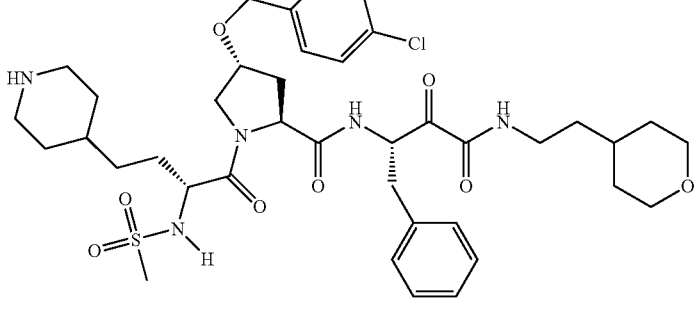 | MS m/z 788.5 (M + 1) |
| 65 | 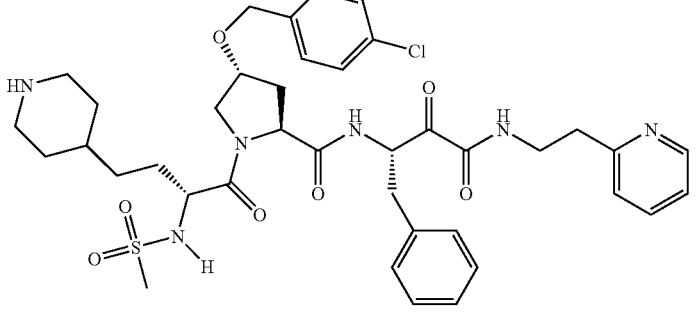 | MS m/z 781.3 (M + 1) |

TABLE 2-continued

| Compound | Structure | Physical Data MS (m/z), Elemental Analysis, and $^1$H NMR 400 MHz (DMSO-d$_6$) |
|---|---|---|
| 66 | 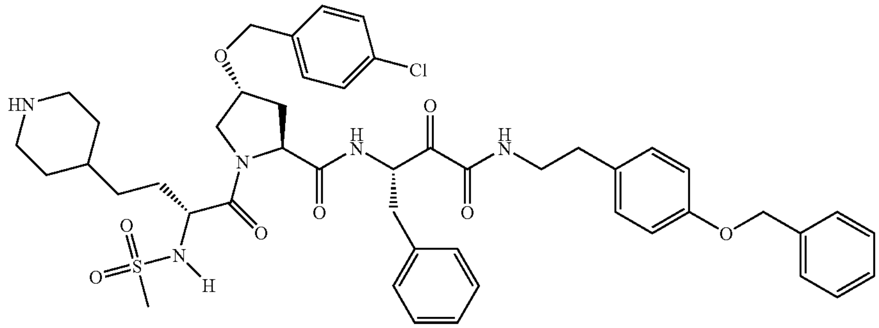 | MS m/z 886.6 (M + 1) |
| 67 | 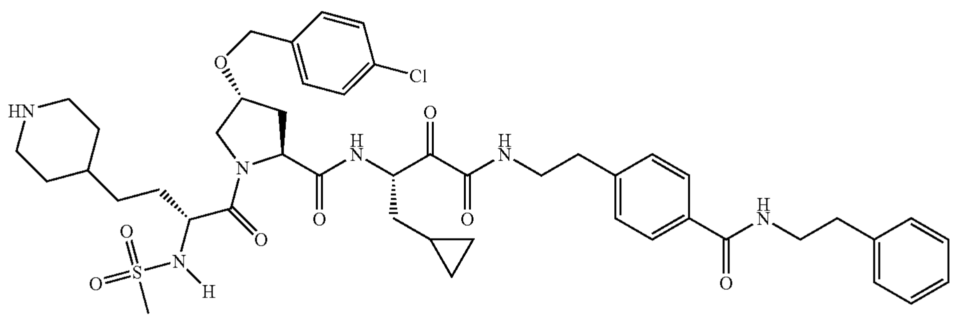 | MS m/z 891.6 (M + 1) |
| 68 | 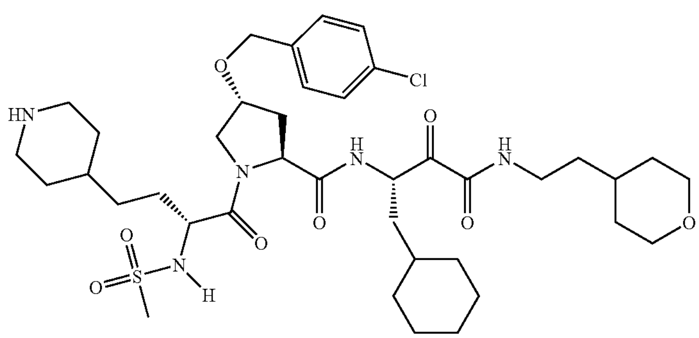 | MS m/z 794.5 (M + 1) |
| 69 | 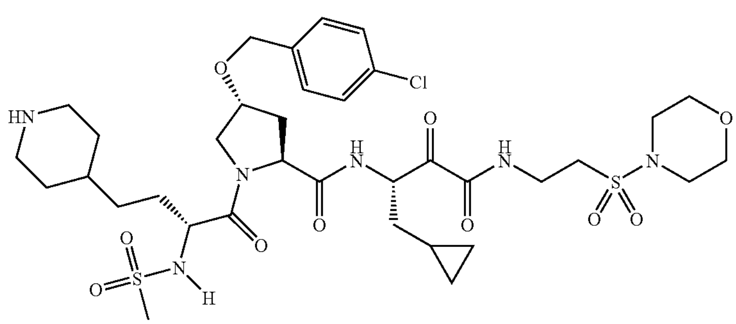 | MS m/z 817.5 (M + 1) |

TABLE 2-continued
| Compound | Structure | Physical Data MS (m/z), Elemental Analysis, and $^1$H NMR 400 MHz (DMSO-$d_6$) |
|---|---|---|
| 70 | 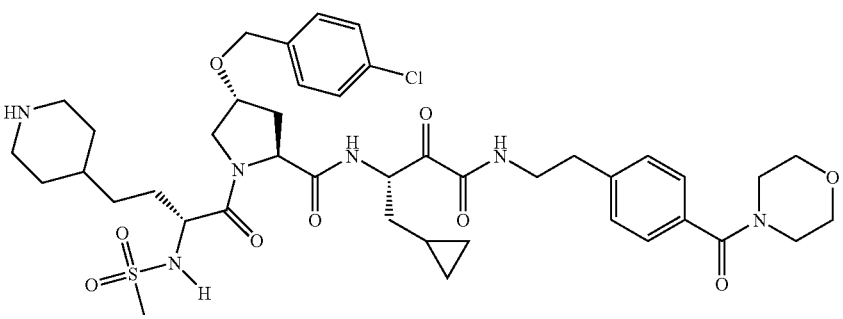 | MS m/z 857.5 (M + 1) |
| 71 | 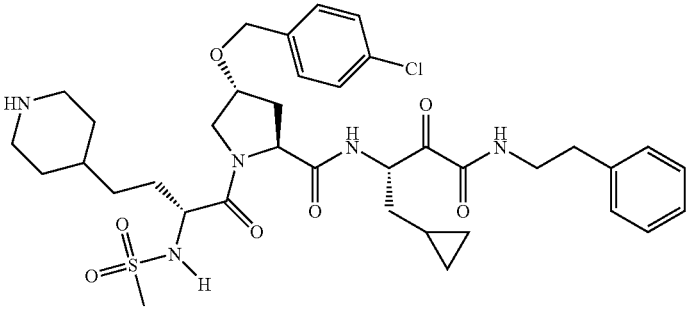 | MS m/z 744.4 (M + 1) |
| 72 | 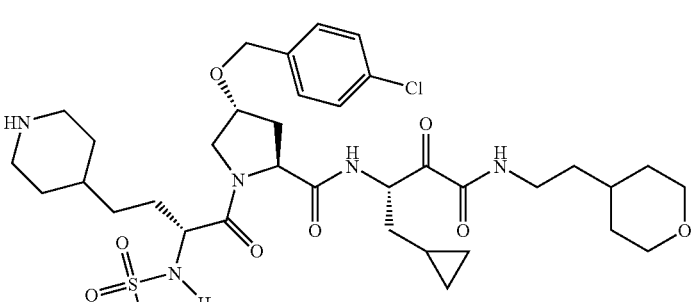 | MS m/z 752.5 (M + 1) |
| 73 | 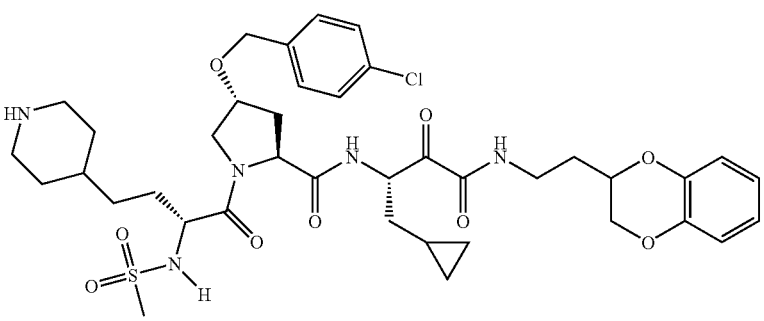 | MS m/z 788.5 (M + 1) |

TABLE 2-continued

| Compound | Structure | Physical Data MS (m/z), Elemental Analysis, and $^1$H NMR 400 MHz (DMSO-$d_6$) |
|---|---|---|
| 74 | 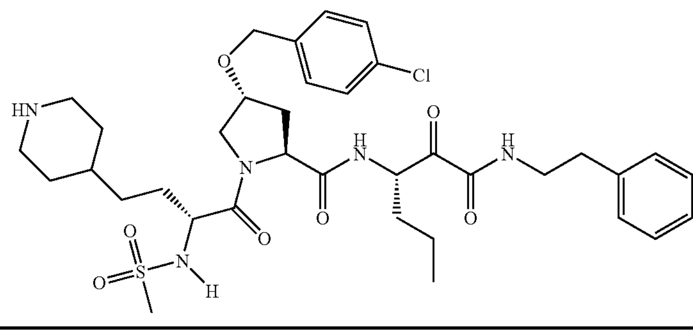 | MS m/z 731.4 (M + 1) |

Assays

The suitability of a channel activating protease inhibitor such as a prostasin inhibitor for the treatment of a disease mediated by inhibition of a channel activating protease may be tested by determining the inhibitory effect of the channel activating protease inhibitor on: (1) the native, isolated, purified or recombinant channel activating protease, using a suitable biochemical assay format, using the method described in Shipway et al.; Biochemical and Biophysical Research Communications 2004; 324(2):953-63; and/or (2) the ion channel/ion transport function in suitable isolated cells or confluent epithelia, using the methods described in Bridges et al.; American Journal of Physiology Lung Cell Molecular Physiology 2001; 281(1):L16-23; and Donaldson et al.; Journal of Biological Chemistry 2002; 277(10):8338-45.

Biochemical Assays

Recombinant human prostasin and matriptase and guinea pig prostasin are generated according to methods described in Shipway et al., Biochem. and Biophys. Res. Commun. 2004; 324(2):953-63. The recombinant enzymes are incubated in an electrolyte buffer containing the test compounds or vehicle in a suitable multiple well assay plate such as a 96 or 384 well plate. At a defined time after the mixing of enzyme with compound or vehicle, a suitable fluorescent peptide substrate is added to the assay mixture. As substrate becomes cleaved by the active enzyme, fluorescence (measured, using a suitable fluorescence plate reader) increases and the rate of turnover of substrate (i.e. enzyme activity) may be quantified and thus the inhibitory effect of any test compound. The efficacy of test compounds is expressed as the concentration that induces 50% attenuation in the enzyme activity ($K_i$).

In general, compounds of the invention may have $K_i$ values from 0.1 nM to 5 µM. In some examples, compounds of the invention may have $K_i$ values from 0.1 nM to 500 nM; from 0.1 nM to 50 nM; from 0.1 nM to 5 nM; or from 0.1 nM to 0.5 nM. In particular examples, compounds of the invention may have $K_i$ values from 0.1 nM to 0.5 nM; from 0.5 nM to 5 nM; from 5 nM to 50 nM; from 50 nM to 500 nM; or from 500 nM to 5 µM. In yet other examples, compounds may have $K_i$ values less than 0.1 nM or more than 5 µM.

Epithelial Ion Transport

Human bronchial epithelial cells are cultured according to methods described in Danahay et al., Am. J. Physiol. Lung Cell Mol. Physiol. 2002; 282(2):L226-36. When suitably differentiated (days 14-21 after establishing an apical-air interface), epithelial cells are treated with either vehicle, aprotinin (200 µg/ml) or test compound for 90 minutes. Epithelia are then placed into chambers as described in Danahay et al., supra, maintaining the concentration of vehicle, aprotinin or test compound on the apical side of the epithelia. Short circuit current (ISC) is then measured by voltage clamping the epithelia to zero millivolts. The amiloride-sensitive ISC is then measured by the addition of amiloride (10 µM) to the apical surface of the epithelia. The potency of the test compound is expressed as the concentration inducing a 50% inhibition of the total aprotinin-sensitive component of the amiloride-sensitive ISC.

In general, compounds of the invention may have $IC_{50}$ values from 1 nM to 10 µM. In some examples, compounds of the invention may have $IC_{50}$ values from 1 nM to 1 µM; or more particularly from 1 nM to 100 nM. In yet other examples, compounds of the invention may have $IC_{50}$ values from 100 nM to 1 µM, or from 1 µM to 10 µM. In yet other examples, compounds may have $IC_{50}$ values less than 1 nM or more than 10 µM.

Tracheal Potential Difference (In Vivo)

Guinea pigs are anaesthetized, using a short acting inhalation anaesthesia such as halothane and $N_2O$. While under short acting anaesthesia, an oral gavage needle is inserted into the trachea via the oropharangeal route. Once inside the trachea, a small volume (50-200 µl) of vehicle or test compound, in a suitable aqueous-based diluent, is instilled into the airways. Animals then recover and become fully ambulatory. Alternatively, test compounds may be administered to animals, using aerosol or dry powder dosing. At a defined time after dosing, the animals are surgically anaesthetized, using a suitable anaesthesia such as ketamine and xylazine. The trachea is then exposed and a plastic agar bridge electrode is inserted into the tracheal lumen. A reference electrode is also inserted into the layers of muscle in the animal's neck. The tracheal potential difference is then measured, using a suitable high impedance voltmeter as described in Takahashi et al., Toxicol Appl Pharmacol. 1995; 131(1):31-6. The potency of the test compound is expressed as the dose inducing a 50% reduction in the sensitive-component of the tracheal potential difference.

It is understood that the examples and embodiments described herein are for illustrative purposes only and that various modifications or changes in light thereof will be suggested to persons skilled in the art and are to be included

The invention claimed is:

1. A compound of Formula (1):

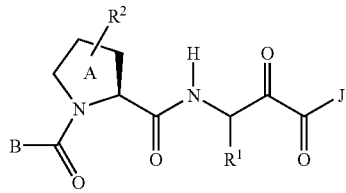 (1)

or pharmaceutically acceptable salts thereof; wherein B is

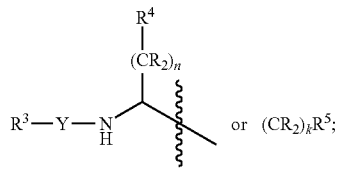

Y is —SO$_2$—, or —O—C(=O)—;
J is OH, OCH$_3$, NH—CH(phenyl)$_2$, NH(CH$_2$)$_1$—OR$^6$, NH(CH$_2$)$_1$—SO$_2$—R$^6$, NH(CR$_2$)$_1$—R$^6$ or

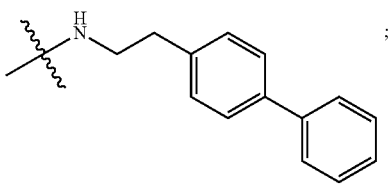

wherein R$^6$ is C$_{1-6}$ alkyl, or phenyl, pyridyl, cyclopropyl, cyclohexyl, benzothiazolyl, 2,3-dihydro-1H-indenyl, morpholinyl, imidazolyl, tetrahydropyranyl, piperidinyl, thiophenyl, 2,3-dihydrobenzo[b][1,4]-dioxinyl or benzothiophenyl, each of which is optionally substituted by C$_{1-6}$ alkyl, halo, hydroxyl, C$_{1-6}$ alkoxy, SO$_2$NR$_2$, CONR$^8$R$^9$, O(CR$_2$)$_1$R$^5$ wherein R$^5$ is phenyl, or CONR(CR$_2$)$_1$R$^6$ wherein R$^6$ is phenyl;
R$^1$ is —(CH$_2$)$_m$—NH$_2$, —(CH$_2$)$_m$—NHC(=NH)—NH$_2$, or (CR$_2$)$_m$—X wherein X is piperidinyl, C$_{3-7}$ cycloalkyl or phenyl; or R$^1$ is C$_{1-6}$ alkyl;
R$^2$ is a substituent at any position on ring A and is —O—(CR$_2$)$_p$—R$^7$ or —OC(O)—NR$^8$R$^9$;
R$^3$ is C$_{1-6}$ alkyl, cyclohexyl, or —(CR$_2$)$_1$—R$^7$;
R$^4$ is C$_{2-6}$ alkenyl or —CR=CR—R$^6$ wherein R$^6$ is C$_{1-6}$ alkyl or phenyl substituted by C$_{1-6}$alkoxy; or R$^4$ is phenyl, piperidinyl or

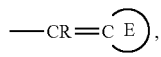

wherein ring E is cyclohexyl unsubstituted or substituted by NR$_2$; or ring E is piperidinyl;

R$^5$ is thiazolyl;
R$^7$ is a phenyl unsubstituted or substituted by halo;
R$^8$ and R$^9$ together with N form a 6 membered heterocyclic ring;
each R is H or C$_{1-6}$ alkyl;
l is 0-4;
m is 1-4;
n is 1-2; and
k, p and q are 1.

2. The compound of claim 1, wherein R$^2$ is —O—(CH$_2$)—R$^7$ and R$^7$ is a halo-substituted phenyl.

3. The compound of claim 1, wherein said compound has Formula (3):

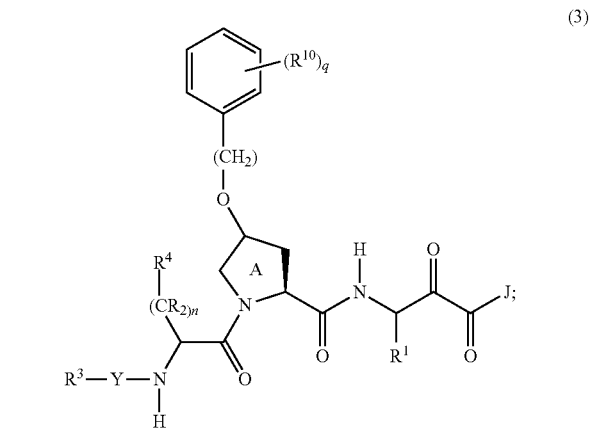 (3)

or pharmaceutically acceptable salts thereof; wherein
R$^{10}$ is halo, C$_{1-6}$ alkyl, or O(C$_{1-6}$ alkyl); and
R, R$^1$, R$^3$, R$^4$, J, Y, n and q are as defined in claim 1.

4. The compound of claim 3, wherein R$^1$ is —(CH$_2$)$_m$—NH$_2$, —(CH$_2$)$_m$—NHC(=NH)—NH$_2$, or (CH$_2$)$_m$—X wherein X is piperidinyl.

5. The compound of claim 3, wherein R$^3$ is C$_{1-6}$ alkyl, cyclohexyl, or benzyl.

6. The compound of claim 3, wherein R$^4$ is piperidinyl.

7. The compound of claim 1, wherein R$^1$ is (CR$_2$)$_m$—X wherein X is C$_{3-7}$ cycloalkyl or phenyl;
R$^4$ is piperidinyl; and
Y is SO$_2$.

8. The compound of claim 1, wherein said compound has Formula (2):

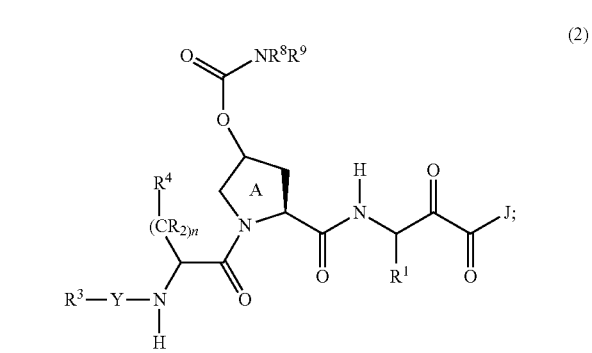 (2)

or pharmaceutically acceptable salts thereof; wherein
R$^8$ and R$^9$ together form piperidinyl; and
R, R$^1$, R$^3$, R$^4$, J, Y and n are as defined in claim 1.

9. The compound of claim 1, wherein said compound has Formula (4):
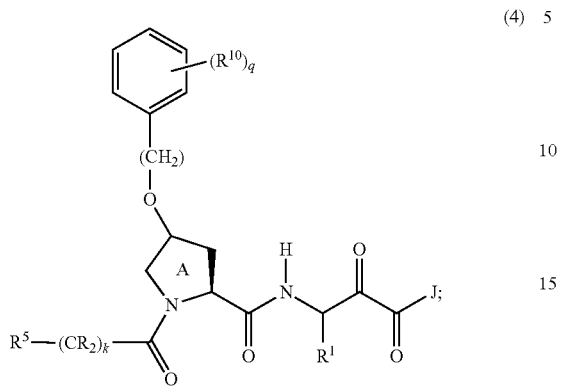
or pharmaceutically acceptable salts thereof; wherein
$R^{10}$ is halo, $C_{1-6}$ alkyl, or $O(C_{1-6}$ alkyl); and
$R, R^1, R^5, J, k$ and $q$ are as defined in claim 1.
10. The compound of claim 9, wherein $R^5$ is thiazolyl, optionally substituted with $NR^8R^9$.
11. The compound of claim 1, selected from the group consisting of:
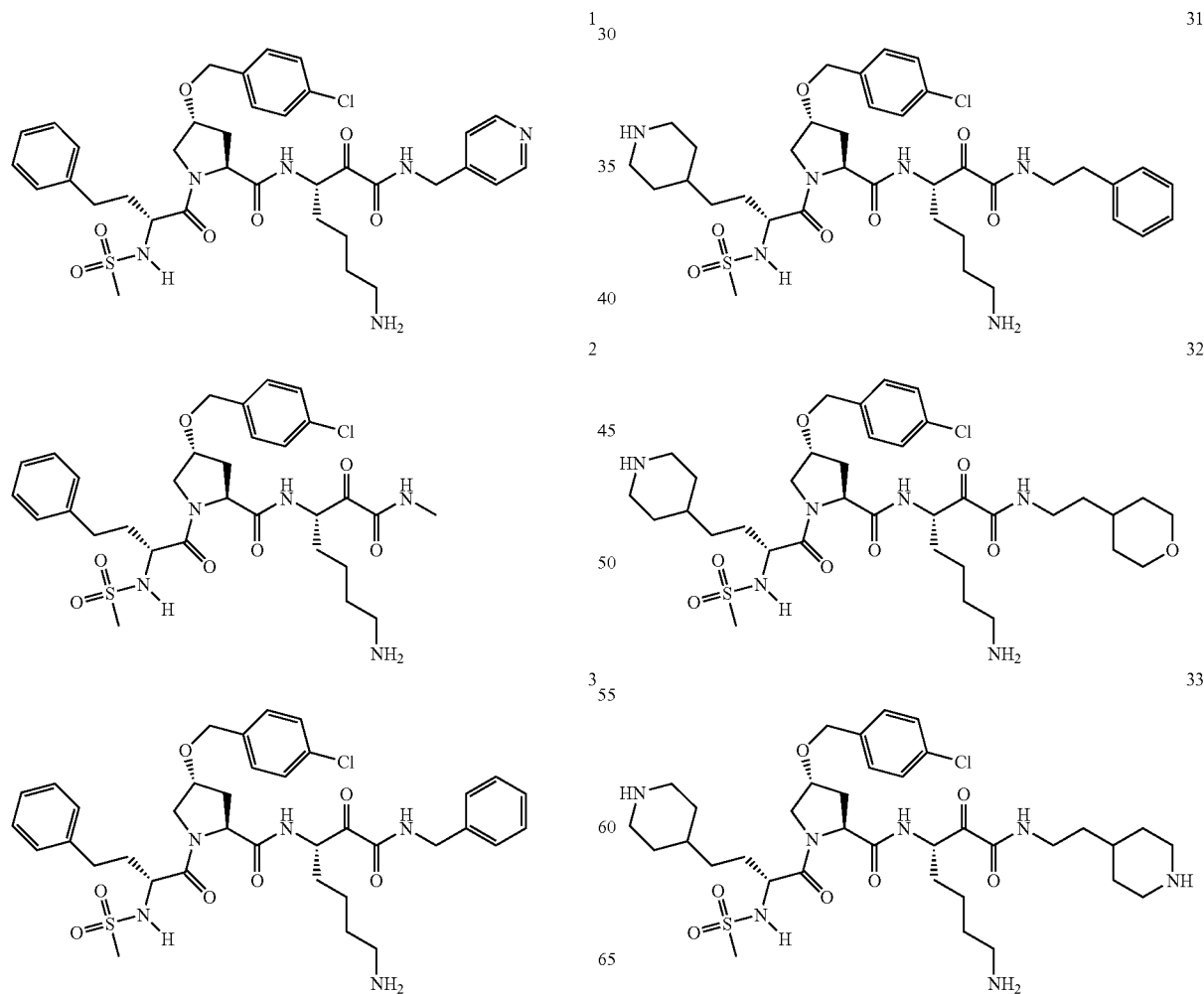

| 4 | 34 |
|---|---|
| 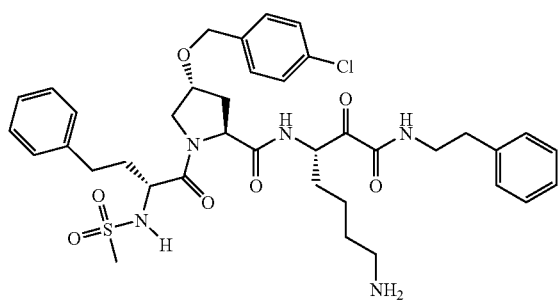 | 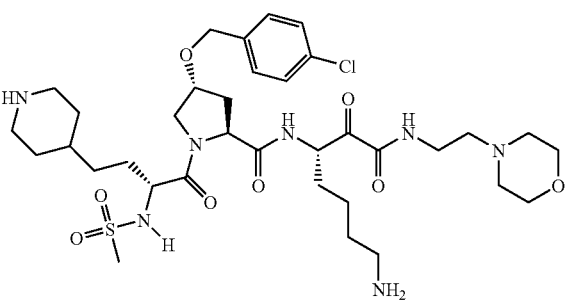 |
| 5 | 35 |
|---|---|
| 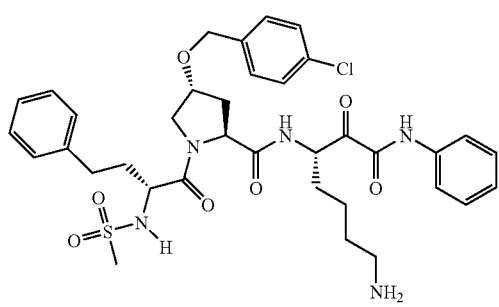 | 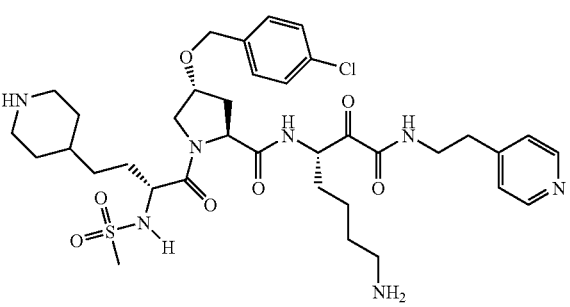 |
| 6 | 36 |
|---|---|
| 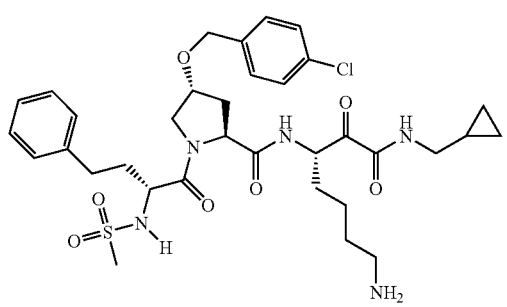 | 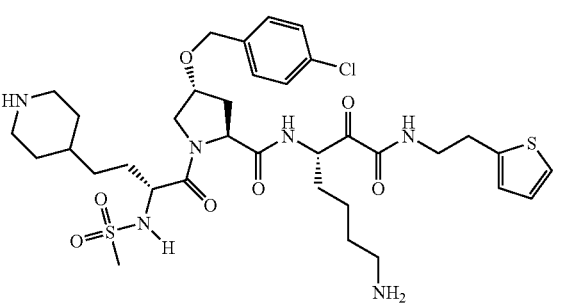 |
| 7 | 37 |
|---|---|
| 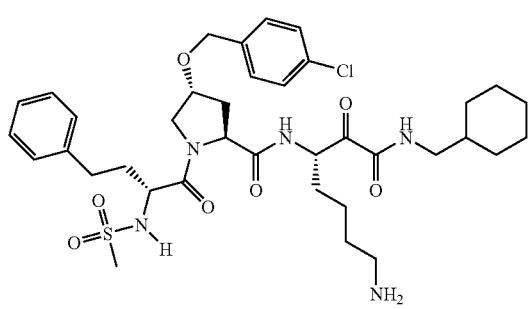 | 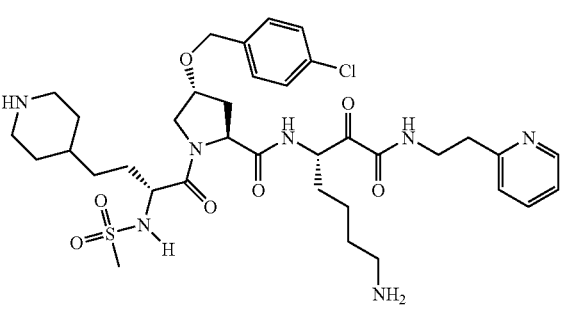 |
| 8 | 38 |
|---|---|
| 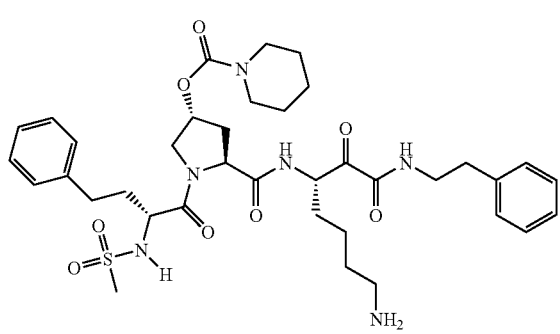 | 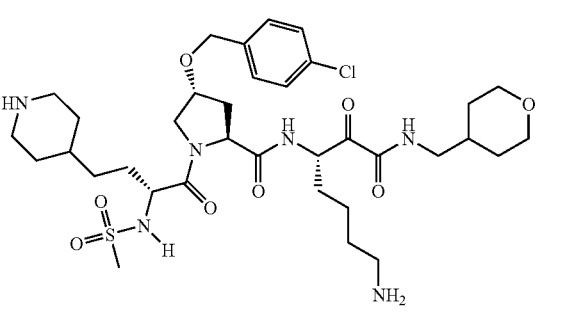 |

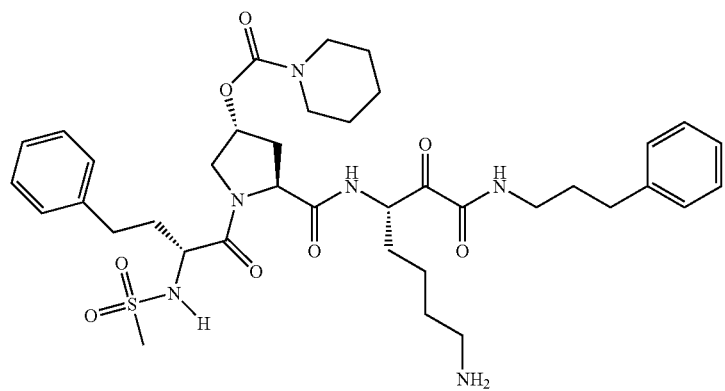
9
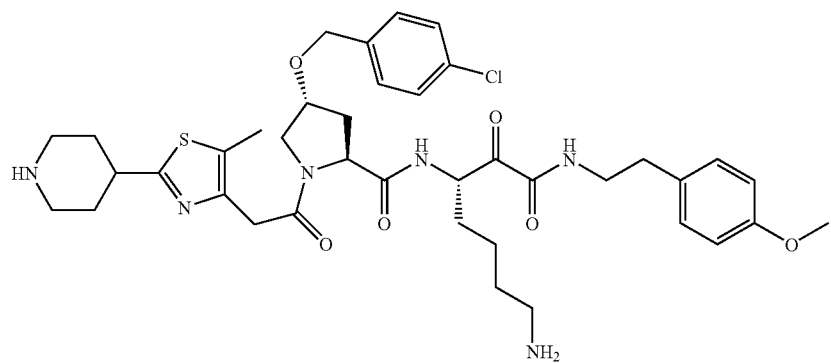
39
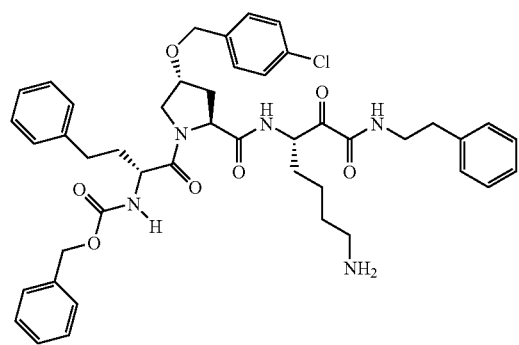
10
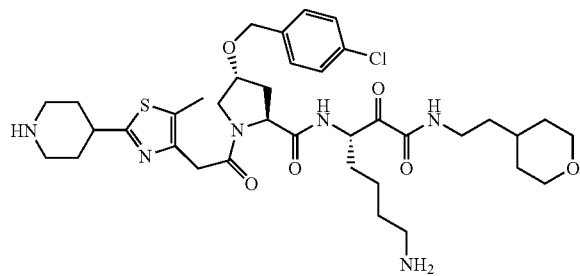
40
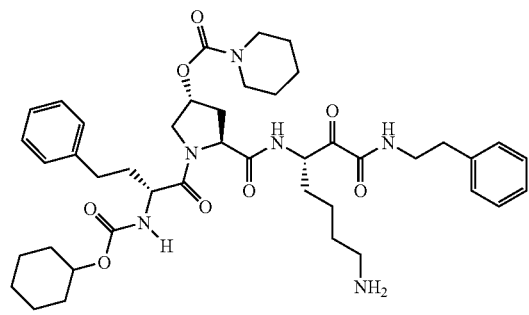
11

-continued
12
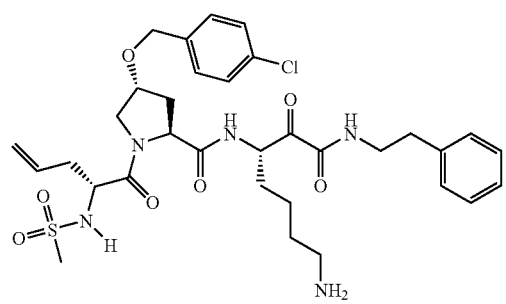
42
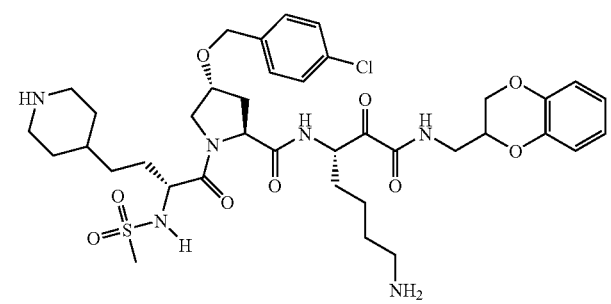
13
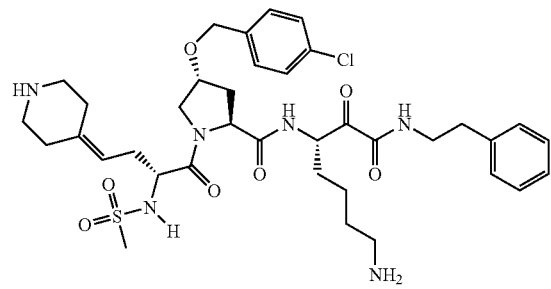
43
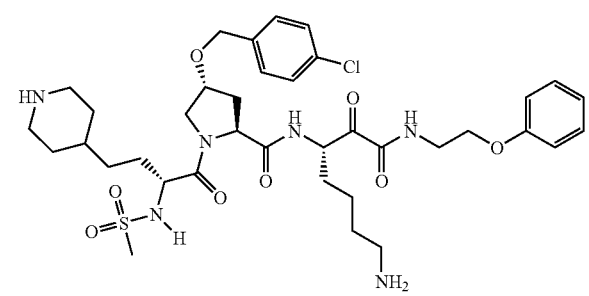
14
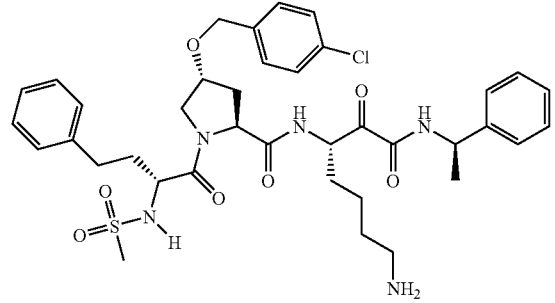
44
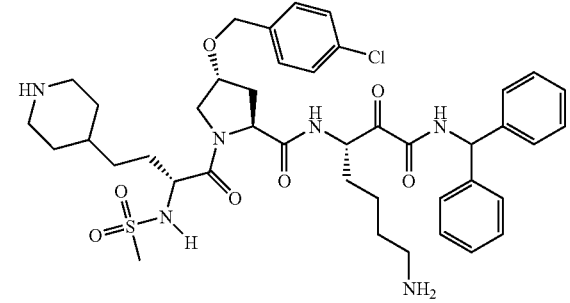
15
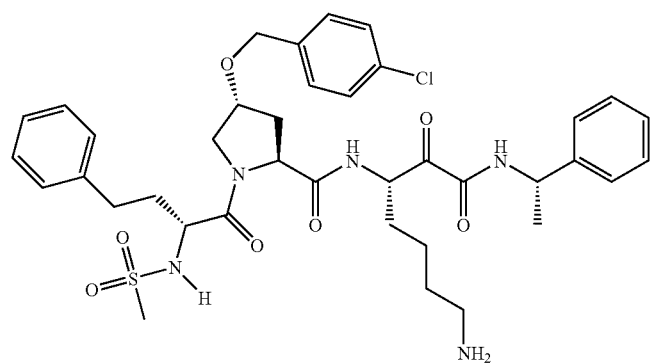

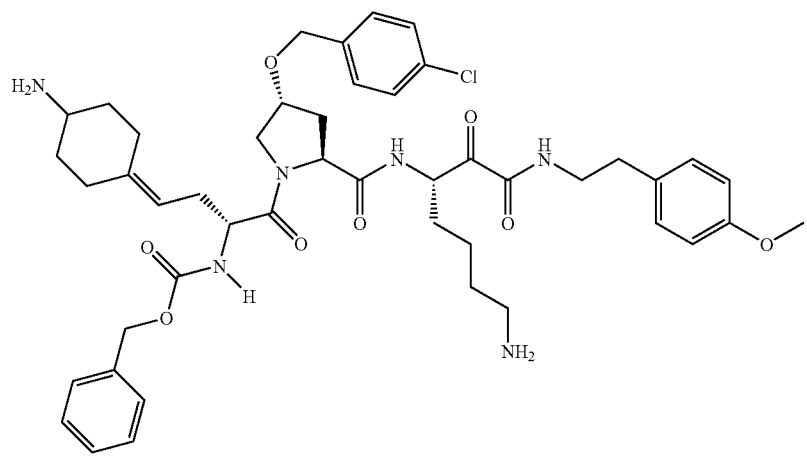
45
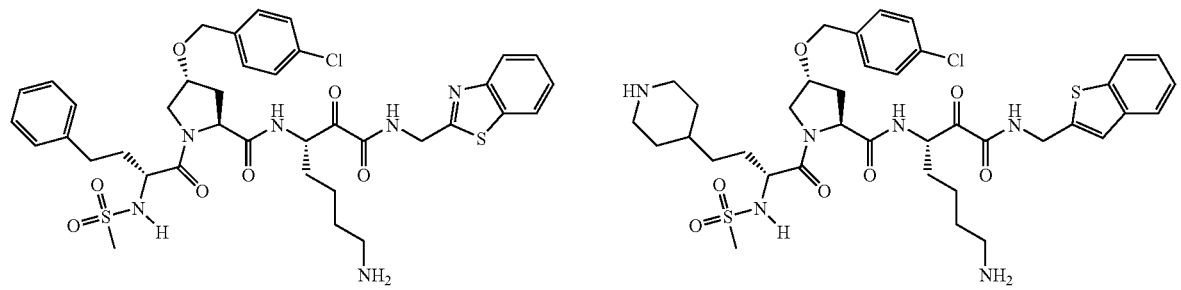
16
46
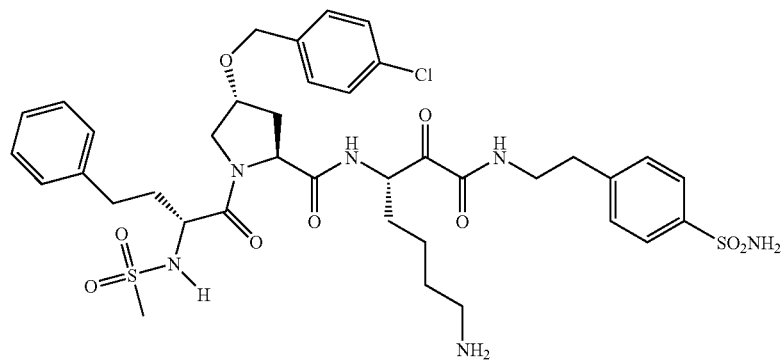
17
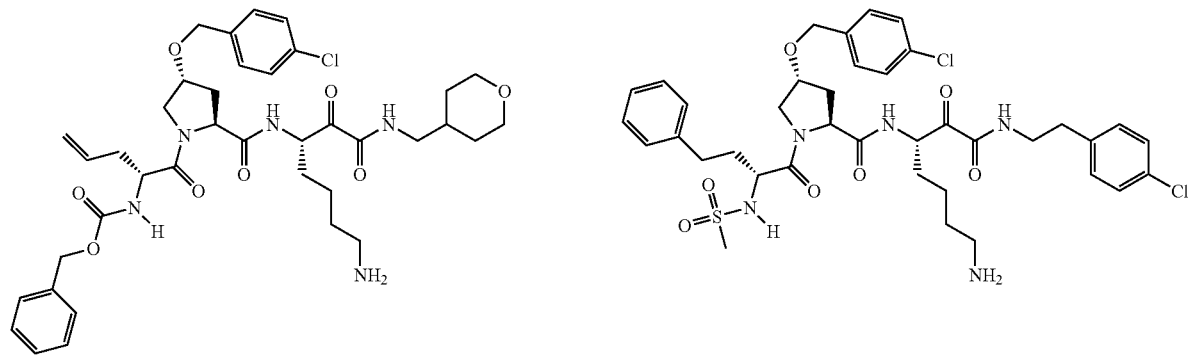
47
18

-continued
48
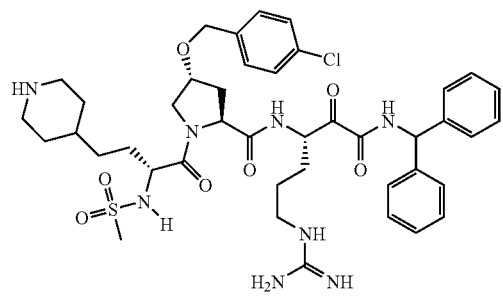
19
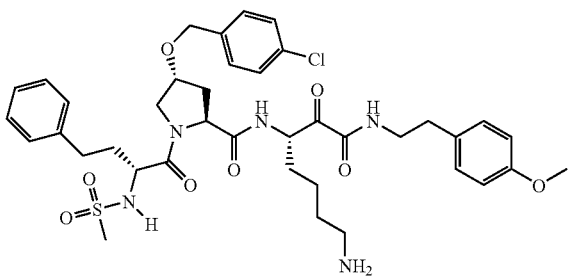
49
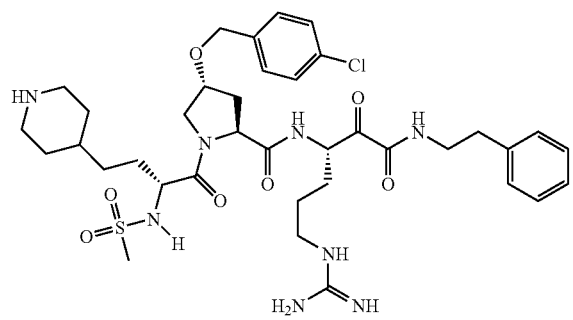
20
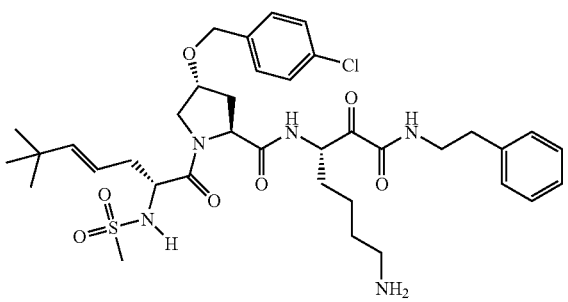
50
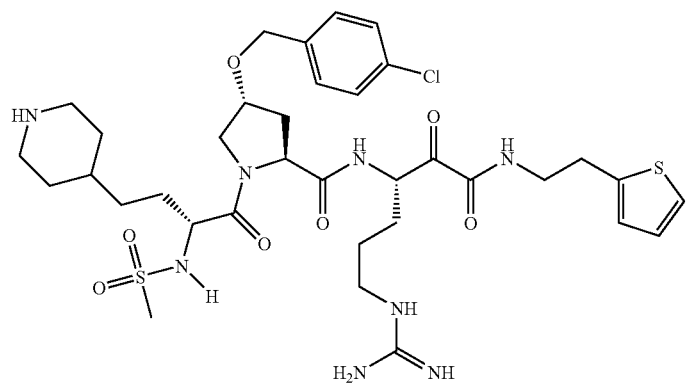
21
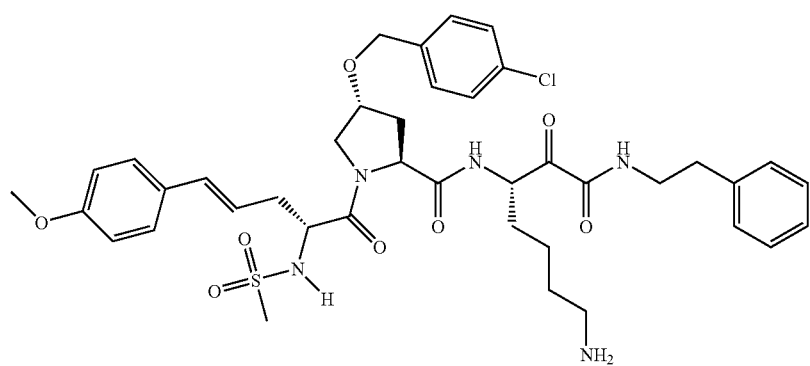

101 102
-continued
51
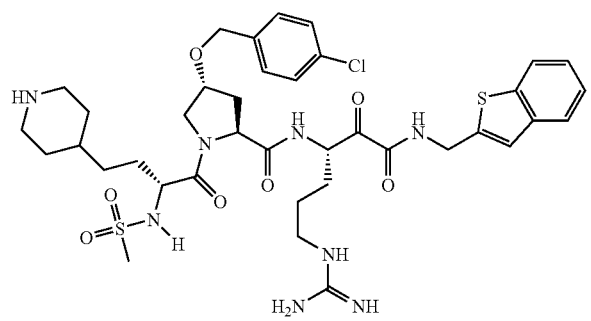
22
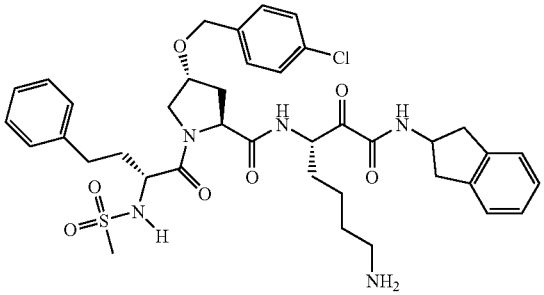
52
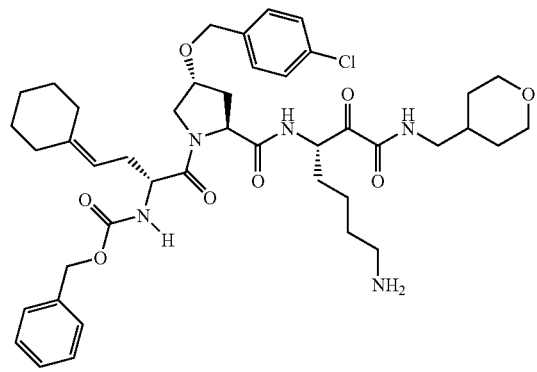
23
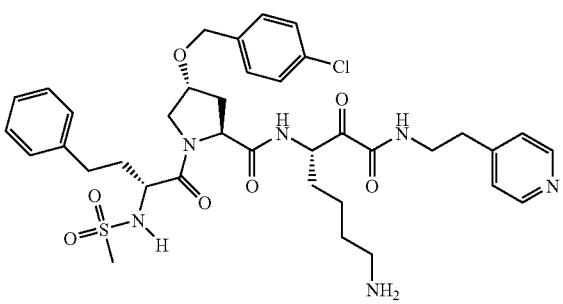
53
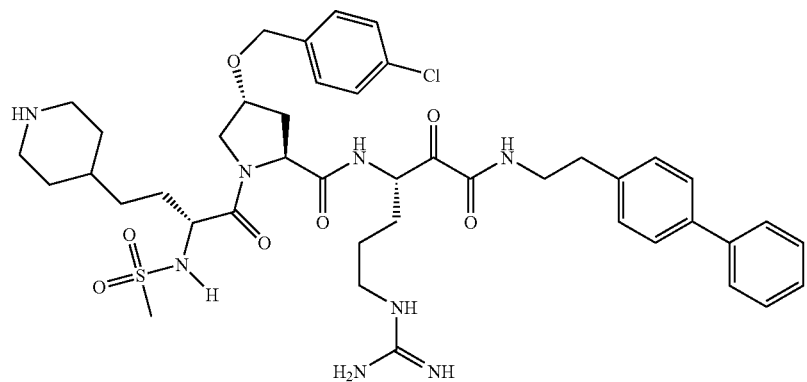
24
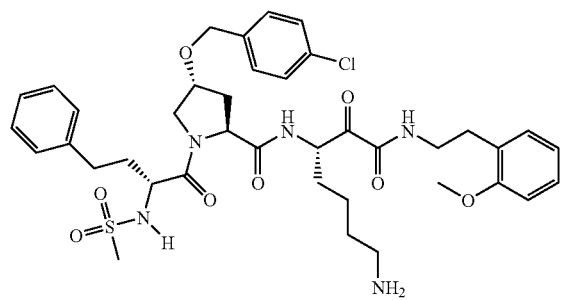
54
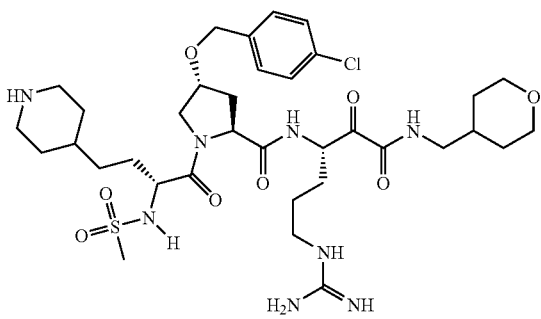

-continued
| 103 | 104 |
|---|---|
| 25 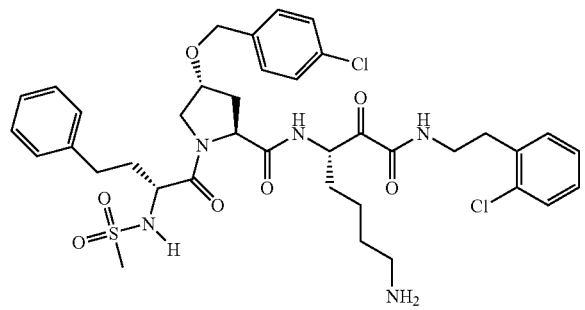 | 55 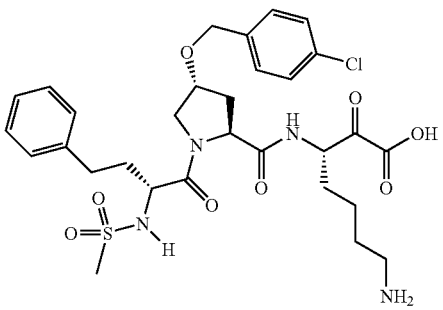 |
| 26 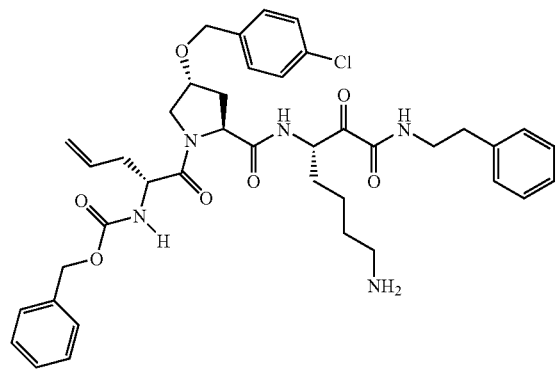 | 56 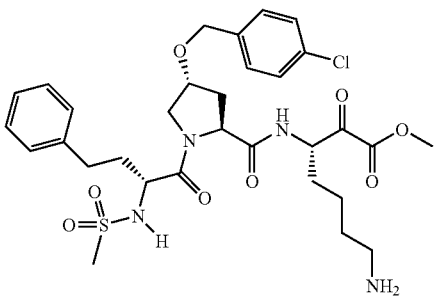 |
| 27 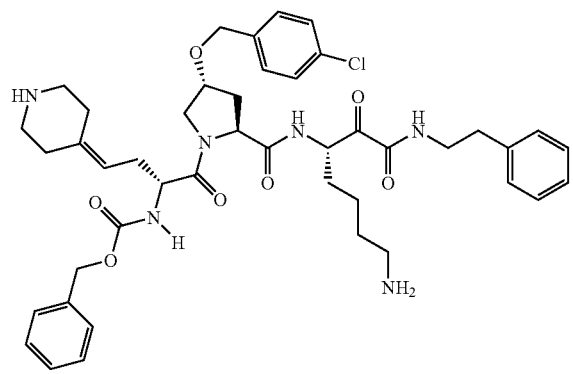 | 57 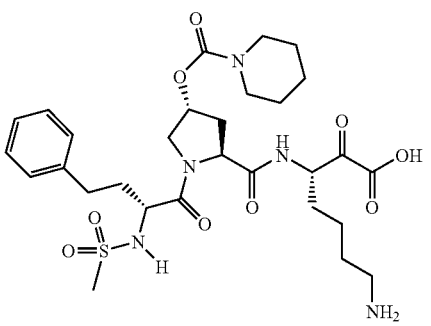 |
| 28 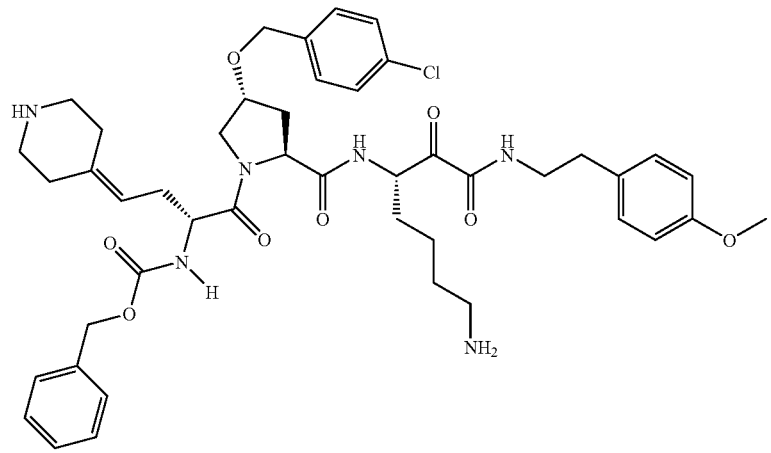 | |

58
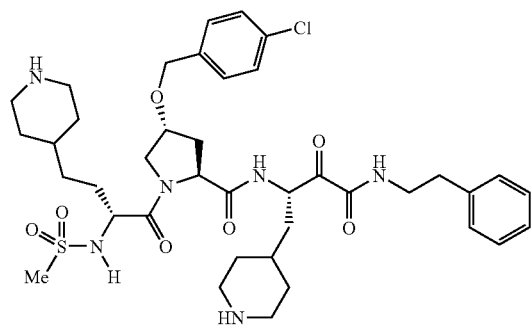
29
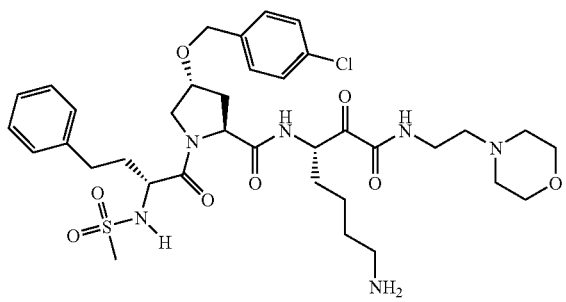
59
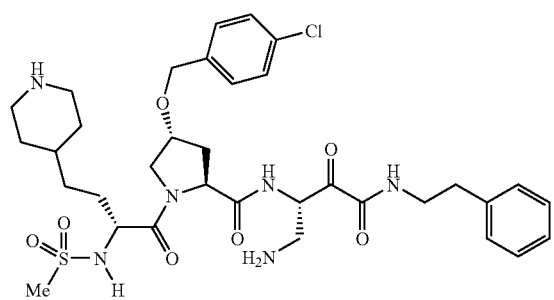
30
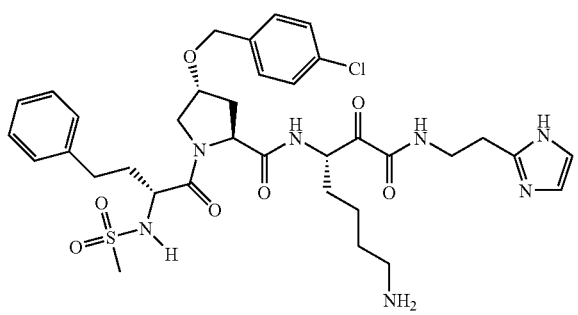
60
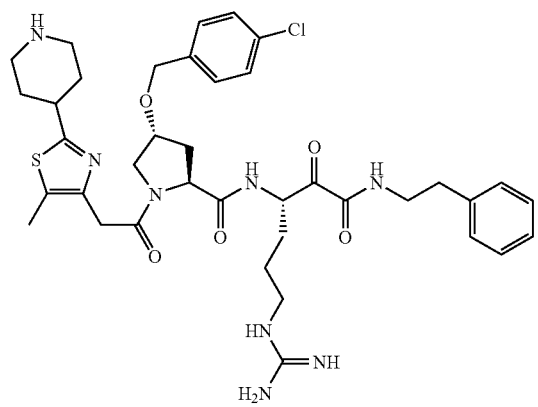
61
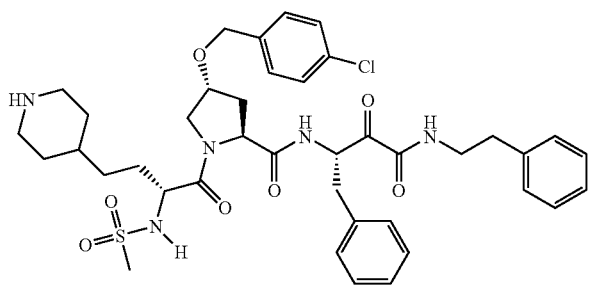
68
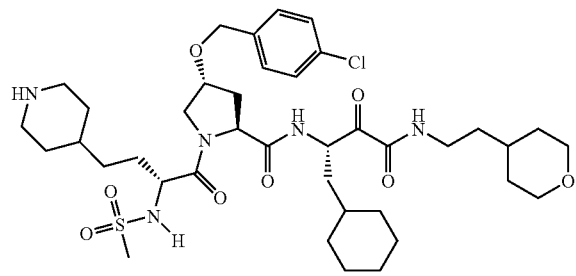
62
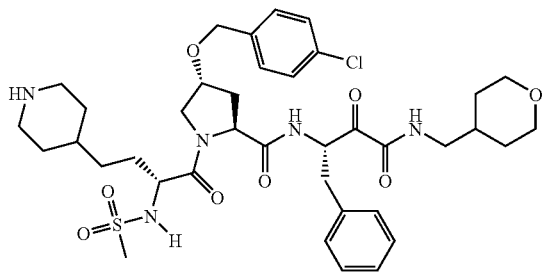

-continued
69
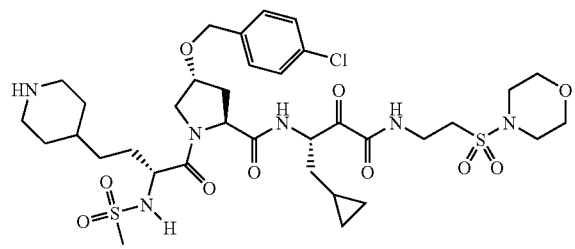
63
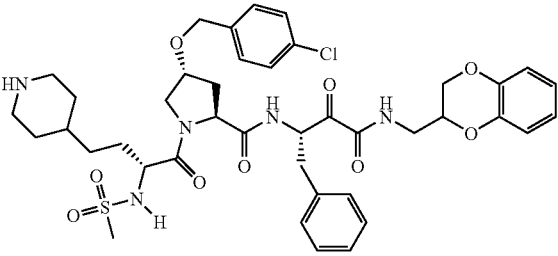
70
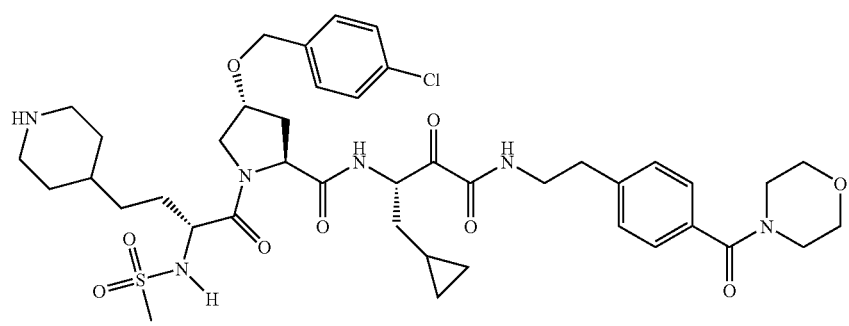
64
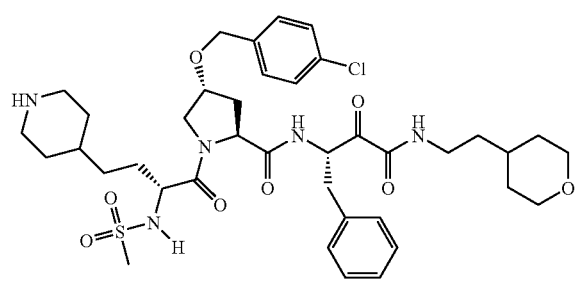
71
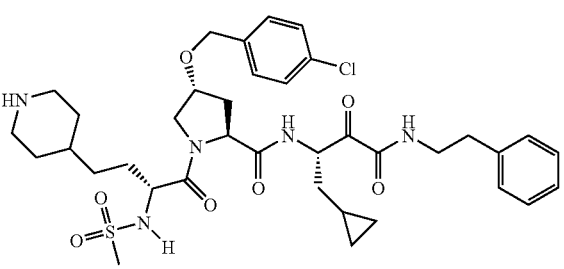
65
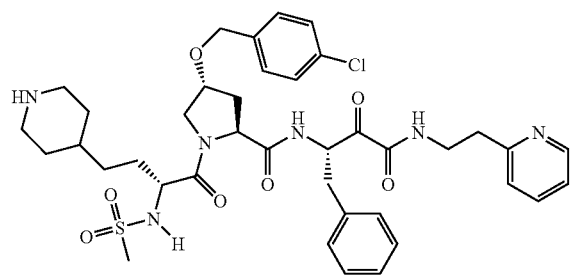
72
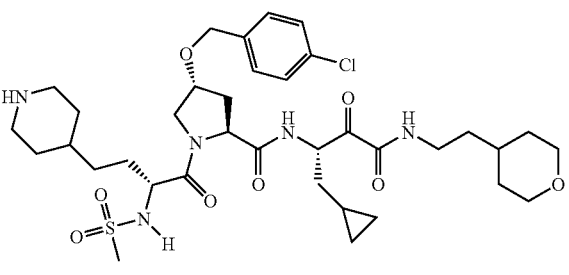
66
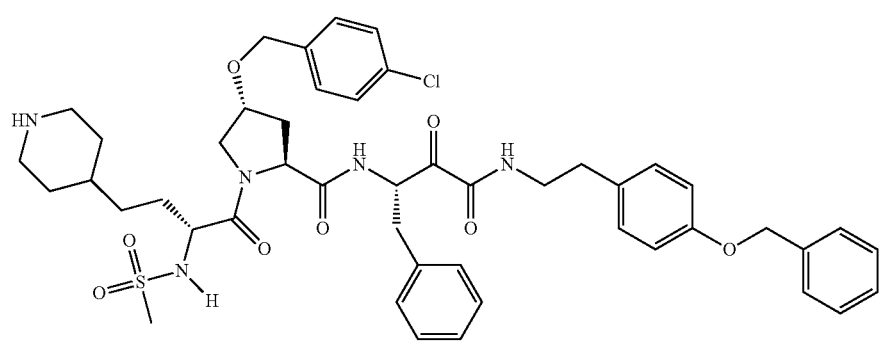

-continued
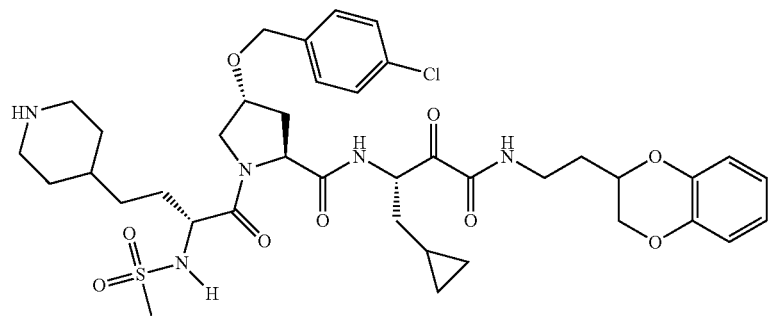
73
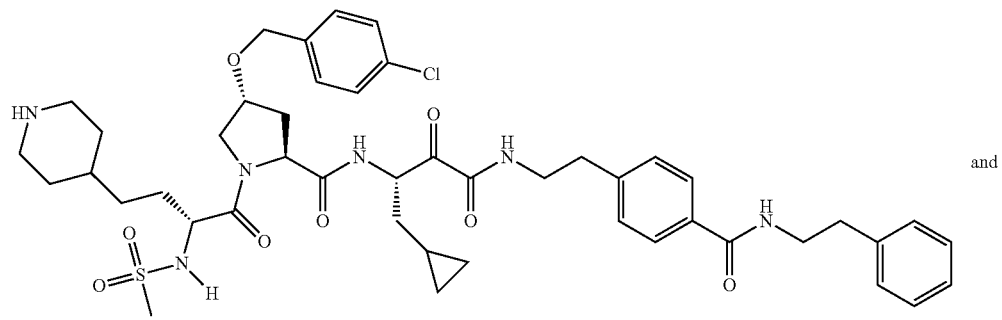
67
and
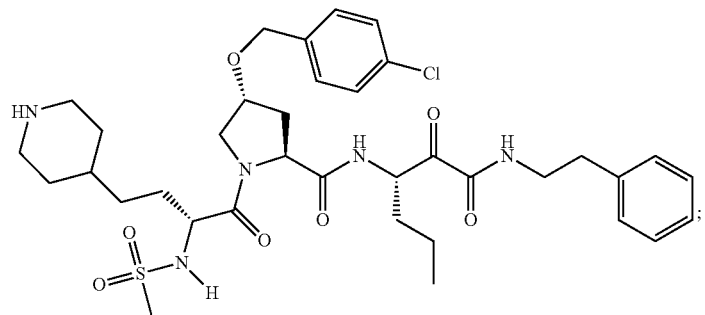
74
or pharmaceutically acceptable salts thereof.
12. A pharmaceutical composition comprising a therapeutically effective amount of a compound of claim 1.
* * * * *